US009675612B2

(12) United States Patent
Klar et al.

(10) Patent No.: US 9,675,612 B2
(45) Date of Patent: Jun. 13, 2017

(54) SUBSTITUTED THIAZOLOPYRIMIDINES

(71) Applicant: BAYER PHARMA AKTIENGESELLSCHAFT, Berlin (DE)

(72) Inventors: Ulrich Klar, Berlin (DE); Lars Wortmann, Berlin (DE); Keith Graham, Berlin (DE); Florian Puehler, Cambridge, MA (US); Detlev Sülzle, Berlin (DE); Georg Kettschau, Berlin (DE); Philip Lienau, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 1 day.

(21) Appl. No.: 14/772,693

(22) PCT Filed: Mar. 3, 2014

(86) PCT No.: PCT/EP2014/054028
§ 371 (c)(1),
(2) Date: Sep. 3, 2015

(87) PCT Pub. No.: WO2014/135480
PCT Pub. Date: Sep. 12, 2014

(65) Prior Publication Data
US 2016/0009734 A1    Jan. 14, 2016

(30) Foreign Application Priority Data

Mar. 6, 2013 (EP) ..................... 13157909

(51) Int. Cl.
A61K 31/497 (2006.01)
C07D 239/70 (2006.01)
C07D 513/04 (2006.01)

(52) U.S. Cl.
CPC .......... *A61K 31/497* (2013.01); *C07D 239/70* (2013.01); *C07D 513/04* (2013.01)

(58) Field of Classification Search
CPC ............................ A61K 31/497; C07D 239/70
USPC ...................... 514/210.18; 544/262
See application file for complete search history.

(56) References Cited

U.S. PATENT DOCUMENTS

| 5,011,472 | A | 4/1991 | Aebischer et al. |
| 5,023,252 | A | 6/1991 | Hseih |
| 5,444,038 | A | 8/1995 | James et al. |
| 2008/0269238 | A1 | 10/2008 | Sugihara et al. |
| 2009/0156599 | A1* | 6/2009 | Branstetter .......... A61K 31/497 514/234.2 |
| 2011/0212103 | A1 | 9/2011 | Heckel et al. |
| 2015/0133425 | A1 | 5/2015 | Kettschau et al. |
| 2015/0152121 | A1 | 6/2015 | Klar et al. |
| 2015/0218173 | A1 | 8/2015 | Wortmann et al. |
| 2015/0239891 | A1 | 8/2015 | Klar et al. |
| 2015/0252047 | A1 | 9/2015 | Klar et al. |
| 2016/0002245 | A1 | 1/2016 | Klar et al. |

FOREIGN PATENT DOCUMENTS

| JP | 200784494 A | 4/2007 |
| WO | 02088138 A1 | 11/2002 |
| WO | 2005010008 A1 | 2/2005 |
| WO | 2006136402 A1 | 12/2006 |
| WO | 2007059905 A2 | 5/2007 |
| WO | 2009134658 A2 | 11/2009 |
| WO | 2010006032 A1 | 1/2010 |
| WO | 2010023181 A1 | 3/2010 |
| WO | 2011104334 A1 | 9/2011 |
| WO | 2011104337 A1 | 9/2011 |
| WO | 2011104338 A1 | 9/2011 |
| WO | 2011104340 A1 | 9/2011 |

OTHER PUBLICATIONS

Knauf et al, Gene Review: MKNK, open online article on WikiGenes, 2016.*
Lim et al, Proc. Natl. Acad. Sci. (2013).*
Jauch, Ralf, et al., Crystal Structures of the Mnk2 Kinase Domain Reveal an Inhibitory Conformation and a Zinc Binding Site, Structure, vol. 13, pp. 1559-1568 (2005).
Jauch, Ralf, et al., Mitogen-activated protein kinases interacting kinases are autoinhibited by a reprogrammed activation segment, EMBO Journal, vol. 25, pp. 4020-4032 (2006).
Buxade, Maria, et al., The Mnks: MAP kinase-interacting kinases (MAP kinase signal-integrating kinases), Frontiers in Bioscience, vol. 13, pp. 5359-5374 (2008).
Konicek, Bruce W., et al., Targeting the eIF4F translation initiation complex for cancer therapy, Cell Cycle, vol. 7, No. 16, pp. 2466-2471 (2008).
Ueda, Takeshi, et al., Mnk2 and Mnk1 Are Essential for Constitutive and Inducible Phosphorylation of Eukaryotic Initiation Factor 4E but Not for Cell Growth or Development, Molecular and Cellular Biology, vol. 24, No. 15, pp. 6539-6549 (2004).

(Continued)

*Primary Examiner* — Kamal Saeed
*Assistant Examiner* — Janet L Coppins
(74) *Attorney, Agent, or Firm* — Nixon & Vaderhye P.C.

(57) ABSTRACT

The present invention relates to substituted thiazolopyrimidine compounds of general formula I as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of a hyperproliferative and/or angiogenesis disorder, as a sole agent or in combination with other active ingredients.

11 Claims, No Drawings

(56) References Cited

OTHER PUBLICATIONS

Blagden, Sarah P., et al., The biological and therapeutic relevance of mRNA translation in cancer, Nat. Rev. Clin. Oncol., vol. 8, No. 5, pp. 280-291 (2011).
Yoshizawa, Akihiko, et al., Overexpression of Phospho-eIF4E is Associated with Survival through AKT Pathway in Non-Small Cell Lung Cancer, Clin Cancer Res, vol. 16, No. 1, pp. 240-248 (2009).
Chrestensen, Carol A., et al., Loss of MNK function sensitizes fibroblasts to serum-withdrawal induced apoptosis, Genes to Cells, vol. 12, pp. 1133-1140 (2007).
Chrestensen, Carol A., et al., MNK1 and MNK2 Regulation in HER2-overexpressing Breast Cancer Lines*, Journal of Biological Chemistry, vol. 282, No. 7, pp. 4243-4252 (2007).
Wendel, Hans-Guido, et al., Dissecting eIF4E action in tumorigenesis, Genes and Development vol. 21, No. 24, pp. 3232-3237 (2007).
Konicek, Bruce W., et al., Therapeutic Inhibition of MAP Kinase Interacting Kinase Blocks Eukaryotic Initiation Factor 4E Phosphorylation and Suppresses Outgrowth of Experimental Lung Metastases, Cancer Res, vol. 71, No. 5, pp. 1849-1857 (2011).
Park, Song-Eun, et al., Efficient Palladium-Catalyzed Amination of Aryl Chlorides Using Dicyclo-hexylamino[(2,6-dimethyl)morpholino]phenylphosphine as a PN2 Ligand, Synthesis, No. 5, pp. 815-823 (2009).
Gewald, Karl, et al., 2-Amino-thiophene aus methylenaktiven Nitrilen, Carbonylverbindungen and Schwefel, Chem. Ber., vol. 99, pp. 94-100 (1966).
Greene, Theodora W., et al., Protective Groups in Organic Sythesis, Third Edition, Wiley (1999).
Berge, Stephen M., et al., Pharmaceutical Salts, Journal of Pharmaceutical Sciences, vol. 66, No. 1, pp. 1-19 (1977).
Wheeler, Rob C., et al., A General, One-Step Synthesis of Substituted Indazoles using a Flow Reactor, Org. Process Res. Dev., vol. 15, pp. 565-569 (2011).
Lukin, Kirill, et al., New Practical Synthesis of Indazoles via Condensation of o-Fluorobenzaldehydes and Their O-Methyloximes with Hydrazine, J. Org. Chem., vol. 71, pp. 8166-8172 (2006).
Li, Xiaoming, et al., Structure-Based Design, Synthesis, and Antimicrobial Activity of Indazole-Derived SAH/MTA Nucleosidase Inhibitors, J. Med. Chem., vol. 46, pp. 5663-5673 (2003).
Strickley, Robert G., Parenteral Formulations of Small Molecules Therapeutics Marketed in the United States (1999)—Part I, PDA Journal of Pharmaceutical Science and Technology, vol. 53, No. 6, 324-349 (1999).
Nema, Sandeep, et al., Excipients and Their Use in Injectable Products, PDA Journal of Pharmaceutical Science and Technology, vol. 51, No. 4, pp. 166-171 (1997).
Cunningham, Barbara, A Growing Issue: Cell Proliferation Assays, The Scientist, vol. 15, No. 13, pp. 1-6 (2001).
Crouch, S.P.M., et al., The use of ATP bioluminescence as a measure of cell proliferation and cytotoxicity, Journal of Immonological Methods, vol. 160, pp. 81-88 (1993).
Powell, M.F., et al., Compendium of Excipients for Parenteral Formulations, PDA Journal of Pharmaceutical Science and Technology, vol. 52, No. 5, pp. 238-239 (1998).
Aiello, Lloyd Paul, et al., Vascular Endothelial Growth Factor in Ocular Fluid of Patients with Diabetic Retinopathy and Other Retinal Disorders, The New England Journal of Medicine, vol. 331, No. 22, pp. 1480-1487 (1994).
Lopez, Pedro F., et al., Transdifferentiated Retinal Pigment Epithelial Cells Are Immunoreactive for Vascular Endothelial Growth Factor in Surgically Excised Age-Related Macular Degeneration-Related Choroidal Neovascular Membranes, Invest Ophthalmol Vis. Sci., vol. 37, No. 5, pp. 855-868 (1996).
Sleebs, Brad E., et al., Identification of 5,6-substituted 4-aminothieno[2,3-dlpyrimidines as LIMKI inhibitors, Bioorganic & Medical Chemistry Letters, vol. 21, pp. 5992-5994 (2011).
Porter, H.D., et al., 5-Nitroindazole, Organic Sythesis, Coll., vol. 3, pp. 660 (1955), vol. 20, pp. 73 (1940).
Pe'Er, Jacob, et al., Hypoxia-Induced Expression of Vascular Endothelial Growth Factor by Retinal Cells is a Common Factor in Neovascularizing Ocular Diseases, Laboratory Investigation, vol. 72, No. 6, pp. 638-645 (1995).
Mass, Robert D., The HER Receptor Family: A Rich Target for Therapeutic Development, Int. J. Radiation Oncology Biol. Phys., vol. 58, No. 3, pp. 932-940 (2004).
Mountzios, Giannis, et al., Aurora Kinases as Targets for Cancer Therapy, Cancer Treatment Reviews, vol. 34, pp. 175-182 (2008).
Pyne, Susan, et al., Sphingosine Kinase Inhibitors and Cancer: Seeking the Golden Sword of Hercules, Cancer Res., vol. 71, pp. 6576-6582 (2011).
Ferrara, Napoleione, VEGF as a Therapeutic Target in Cancer, Oncology, vol. 69 (Supp 3), pp. 11-16 (2005).
Freshney, Ian R., Culture of Animal Cells, A Manual of Basic Technique, Alan R. Liss, Inc., 7 pgs. (1983).
Gautschi, Oliver, et al., Aurora Kinases as Anticancer Drug Targets, Clin. Cancer Res., vol. 14, No. 6, pp. 1639-1648 (2008).
Golub, T.R., et al., Molecular Classification of Cancer: Class Discovery and Class Prediction by Gene Expression Monitoring, Science, vol. 286, pp. 531-537 (1999).
Cecil Textbook of Medicine, Edited by Bennet, J.C. and Plum, F., 20th Edition, vol. 1, 1004-1010 (1996).
Cohen, Philip, The Development and Therapeutic Potential of Protein Kinase Inhibitors, Current Opinion in Chemical Biology, vol. 3, pp. 459-465 (1999).
Cargnello, Marie, et al., Activation and Function of the MAPKs and their Substrates, the MAPK-Activated Protein Kinases, Microbiology and Molecular Biology Reviews, vol. 75, No. 1, pp. 50-83 (2011).
Qiu, Yun, et al., Signaling Network of the Btk Family Kinases, Oncogene, vol. 19, pp. 5651-5661 (2000).
Fabbro, Doriano, et al., Protein Kinases as Targets for Anticancer Agents: From Inhibitors to Useful Drugs, Pharmacology & Therapeutics, vol. 93, pp. 79-98 (2002).
Jain, Rakesh K., et al., Lessons from Phase III Clinical Trials on Anti-VEGF Therapy for Cancer, Nature Clinical Practice Oncology, vol. 3, No. 1, pp. 24-40 (2006).
Hou, Jiqiang, et al., Targeting Mnks for Cancer Therapy, Oncotarget, vol. 3, No. 2, pp. 118-131 (2012).
Dermer, Gerald B., Bio/Technology, vol. 12, pp. 320 (1994).
Adesso, L., et al. Gemcitable Triggers a Pro-Survival Response in Pancreatic Cancer Cells through Activation of the MNK2/eIF4E Pathway, Oncogene, vol. 32, pp. 2848-2857 (2013).
Shi, Y., et al. MNK Kinases Facilitate c-myc IRES Activity in Rapamycin-Treated Multiple Myeloma Cells, Oncogene, vol. 32, pp. 190-197 (2013).

* cited by examiner

SUBSTITUTED THIAZOLOPYRIMIDINES

The present invention relates to substituted thiazolopyrimidine compounds of general formula I as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of a hyperproliferative and/or angiogenesis disorder, as a sole agent or in combination with other active ingredients.

BACKGROUND OF THE INVENTION

The present invention relates to chemical compounds that inhibit MKNK1 kinase (also known as MAP Kinase interacting Kinase, Mnk1) and/or MKNK2 kinase (also known as MAP Kinase interacting Kinase, Mnk2).

Human MKNKs comprise a group of four proteins encoded by two genes (Gene symbols: MKNK1 and MKNK2) by alternative splicing. The b-forms lack a MAP kinase-binding domain situated at the C-terminus. The catalytic domains of the MKNK1 and MKNK2 are very similar and contain a unique DFD (Asp-Phe-Asp) motif in subdomain VII, which usually is DFG (Asp-Phe-Gly) in other protein kinases and suggested to alter ATP binding [Jauch et al., Structure 13, 1559-1568, 2005 and Jauch et al., EMBO J25, 4020-4032, 2006]. MKNK1a binds to and is activated by ERK and p38 MAP Kinases, but not by JNK1. MKNK2a binds to and is activated only by ERK. MKNK1 b has low activity under all conditions and MKNK2b has a basal activity independent of ERK or p38 MAP Kinase. [Buxade M et al., Frontiers in Bioscience 5359-5374, May 1, 2008]

MKNKs have been shown to phosphorylate eukaryotic initiation factor 4E (eIF4E), heterogeneous nuclear RNA-binding protein A1 (hnRNP A1), polypyrimidine-tract binding protein-associated splicing factor (PSF), cytoplasmic phospholipase A2 (cPLA2) and Sprouty 2 (hSPRY2) [Buxade M et al., Frontiers in Bioscience 5359-5374, May 1, 2008].

eIF4E is an oncogene that is amplified in many cancers and is phosphorylated exclusively by MKNKs proteins as shown by KO-mouse studies [Konicek et al., Cell Cycle 7:16, 2466-2471, 2008; Ueda et al., Mol Cell Biol 24, 6539-6549, 2004]. eIF4E has a pivotal role in enabling the translation of cellular mRNAs. eIF4E binds the 7-methylguanosine cap at the 5' end of cellular mRNAs and delivers them to the ribosome as part of the eIF4F complex, also containing eIF4G and eIF4A. Though all capped mRNAs require eIF4E for translation, a pool of mRNAs is exceptionally dependent on elevated eIF4E activity for translation. These so-called "weak mRNAs" are usually less efficiently translated due to their long and complex 5'UTR region and they encode proteins that play significant roles in all aspects of malignancy including VEGF, FGF-2, c-Myc, cyclin D1, survivin, BCL-2, MCL-1, MMP-9, heparanase, etc. Expression and function of eIF4E is elevated in multiple human cancers and directly related to disease progression [Konicek et al., Cell Cycle 7:16, 2466-2471, 2008].

MKNK1 and MKNK2 are the only kinases known to phosphorylate eIF4E at Ser209. Overall translation rates are not affected by eIF4E phosphorylation, but it has been suggested that eIF4E phosphorylation contributes to polysome formation (i.e. multiple ribosome on a single mRNA) that ultimately enables more efficient translation of "weak mRNAs" [Buxade M et al., Frontiers in Bioscience 5359-5374, May 1, 2008]. Alternatively, phosphorylation of eIF4E by MKNK proteins might facilitate eIF4E release from the 5' cap so that the 48S complex can move along the "weak mRNA" in order to locate the start codon [Blagden S P and Willis A E, Nat Rev Clin Oncol. 8(5):280-91, 2011]. Accordingly, increased eIF4E phosphorylation predicts poor prognosis in non-small cell lung cancer patients [Yoshizawa et al., Clin Cancer Res. 16(1):240-8, 2010]. Further data point to a functional role of MKNK1 in carcinogenesis, as overexpression of constitutively active MKNK1, but not of kinase-dead MKNK1, in mouse embryo fibroblasts accelerates tumor formation [Chrestensen C. A. et al., Genes Cells 12, 1133-1140, 2007]. Moreover, increased phosphorylation and activity of MKNK proteins correlate with overexpression of HER2 in breast cancer [Chrestensen, C. A. et al., J. Biol. Chem. 282, 4243-4252, 2007]. Constitutively active, but not kinase-dead, MKNK1 also accelerated tumor growth in a model using Eμ-Myc transgenic hematopoietic stem cells to produce tumors in mice. Comparable results were achieved, when an eIF4E carrying a S209D mutation was analyzed. The S209D mutation mimicks a phosphorylation at the MKNK1 phosphorylation site. In contrast a non-phosphorylatable form of eIF4E attenuated tumor growth [Wendel H G, et al., Genes Dev. 21(24):3232-7, 2007]. A selective MKNK inhibitor that blocks eIF4E phosphorylation induces apoptosis and suppresses proliferation and soft agar growth of cancer cells in vitro. This inhibitor also suppresses outgrowth of experimental B16 melanoma pulmonary metastases and growth of subcutaneous HCT116 colon carcinoma xenograft tumors without affecting body weight [Konicek et al., Cancer Res. 71(5):1849-57, 2011]. Screening of a cohort of pancreatic ductal adenocarcinoma patients by immunohistochemistry showed that eIF4E phosphorylation correlated with disease grade, early onset of disease and worse prognosis. In addition it was suggested based on preclinical in vitro findings that the MNK/eIF4E pathway represents an escape route utilized by pancreatic ductal adenocarcinoma cells to withstand chemotherapeutic treatments (e.g Gemcitabine) [Adesso L, et al., Oncogene. 2012 Jul. 16]. Furthermore, it was observed that Rapamycin activated MKNK1 kinase activity in multiple myeloma cell lines and primary specimens by a MKNK-dependent mechanism. Pharmacological inhibition of MKNK activity or genetic silencing of MKNK1 prevented a rapalog-induced upregulation of c-myc IRES activity. Although Rapamycin, used alone, had little effect on myc protein expression, when combined with a MKNK inhibitor, myc protein expression was abrogated. These data provide a rationale for therapeutically targeting MKNK kinases for combined treatment with mTOR inhibitors [Shi Y et al., Oncogene. 2012 Feb. 27]. In summary, eIF4E phosphorylation through MKNK protein activity can promote cellular proliferation and survival and is critical for malignant transformation. Inhibition of MKNK activity may provide a tractable cancer therapeutic approach.

Substituted thiazolo[5,4-d]pyrimidin-7-amines have been disclosed in prior art which may be useful for the treatment or prophylaxis of different diseases:

WO2005/117890(A2) discloses, inter glia, substituted thiazolo[5,4-d]pyrimidin-7-amines for the treatment of C—C chemokine mediated conditions. There is no example of a thiazolo[5,4-d]pyrimidin-7-amine bearing an indazole or benzothiazolone substituent at the 7-amino group.

CN102002044 discloses, inter alia, substituted thiazolo[5,4-d]pyrimidin-7-amines as antitumor agents. There is no example of a thiazolo[5,4-d]pyrimidin-7-amine bearing an indazole or benzothiazolone substituent at the 7-amino group.

EP1731523A1 discloses, inter alia, substituted thiazolo [5,4-d]pyrimidin-7-amines having growth factor receptor tyrosine kinase inhibitory activity. There is no example of a thiazolo[5,4-d]pyrimidin-7-amine bearing an indazole or benzothiazolone substituent at the 7-amino group.

WO2008/005303(A2) and WO2009/078999(A1) disclose, inter alia, TRPV1-modulating thiazolo[5,4-d]pyrimidin-7-amines. There is no example of a thiazolo[5,4-d] pyrimidin-7-amine bearing an indazole or benzothiazolone substituent at the 7-amino group.

WO2008/057402(A2) discloses, inter alia, substituted thiazolo[5,4-d]pyrimidin-7-amines being activiators of the caspase cascade. There is no example of a thiazolo[5,4-d] pyrimidin-7-amine bearing an indazole or benzothiazolone substituent at the 7-amino group.

WO2000/056738(A1) discloses, inter alia, substituted thiazolo[5,4-d]pyrimidin-7-amines and their use as inhibitors of cytokine mediated disease. There is no example of a thiazolo[5,4-d]pyrimidin-7-amine bearing an indazole or benzothiazolone substituent at the 7-amino group.

So, the state of the art described above does not describe the specific substituted thiazolopyrimidine compounds of general formula I of the present invention as defined herein, or a stereoisomer, a tautomer, an N-oxide, a hydrate, a solvate, or a salt thereof, or a mixture of same, as described and defined herein, and as hereinafter referred to as "compounds of the present invention", or their pharmacological activity.

It has now been found, and this constitutes the basis of the present invention, that said compounds of the present invention have surprising and advantageous properties.

In particular, said compounds of the present invention have surprisingly been found to effectively inhibit MKNK kinases and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK kinases, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

SUMMARY OF THE INVENTION

The present invention covers compounds of general formula I:

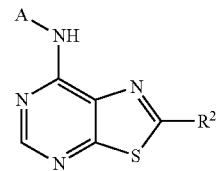

in which:
A represents a group selected from:

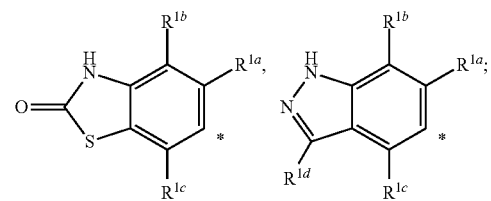

wherein * indicates the point of attachment of said groups with the rest of the molecule;

$R^{1a}$, $R^{1b}$, $R^{1c}$, $R^{1d}$ are the same or different and are independently selected from $R^1$;

$R^1$ represents a hydrogen atom or a halogen atom or a hydroxy-, cyano-, $C_1$-$C_6$-alkyl-, $C_2$-$C_6$-alkenyl-, $C_2$-$C_6$-alkynyl-, $C_1$-$C_6$-alkoxy-, halo-$C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O—, —NR$^{5a}$R$^{5b}$, —SCF$_3$ or —SF$_5$ group;

wherein said $C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O— group is optionally substituted, identically or differently, with 1, 2, 3, 4 or 5 $R^4$ groups;

$R^2$ represents a hydrogen atom, a halogen atom or a group selected from:
$C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl-, heteroaryl-, cyano-, —(CH$_2$)$_q$—X—(CH$_2$)$_p$ —R$^3$;

wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl- or heteroaryl-group is optionally substituted, identically or differently, with 1, 2, 3, 4 or 5 $R^4$ groups;

X represents a bond or a bivalent group selected from:
—O—, —S—, —S(=O)—, —S(=O)$_2$—, —S(=O)—(NR$^{3a}$)—, —(NR$^{3a}$)—S(=O)—, —S(=O)$_2$—(NR$^{3a}$)—, —(NR$^{3a}$)—S(=O)$_2$—, —C(=O)—, —(NR$^{3a}$)—, —C(=O)—O—, —O—C(=O)—, —C(=S)—O—, —O—C(=S)—, —C(=O)—(NR$^{3a}$)—, —(NR$^{3a}$)—C(=O)—, —(NR$^{3a}$)—C(=O)—(NR$^{3b}$)—, —O—C(=O)—(NR$^{3a}$)—, —(NR$^{3a}$)—C(=O)—O—;

$R^{3a}$, $R^{3b}$ are the same or different and are independently selected from $R^3$;

$R^3$ represents a hydrogen atom or a group selected from $C_1$-$C_6$-alkyl-, $C_3$-$C_6$-cycloalkyl-, 3- to 10-membered heterocycloalkyl-, aryl-, heteroaryl-; wherein said $C_1$-$C_6$-alkyl-, $C_3$-$C_6$-cycloalkyl-, 3- to 10-membered heterocycloalkyl-, aryl- or heteroaryl-group is optionally substituted, identically or differently, with 1, 2, 3, 4 or 5 $R^4$ groups;

or $R^3$ together with $R^{3a}$ or $R^{3b}$ represent a 3- to 10-membered heterocycloalkyl- or a 4- to 10-membered heterocycloalkenyl-group, which is optionally substituted, identically or differently, with 1, 2, 3, 4 or 5 $R^4$ groups;

$R^4$ represents halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —C(=O)—$R^5$, —C(=O)—O—$R^5$, —O—C(=O)—$R^5$, —N($R^{5a}$)—C(=O)—$R^{5b}$, —N($R^{5a}$)—C(=O)—$NR^{5b}R^{5c}$, —$NR^{5a}R^{5b}$, —C(=O)—$NR^{5a}R^{5b}$, $R^5$—S—, $R^5$—S(=O)—, $R^5$—S(=O)$_2$—, —N($R^{5a}$)—S(=O)—$R^{5b}$, —S(=O)—$NR^{5a}R^{5b}$, —N($R^{5a}$)—S(=O)$_2$—$R^{5b}$, —S(=O)$_2$—$NR^{5a}R^{5b}$, —S(=O)(=$NR^{5a}$)$R^{5b}$, —S(=O)(=$NR^{5a}$)$R^{5b}$ or —N=S(=O)($R^{5a}$)$R^{5b}$;

$R^{5a}$, $R^{5b}$, $R^{5c}$ are the same or different and are independently selected from $R^5$;

$R^5$ represents a hydrogen atom, a $C_1$-$C_6$-alkyl- or a $C_3$-$C_6$-cycloalkyl-group;

or $R^{5a}$ and $R^{5b}$, or $R^{5a}$ and $R^{5c}$, or $R^{5b}$ and $R^{5c}$ together may form a $C_2$-$C_6$-alkylene group, in which optionally one methylene can be replaced by —O—, —C(=O)—, —NH—, or —N($C_1$-$C_4$-alkyl)-;

p represents an integer of 0, 1, 2 or 3;

q represents an integer of 0, 1, 2 or 3;

or a tautomer, an N-oxide, a hydrate, a solvate, or a salt thereof, or a mixture of same;

The present invention further relates to methods of preparing compounds of general formula I, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

DETAILED DESCRIPTION OF THE INVENTION

The terms as mentioned in the present text have preferably the following meanings:

The term "halogen atom", "halo-" or "Hal-" is to be understood as meaning a fluorine, chlorine, bromine or iodine atom, preferably a fluorine, chlorine or bromine atom.

The term "$C_1$-$C_{10}$-alkyl" is to be understood as preferably meaning a linear or branched, saturated, monovalent hydrocarbon group having 1, 2, 3, 4, 5, 6, 7, 8, 9 or 10 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3, 4, 5 or 6 carbon atoms ("$C_1$-$C_6$-alkyl"), more particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group; even more particularly 1, 2 or 3 carbon atoms ("$C_1$-$C_3$-alkyl"), e.g. a methyl, ethyl, n-propyl- or iso-propyl group.

The term "$C_1$-$C_{10}$-alkylene" is to be understood as preferably meaning a linear or branched, saturated, bivalent hydrocarbon group having 1, 2, 3, 4, 5, 6, 7, 8, 9 or 10 carbon atoms, e.g. a methylene, ethylene, n-propylene, n-butylene, n-pentylene, 2-methylbutylene, n-hexylene, 3-methylpentylene group, or an isomer thereof. Particularly, said group is linear and has 2, 3, 4 or 5 carbon atoms ("$C_2$-$C_5$-alkylene"), e.g. an ethylene, n-propylene, n-butylene, n-pentylene group, more particularly 3 or 4 carbon atoms ("$C_3$-$C_4$-alkylene"), e.g. an n-propylene or n-butylene group.

The term "halo-$C_1$-$C_6$-alkyl" is to be understood as preferably meaning a linear or branched, saturated, monovalent hydrocarbon group in which the term "$C_1$-$C_6$-alkyl" is defined supra, and in which one or more hydrogen atoms is replaced by a halogen atom, in identically or differently, i.e. one halogen atom being independent from another. Particularly, said halogen atom is F. Said halo-$C_1$-$C_6$-alkyl group is, for example, —$CF_3$, —$CHF_2$, —$CH_2F$, —$CF_2CF_3$, or —$CH_2CF_3$.

The term "$C_1$-$C_6$-alkoxy" is to be understood as preferably meaning a linear or branched, saturated, monovalent, hydrocarbon group of formula —O—($C_1$-$C_6$-alkyl), in which the term "$C_1$-$C_6$-alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "halo-$C_1$-$C_6$-alkoxy" is to be understood as preferably meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said halo-$C_1$-$C_6$-alkoxy group is, for example, —$OCF_3$, —$OCHF_2$, —$OCH_2F$, —$OCF_2CF_3$, or —$OCH_2CF_3$.

The term "$C_1$-$C_6$-alkoxy-$C_1$-$C_6$-alkyl" is to be understood as preferably meaning a linear or branched, saturated, monovalent $C_1$-$C_6$-alkyl group, as defined supra, in which one or more of the hydrogen atoms is replaced, in identically or differently, by a $C_1$-$C_6$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group, or an isomer thereof.

The term "halo-$C_1$-$C_6$-alkoxy-$C_1$-$C_6$-alkyl" is to be understood as preferably meaning a linear or branched, saturated, monovalent $C_1$-$C_6$-alkoxy-$C_1$-$C_6$-alkyl group, as defined supra, in which one or more of the hydrogen atoms is replaced, in identically or differently, by a halogen atom. Particularly, said halogen atom is F. Said halo-$C_1$-$C_6$-alkoxy-$C_1$-$C_6$-alkyl group is, for example, —$CH_2CH_2OCF_3$, —$CH_2CH_2OCHF_2$, —$CH_2CH_2OCH_2F$, —$CH_2CH_2OCF_2CF_3$, or —$CH_2CH_2OCH_2CF_3$.

The term "$C_2$-$C_{10}$-alkenyl" is to be understood as preferably meaning a linear or branched, monovalent hydrocarbon group, which contains one or more double bonds, and which has 2, 3, 4, 5, 6, 7, 8, 9 or 10 carbon atoms, particularly 2, 3, 4, 5 or 6 carbon atoms ("$C_2$-$C_6$-alkenyl"), more particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, iso-propenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl)ethenyl, buta-1,3-dienyl, penta-1,4-dienyl, hexa-1,5-dienyl, or methylhexadienyl group. Particularly, said group is vinyl or allyl.

The term "$C_2$-$C_{10}$-alkynyl" is to be understood as preferably meaning a linear or branched, monovalent hydrocarbon group which contains one or more triple bonds, and which contains 2, 3, 4, 5, 6, 7, 8, 9 or 10 carbon atoms, particularly 2, 3, 4, 5 or 6 carbon atoms ("$C_2$-$C_6$-alkynyl"), more particularly 2 or 3 carbon atoms ("$C_2$-$C_3$-alkynyl"). Said $C_2$-$C_{10}$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl, or 3,3-dimethylbut-1-ynyl group. Particularly, said alkynyl group is ethynyl, prop-1-ynyl, or prop-2-ynyl.

The term "$C_3$-$C_{10}$-cycloalkyl" is to be understood as meaning a saturated, monovalent, mono-, or bicyclic hydrocarbon ring which contains 3, 4, 5, 6, 7, 8, 9 or 10 carbon atoms ("$C_3$-$C_{10}$-cycloalkyl"). Said $C_3$-$C_{10}$-cycloalkyl group is for example, a monocyclic hydrocarbon ring, e.g. a cyclopropyl, cyclobutyl, cyclopentyl, cyclohexyl, cycloheptyl, cyclooctyl, cyclononyl or cyclodecyl, or a bicyclic hydrocarbon ring, e.g. a perhydropentalenylene or decalin ring. Particularly, said ring contains 3, 4, 5 or 6 carbon atoms ("$C_3$-$C_6$-cycloalkyl").

The term "$C_3$-$C_6$-cycloalkyloxy" refers to a ($C_3$-$C_6$-cycloalkyl)-O— group in which "$C_3$-$C_6$-cycloalkyl" is as defined herein. Examples include, but are not limited to, cyclopropanoxy and cyclobutanoxy.

The term "$C_4$-$C_{10}$-cycloalkenyl" is to be understood as preferably meaning a non-aromatic, monovalent, mono-, or bicyclic hydrocarbon ring which contains 4, 5, 6, 7, 8, 9 or 10 carbon atoms and one, two, three or four double bonds, in conjugation or not, as the size of said cycloalkenyl ring allows. Said $C_4$-$C_{10}$-cycloalkenyl group is for example, a monocyclic hydrocarbon ring, e.g. a cyclobutenyl, cyclopentenyl, or cyclohexenyl or a bicyclic hydrocarbon, e.g.:

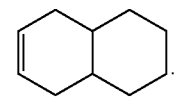

The term "$C_5$-$C_8$-cycloalkenyloxy" refers to a ($C_5$-$C_8$-cycloalkenyl)-O— group in which "$C_5$-$C_8$-cycloalkenyl" is as defined herein.

The term "3- to 10-membered heterocycloalkyl", is to be understood as meaning a saturated, monovalent, mono- or bicyclic hydrocarbon ring which contains 2, 3, 4, 5, 6, 7, 8 or 9 carbon atoms, and one or more heteroatom-containing groups selected from —C(=O)—, —O—, —S—, —S(=O)—, —S(=O)$_2$—, —N(R$^a$)—, in which R$^a$ represents a hydrogen atom or a $C_1$-$C_6$-alkyl-group; it being possible for said heterocycloalkyl group to be attached to the rest of the molecule via any one of the carbon atoms or, if present, the nitrogen atom.

Particularly, said 3- to 10-membered heterocycloalkyl can contain 2, 3, 4, or 5 carbon atoms, and one or more of the above-mentioned heteroatom-containing groups (a "3- to 6-membered heterocycloalkyl"), more particularly said heterocycloalkyl can contain 4 or 5 carbon atoms, and one or more of the above-mentioned heteroatom-containing groups (a "5- to 6-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, pyrrolinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example.

Said heterocycloalkyl can be bicyclic, such as, without being limited thereto, a 5,5-membered ring, e.g. a hexahydrocyclopenta[c]pyrrol-2(1H)-yl ring, or a 5,6-membered bicyclic ring, e.g. a hexahydropyrrolo[1,2-a]pyrazin-2(1H)-yl ring.

The term "4- to 10-membered heterocycloalkenyl", is to be understood as meaning an non-aromatic, unsaturated, monovalent, mono- or bicyclic hydrocarbon ring which contains 3, 4, 5, 6, 7, 8 or 9 carbon atoms, and one or more heteroatom-containing groups selected from —C(=O)—, —O—, —S—, —S(=O)—, —S(=O)$_2$—, —N(R$^a$)—, in which R$^a$ represents a hydrogen atom or a $C_1$-$C_6$-alkyl-group; it being possible for said heterocycloalkenyl group to be attached to the rest of the molecule via any one of the carbon atoms or, if present, the nitrogen atom. Examples of said heterocycloalkenyl are e.g. 4H-pyranyl, 2H-pyranyl, 3H-diazirinyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl, or 4H-[1,4]thiazinyl group.

The term "aryl" is to be understood as preferably meaning a monovalent, aromatic or partially aromatic, mono-, or bi- or tricyclic hydrocarbon ring having 6, 7, 8, 9, 10, 11, 12, 13 or 14 carbon atoms (a "$C_6$-$C_{14}$-aryl" group), particularly a ring having 6 carbon atoms (a "$C_6$-aryl" group), e.g. a phenyl group; or a biphenyl group, or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group, or a ring having 13 carbon atoms, (a "$C_{13}$-aryl" group), e.g. a fluorenyl group, or a ring having 14 carbon atoms, (a "$C_{14}$-aryl" group), e.g. an anthranyl group. Preferably, the aryl group is a phenyl group.

The term "heteroaryl" is understood as preferably meaning a monovalent, monocyclic, bicyclic or tricyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc.

In general, and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

The term "heterocyclic group" includes aromatic or non-aromatic rings, or partially unsaturated ring systems, for example containing from 4 to 20, suitably from 5 to 10 ring atoms, at least one of which is a heteroatom such as oxygen, sulphur or nitrogen. Rings may be mono-, bi- or tri-cylic. Saturated ring systems may also contain bridges, in particular alkyl bridges. Examples of such groups include furyl, thienyl, pyrrolyl, pyrrolidinyl, imidazolyl, thiazolyl, tetrazolyl, oxazolyl, isoxazolyl, pyrazolyl, pyridyl, pyrimidinyl, pyrazinyl, pyridazinyl, triazinyl, quinolinyl, iosquinolinyl, quinoxalinyl, benzthiazolyl, benzoxazolyl, benzothienyl, benzofuranyl, tetrahydrofuryl, chromanyl, benzothienyl, piperidinyl, 1,2,3,4-tetrahydroquinolinyl, 1,2,3,4-tetrahydroisoquinolinyl, pyrazinyl, piperazinyl, pyrimidinyl, pyridazinyl, quinoxalinyl, quinazolinyl, cinnolinyl, indolyl, indolinyl, benzimidazolyl, pyrazolyl, indazolyl, oxazolyl, benzoxazolyl, isoxazolyl, isothiazolyl, morpholinyl, dioxolane, benzodioxolane, 4H-1,4-benzoxazinyl, 4H-1,4-benzothiazinyl, 1,2,3-triazolyl, 1,2,4-triazolyl, oxadiazolyl, furazanyl, thiadiazolyl, dibenzofuranyl, dibenzothienyloxiranyl, oxetanyl, azetidinyl, piperidinyl, oxepanyl, oxazepanyl, tetrahydro-1,4-thiazinyl, 1,1-dioxotetrahydro-1,4-thiazinyl, homopiperidinyl, homopiperazinyl, dihydropyridinyl, tetrahydropyridinyl, dihydropyrimidinyl, tetrahydropyrimidinyl, tetrahydrothienyl, tetrahydrothiopyranyl or thiomorpholinyl.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene) sulfonyloxy, (4-nitro-benzene)sulfonyloxy, (2-nitrobenzene)-sulfonyloxy, (4-isopropyl-benzene)sulfonyloxy, (2,4,6-tri-isopropyl-benzene)-sulfonyloxy, (2,4,6-trimethylbenzene)sulfonyloxy, (4-tertbutyl-benzene)sulfonyloxy, benzenesulfonyloxy, and (4-methoxy-benzene)sulfonyloxy.

As used herein, the term "protective group" is a protective group attached to a nitrogen in intermediates used for the preparation of compounds of the general formula I. Such groups are introduced e.g. by chemical modification of the respective amino group in order to obtain chemoselectivity in a subsequent chemical reaction. Protective groups for amino groups are described for example in T. W. Greene and P. G. M. Wuts in *Protective Groups in Organic Synthesis*, 3rd edition, Wiley 1999; more specifically, said groups can be selected from substituted sulfonyl groups, such as mesyl-, tosyl- or phenylsulfonyl-, acyl groups such as benzoyl, acetyl or tetrahydropyranoyl-, or carbamate based groups, such as tert.-butoxycarbonyl (Boc), or can include silicon, as in e.g. 2-(trimethylsilyl)ethoxymethyl (SEM).

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

The compounds of the present invention may contain sulphur atoms which are asymmetric, such as an asymmetric sulphoxide or sulphoximine group, of structure:

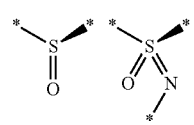

for example, in which * indicates atoms to which the rest of the molecule can be bound.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

Pure stereoisomers can be obtained by resolution of racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R) or (S) isomers, or (E) or (Z) isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

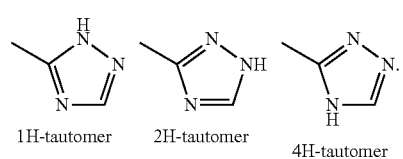

1H-tautomer  2H-tautomer  4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta-etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol, or with a quarternary ammonium salt, such as tetramethylammonium, tetraethylammonium, tetra(n-propyl)ammonium, tetra (n-butyl)ammonium, or N-benzyl-N,N,N-trimethylammonium.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorphs, or as a mixture of more than one polymorphs, in any ratio.

In accordance with a first aspect, the present invention covers compounds of general formula I:

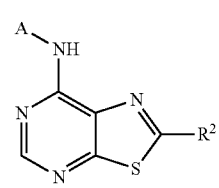

in which:

A represents a group selected from:

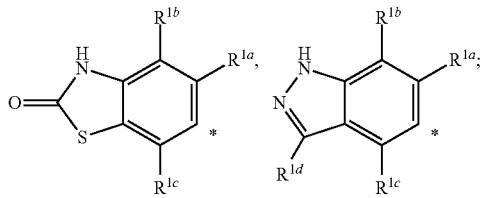

wherein * indicates the point of attachment of said groups with the rest of the molecule;

$R^{1a}$, $R^{1b}$, $R^{1c}$, $R^{1d}$ are the same or different and are independently selected from $R^1$;

$R^1$ represents a hydrogen atom or a halogen atom or a hydroxy-, cyano-, $C_1$-$C_6$-alkyl-, $C_2$-$C_6$-alkenyl-, $C_2$-$C_6$-alkynyl-, $C_1$-$C_6$-alkoxy-, halo-$C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O—, —$NR^{5a}R^{5b}$, —$SCF_3$ or —$SF_5$ group;

wherein said $C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O— group is optionally substituted, identically or differently, with 1, 2, 3, 4 or 5 $R^4$ groups;

$R^2$ represents a hydrogen atom, a halogen atom or a group selected from:

$C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl-, heteroaryl-, cyano-, —$(CH_2)_q$—X—$(CH_2)_p$ —$R^3$;

wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl- or heteroaryl-group is optionally substituted, identically or differently, with 1, 2, 3, 4 or 5 $R^4$ groups;

X represents a bond or a bivalent group selected from: —O—, —S—, —S(=O)—, —S(=O)$_2$—, —S(=O)—$(NR^{3a})$—, —$(NR^{3a})$—S(=O)—, —S(=O)$_2$—$(NR^{3a})$—, —$(NR^{3a})$—S(=O)$_2$—, —C(=O)—, —$(NR^{3a})$—, —C(=O)—O—, —O—C(=O)—, —C(=S)—O—, —O—C(=S)—, —C(=O)—$(NR^{3a})$—, —$(NR^{3a})$—C(=O)—, —$(NR^{3a})$—C(=O)—$(NR^{3b})$—, —O—C(=O)—$(NR^{3a})$—, —$(NR^{3a})$—C(=O)—O—;

$R^{3a}$, $R^{3b}$ are the same or different and are independently selected from $R^3$;

$R^3$ represents a hydrogen atom or a group selected from $C_1$-$C_6$-alkyl-, $C_3$-$C_6$-cycloalkyl-, 3- to 10-membered heterocycloalkyl-, aryl-, heteroaryl-; wherein said $C_1$-$C_6$-alkyl-, $C_3$-$C_6$-cycloalkyl-, 3- to 10-membered heterocycloalkyl-, aryl- or heteroaryl-group is optionally substituted, identically or differently, with 1, 2, 3, 4 or 5 $R^4$ groups;

or $R^3$ together with $R^{3a}$ or $R^{3b}$ represent a 3- to 10-membered heterocycloalkyl- or a 4- to 10-membered heterocycloalkenyl-group, which is optionally substituted, identically or differently, with 1, 2, 3, 4 or 5 $R^4$ groups;

$R^4$ represents halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —C(=O)—$R^5$, —C(=O)—O—$R^5$, —O—C(=O)—$R^5$, —$N(R^{5a})$—C(=O)—$R^{5b}$, —$N(R^{5a})$—C(=O)—$NR^{5b}R^{5c}$, —$NR^{5a}R^{5b}$, —C(=O)—$NR^{5a}R^{5b}$, $R^5$—S—, $R^5$—S(=O)—, $R^5$—S(=O)$_2$—, —$N(R^{5a})$—S(=O)—$R^{5b}$, —S(=O)—$NR^{5a}R^{5b}$, —$N(R^{5a})$—S(=O)$_2$—$R^{5b}$, —S(=O)$_2$—$NR^{5a}R^{5b}$, —S(=O)(=$NR^{5a}$)$R^{5b}$, —S(=O)(=$NR^{5a}$)$R^{5b}$ or —N=S(=O)($R^{5a}$)$R^{5b}$;

$R^{5a}$, $R^{5b}$, $R^{5c}$ are the same or different and are independently selected from $R^5$;

$R^5$ represents a hydrogen atom, a $C_1$-$C_6$-alkyl- or a $C_3$-$C_6$-cycloalkyl-group;

or $R^{5a}$ and $R^{5b}$, or $R^{5a}$ and $R^{5c}$, or $R^{5b}$ and $R^{5c}$ together may form a $C_2$-$C_6$-alkylene group, in which optionally one methylene can be replaced by —O—, —C(=O)—, —NH—, or —N($C_1$-$C_4$-alkyl)-;

p represents an integer of 0, 1, 2 or 3;

q represents an integer of 0, 1, 2 or 3;

or a tautomer, an N-oxide, a hydrate, a solvate, or a salt thereof, or a mixture of same.

In a preferred embodiment, the invention relates to compounds of formula I, supra, wherein A represents:

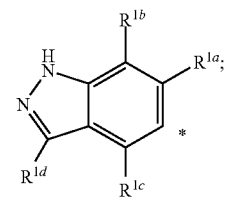

wherein * indicates the point of attachment of said group with the rest of the molecule.

In another preferred embodiment, the invention relates to compounds of formula I, supra, wherein A represents:

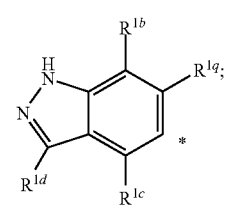

wherein * indicates the point of attachment of said groups with the rest of the molecule.

In another preferred embodiment, the invention relates to compounds of formula I, supra, wherein A represents:

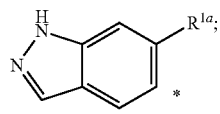

wherein * indicates the point of attachment of said group with the rest of the molecule.

In another preferred embodiment, the invention relates to compounds of formula I, supra, wherein A represents:

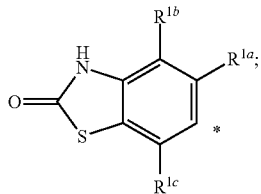

wherein * indicates the point of attachment of said group with the rest of the molecule.

In another preferred embodiment, the invention relates to compounds of formula I, supra, wherein A represents:

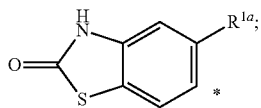

wherein * indicates the point of attachment of said group with the rest of the molecule.

In another preferred embodiment, the invention relates to compounds of formula I, supra, wherein A represents:

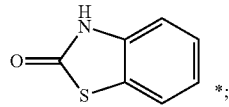

wherein * indicates the point of attachment of said group with the rest of the molecule.

In another preferred embodiment, the invention relates to compounds of formula I, supra, wherein $R^{1a}$ represents a hydrogen atom.

In another preferred embodiment, the invention relates to compounds of formula I, supra, wherein $R^{1a}$ represents a group selected from: $C_1$-$C_3$-alkyl-, $C_1$-$C_3$-alkoxy-, halo-.

In another preferred embodiment, the invention relates to compounds of formula I, supra, wherein $R^{1a}$ represents a group selected from: $C_1$-$C_3$-alkoxy-, halo-.

In another preferred embodiment, the invention relates to compounds of formula I, supra, wherein $R^{1a}$ represents a $C_1$-$C_3$-alkoxy-group, preferably a methoxy-group.

In another preferred embodiment, the invention relates to compounds of formula I, supra, wherein $R^{1b}$ represents a hydrogen atom.

In another preferred embodiment, the invention relates to compounds of formula I, supra, wherein $R^{1c}$ represents a hydrogen atom.

In another preferred embodiment, the invention relates to compounds of formula I, supra, wherein each of $R^{1b}$ and $R^{1c}$ represents a hydrogen atom.

In another preferred embodiment, the invention relates to compounds of formula I, supra, wherein each of $R^{1b}$, $R^{1c}$, and $R^{1d}$ represents a hydrogen atom.

In another preferred embodiment, the invention relates to compounds of formula I, supra, wherein each of $R^{1b}$, $R^{1c}$, and $R^{1d}$ represents a hydrogen atom; and $R^{1a}$ represents a group selected from: $C_1$-$C_3$-alkoxy-, halo-.

In another preferred embodiment, the invention relates to compounds of formula I, supra, wherein each of $R^{1b}$, $R^{1c}$, and $R^{1d}$ represents a hydrogen atom; and $R^{1a}$ represents a $C_1$-$C_3$-alkoxy-group.

In another preferred embodiment, the invention relates to compounds of formula I, supra, wherein $R^{1q}$ represents a halogen atom or a hydroxy-, cyano-, $C_1$-$C_6$-alkyl-, halo-$C_1$-$C_6$-alkyl-, $C_2$-$C_6$-alkenyl-, $C_2$-$C_6$-alkynyl-, $C_1$-$C_6$-alkoxy-, halo-$C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O—, —$NR^{5a}R^{5b}$, —$SCF_3$ or —$SF_5$ group; wherein said $C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O— group is optionally substituted, identically or differently, with 1, 2, 3, 4 or 5 $R^4$ groups.

In another preferred embodiment, the invention relates to compounds of formula I, supra, wherein $R^{1q}$ represents a hydrogen atom or a group selected from:
$C_1$-$C_3$-alkyl-, $C_1$-$C_3$-alkoxy-, halo-.

In another preferred embodiment, the invention relates to compounds of formula I, supra, wherein each of $R^{1b}$, $R^{1c}$, and $R^{1d}$ represents a hydrogen atom; and $R^{1q}$ represents a group selected from: $C_1$-$C_3$-alkyl-, $C_1$-$C_3$-alkoxy-, halo-.

In another preferred embodiment, the invention relates to compounds of formula I, supra, wherein $R^2$ represents a group selected from: $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, aryl-, —$(CH_2)_q$—X—$(CH_2)_p$—$R^3$; wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl- or aryl-group is optionally substituted, identically or differently, with 1, 2 or 3 $R^4$ groups.

In another preferred embodiment, the invention relates to compounds of formula I, supra, wherein $R^2$ represents a hydrogen atom, a halogen atom, or a group selected from: $C_1$-$C_6$-alkyl-, $C_3$-$C_6$-cycloalkyl-, aryl-, cyano-, —$(CH_2)_q$—X—$(CH_2)_p$—$R^3$;

wherein said $C_1$-$C_6$-alkyl-, $C_3$-$C_6$-cycloalkyl- or aryl-group is optionally substituted, identically or differently, with 1, 2 or 3 $R^4$ groups;

In another preferred embodiment, the invention relates to compounds of formula I, supra, wherein $R^2$ represents a hydrogen atom or a group selected from:
$C_1$-$C_6$-alkyl-, $C_3$-$C_6$-cycloalkyl-, —$(CH_2)_q$—X—$(CH_2)_p$—$R^3$;

wherein said $C_1$-$C_6$-alkyl- or $C_3$-$C_6$-cycloalkyl-group is optionally substituted, identically or differently, with 1, 2 or 3 $R^4$ groups;

In another preferred embodiment, the invention relates to compounds of formula I, supra, wherein $R^2$ represents a group selected from:
$C_3$-$C_6$-cycloalkyl-, —$(CH_2)_q$—($C_3$-$C_6$-cycloalkyl), —$(CH_2)_q$-(aryl); wherein q=1.

In another preferred embodiment, the invention relates to compounds of formula I, supra, wherein $R^2$ represents: —$(CH_2)_q$—X—$(CH_2)_p$—$R^3$.

In another preferred embodiment, the invention relates to compounds of formula I, supra, wherein $R^2$ represents a $C_1$-$C_6$-alkyl-group; wherein said $C_1$-$C_6$-alkyl-group is optionally substituted, identically or differently, with 1, 2 or 3 $R^4$ groups.

In another preferred embodiment, the invention relates to compounds of formula I, supra, wherein A is not

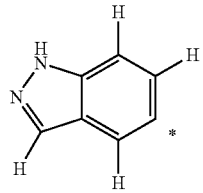

when $R^2$ is

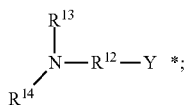

in which:

Y is a direct bond or a group selected from:
—O—, —C(=O)—, —S(=O)$_m$—, —N($R^{18}$)—, —N($R^{18}$)C(=O)—, —C(=O)N($R^{18}$)—, —S(=O)$_m$N ($R^{18}$)—;

$R^{12}$ is a direct bond, an optionally substituted, straight or branched $C_1$-$C_{10}$-alkylene group, which is optionally interposed with a group N($R^{15}$) where $R^{15}$ is hydrogen or a $C_1$-$C_3$-alkyl group;

$R^{13}$ and $R^{14}$ are independently selected from an optionally substituted $C_1$-$C_{10}$-alkyl-group, an optionally substituted $C_2$-$C_{10}$-alkenyl-group, an optionally substituted $C_2$-$C_{10}$-alkynyl-group or an optionally substituted heterocyclic group;

$R^{18}$ is hydrogen or an optionally substituted $C_1$-$C_4$-alkyl-group;

m is 0, 1 or 2;

* indicates the point of attachment of said groups with the rest of the molecule;

or $R^{13}$ and $R^{14}$ together with the nitrogen atom to which they are attached form an optionally substituted heterocyclic ring, which optionally contains additional heteroatoms;

or $R^{13}$ together with $R^{12}$ or $R^{18}$ and the nitrogen atom(s) to which they are attached form an optionally substituted heterocyclic ring which optionally contains additional heteroatoms;

or $R^{13}$ and $R^{14}$ together with $R^{12}$ form an optionally substituted bridged ring structure;

or $R^{12}$ together with $R^{18}$ may form an optionally substituted cycloalkyl or heterocyclic ring.

In another preferred embodiment, the invention relates to compounds of formula I, supra, wherein $R^2$ is not

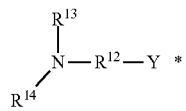

wherein * indicates the point of attachment of said group with the rest of the molecule; and in which:

Y is a direct bond or a group selected from:
—O—, —C(=O)—, —S(=O)$_m$—, —N($R^{18}$)—, —N($R^{18}$)C(=O)—, —C(=O)N($R^{18}$)—, —S(=O)$_m$N ($R^{18}$)—;

$R^{12}$ is a direct bond, an optionally substituted, straight or branched $C_1$-$C_{10}$-alkylene group, which is optionally interposed with a group N($R^{15}$) where $R^{15}$ is hydrogen or a $C_1$-$C_3$-alkyl group;

$R^{13}$ and $R^{14}$ are independently selected from an optionally substituted $C_1$-$C_{10}$-alkyl-group, an optionally substituted $C_2$-$C_{10}$-alkenyl-group, an optionally substituted $C_2$-$C_{10}$-alkynyl-group or an optionally substituted heterocyclic group;

$R^{18}$ is hydrogen or an optionally substituted $C_1$-$C_4$-alkyl-group;

m is 0, 1 or 2;

or $R^{13}$ and $R^{14}$ together with the nitrogen atom to which they are attached form an optionally substituted heterocyclic ring, which optionally contains additional heteroatoms;

or $R^{13}$ together with $R^{12}$ or $R^{18}$ and the nitrogen atom(s) to which they are attached form an optionally substituted heterocyclic ring which optionally contains additional heteroatoms;

or $R^{13}$ and $R^{14}$ together with $R^{12}$ form an optionally substituted bridged ring structure.

In another preferred embodiment, the invention relates to compounds of formula I, supra, wherein $R^2$ does not contain a nitrogen atom.

In another preferred embodiment $R^2$ represents a hydrogen atom or a halogen atom or a group selected from: $C_1$-$C_3$-alkyl-, —$(CH_2)_q$—X—$(CH_2)_p$—$R^3$; wherein said $C_1$-$C_3$-alkyl-group is optionally substituted, identically or differently, with 1, 2 or 3 $R^4$ groups.

In another preferred embodiment $R^2$ represents a 4- to 6-membered heterocycloalkyl- or 4- to 6-membered heterocycloalkenyl-group, wherein said 4- to 6-membered heterocycloalkyl- or 4- to 6-membered heterocycloalkenyl-group is optionally substituted, identically or differently, with 1, 2 or 3 $R^4$ groups.

In another preferred embodiment $R^2$ represents a group selected from: $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, aryl-, —$(CH_2)_q$—($C_3$-$C_6$-cycloalkyl), —$(CH_2)_q$-(aryl); wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, aryl-, —$(CH_2)_q$—($C_3$-$C_6$-cycloalkyl) or —$(CH_2)_q$-(aryl) group is optionally substituted, identically or differently, with 1, 2 or 3 $R^4$ groups.

In another preferred embodiment $R^2$ represents a hydrogen atom or a group selected from: $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, aryl-, —$(CH_2)_q$—($C_3$-$C_6$-cycloalkyl), —$(CH_2)_q$-(aryl); wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, aryl-, —$(CH_2)_q$—($C_3$-$C_6$-cycloalkyl) or —$(CH_2)_q$-(aryl) group is optionally substituted, identically or differently, with 1, 2 or 3 $R^4$ groups.

In another preferred embodiment X represents a bond or a bivalent group selected from: —S(=O)$_2$—, —C(=O)—O—, —C(=O)—(NR$^{3a}$)—.

In another preferred embodiment X represents a bond or a bivalent group selected from: —O—, —C(=O)—, —C(=O)—(NR$^{3a}$)—, —(NR$^{3a}$)—C(=O)—.

In another preferred embodiment X represents a bond.

In another preferred embodiment X represents a bivalent group selected from:
—S—, —S(=O)—, —S(=O)$_2$—.

In another preferred embodiment X represents —S(=O)$_2$—.

In another preferred embodiment X represents —O—.

In another preferred embodiment X represents a bivalent group selected from:
—S(=O)—(NR$^{3a}$)—, —(NR$^{3a}$)—S(=O)—.

In another preferred embodiment X represents a bivalent group selected from:
—S(=O)$_2$—(NR$^{3a}$)—, —(NR$^{3a}$)—S(=O)$_2$—.

In another preferred embodiment X represents a bivalent group selected from:
—O—C(=O)—, —C(=S)—O—, —O—C(=S)—.

In another preferred embodiment X represents —(NR$^{3a}$)—.

In another preferred embodiment X represents a bivalent group selected from:
—C(=O)—, —C(=O)—O—, —C(=O)—(NR$^{3a}$)—, —(NR$^{3a}$)—C(=O)—, —(NR$^{3a}$)—C(=O)—(NR$^{3b}$)—, —O—C(=O)—(NR$^{3a}$)—, —(NR$^{3a}$)—C(=O)—O—.

In another preferred embodiment X represents a bivalent group selected from:
—(NR$^{3a}$)—C(=O)—(NR$^{3b}$)—, —O—C(=O)—(NR$^{3a}$)—, —(NR$^{3a}$)—C(=O)—O—.

In another preferred embodiment X represents a bivalent group selected from:
—C(=O)—, —C(=O)—O—, —C(=O)—(NR$^{3a}$)—, —(NR$^{3a}$)—C(=O)—.

In another preferred embodiment X represents a bivalent group selected from:
—C(=O)—, —C(=O)—O—, —C(=O)—(NR$^{3a}$)—.

In another preferred embodiment X represents a bivalent group selected from:
C(=O)—, —C(=O)—O—, —C(=O)—(NR$^{3a}$)— with the proviso that if X=—C(=O)— and both p and q are 0, then R$^3$ is not an aryl-group.

In another preferred embodiment X represents a bivalent group selected from:
—C(=O)—O—, —C(=O)—(NR$^{3a}$)—.

In another preferred embodiment X represents —C(=O)—.

In another preferred embodiment X represents —C(=O)—O—.

In another preferred embodiment X represents —O—C(=O)—.

In another preferred embodiment X represents —C(=O)—(NR$^{3a}$)—.

In another preferred embodiment X represents —(NR$^{3a}$)—C(=O)—.

In another preferred embodiment R$^3$ represents a hydrogen atom or a group selected from C$_1$-C$_6$-alkyl-, C$_3$-C$_6$-cycloalkyl-, 3- to 10-membered heterocycloalkyl-, aryl-, heteroaryl-, halo-C$_1$-C$_3$-alkyl-; wherein said C$_1$-C$_6$-alkyl-, C$_3$-C$_6$-cycloalkyl-, 3- to 10-membered heterocycloalkyl-, aryl- or heteroaryl-group is optionally substituted, identically or differently, with 1, 2 or 3 R$^4$ groups.

In another preferred embodiment R$^3$ represents a hydrogen atom or a group selected from C$_1$-C$_6$-alkyl-, C$_3$-C$_6$-cycloalkyl-, 3- to 10-membered heterocycloalkyl-, aryl-; wherein said C$_1$-C$_6$-alkyl-, C$_3$-C$_6$-cycloalkyl-, 3- to 10-membered heterocycloalkyl- or aryl-group is optionally substituted, identically or differently, with 1, 2 or 3 R$^4$ groups.

In another preferred embodiment R$^3$ represents a hydrogen atom or a group selected from C$_1$-C$_6$-alkyl-, C$_3$-C$_6$-cycloalkyl-, 3- to 10-membered heterocycloalkyl-, halo-C$_1$-C$_3$-alkyl-; wherein said C$_1$-C$_6$-alkyl-, C$_3$-C$_6$-cycloalkyl- or 3- to 10-membered heterocycloalkyl-group is optionally substituted, identically or differently, with 1, 2 or 3 R$^4$ groups.

In another preferred embodiment R$^3$ represents a hydrogen atom or a group selected from C$_1$-C$_3$-alkyl-, C$_3$-C$_6$-cycloalkyl-, 4- to 6-membered heterocycloalkyl-, halo-C$_1$-C$_3$-alkyl-; wherein said C$_1$-C$_3$-alkyl-, C$_3$-C$_6$-cycloalkyl- or 4- to 6-membered heterocycloalkyl-group is optionally substituted, identically or differently, with 1, 2 or 3 R$^4$ groups.

In another preferred embodiment R$^3$ represents a hydrogen atom or a group selected from C$_1$-C$_3$-alkyl-, 4- to 6-membered heterocycloalkyl-; wherein said C$_1$-C$_3$-alkyl- or 4- to 6-membered heterocycloalkyl-group is optionally substituted, identically or differently, with 1, 2 or 3 R$^4$ groups.

In another preferred embodiment R$^3$ represents a hydrogen atom or a group selected from C$_1$-C$_3$-alkyl-, 4- to 6-membered heterocycloalkyl-; wherein said C$_1$-C$_3$-alkyl- or 4- to 6-membered with one R$^4$ group.

In another preferred embodiment R$^3$ represents a hydrogen atom or a group selected from C$_1$-C$_3$-alkyl-, 4- to 6-membered heterocycloalkyl-; wherein said C$_1$-C$_3$-alkyl- or 4- to 6-membered heterocycloalkyl-groups are optionally substituted with one R$^4$ group.

In another preferred embodiment R$^3$ represents a hydrogen atom or a group selected from: C$_1$-C$_6$-alkyl-, C$_3$-C$_6$-cycloalkyl-, 3- to 10-membered heterocycloalkyl-, aryl-; said groups being optionally substituted, identically or differently, with 1, 2 or 3 R$^4$ groups.

In another preferred embodiment R$^3$ represents a hydrogen atom or a group selected from: C$_1$-C$_6$-alkyl-, aryl-; said groups being optionally substituted, identically or differently, with 1, 2 or 3 R$^4$ groups.

In another preferred embodiment R$^{3a}$ represents a hydrogen atom or a group selected from C$_1$-C$_3$-alkyl-, C$_3$-C$_6$-cycloalkyl-, 4- to 6-membered heterocycloalkyl-, aryl-, heteroaryl-, halo-C$_1$-C$_3$-alkyl-; wherein said C$_1$-C$_3$-alkyl-, C$_3$-C$_6$-cycloalkyl-, 4- to 6-membered heterocycloalkyl-, aryl- or heteroaryl-group is optionally substituted, identically or differently, with 1, 2, 3, 4 or 5 R$^4$ groups.

In another preferred embodiment R$^{3a}$ represents a hydrogen atom or a group selected from C$_1$-C$_3$-alkyl-, C$_3$-C$_6$-cycloalkyl-, 4- to 6-membered heterocycloalkyl-, halo-C$_1$-C$_3$-alkyl-; wherein said C$_1$-C$_3$-alkyl-, C$_3$-C$_6$-cycloalkyl- or 4- to 6-membered heterocycloalkyl-group is optionally substituted, identically or differently, with 1, 2 or 3 R$^4$ groups.

In another preferred embodiment R$^{3a}$ represents a hydrogen atom or a C$_1$-C$_6$-alkyl-group; wherein said C$_1$-C$_6$-alkyl-group is optionally substituted, identically or differently, with 1, 2 or 3 R$^4$ groups.

In another preferred embodiment R$^{3a}$ represents a hydrogen atom or a C$_1$-C$_6$-alkyl-group; wherein said C$_1$-C$_6$-alkyl-group is optionally substituted, identically or differently, with 1 or 2 R$^4$ groups.

In another preferred embodiment R$^{3a}$ represents a hydrogen atom or a C$_1$-C$_3$-alkyl-group; wherein said C$_1$-C$_3$-alkyl-group is optionally substituted, identically or differently, with 1 or 2 R$^4$ groups.

In another preferred embodiment $R^{3a}$ represents a hydrogen atom or a $C_1$-$C_3$-alkyl-group; wherein said $C_1$-$C_3$-alkyl-group is optionally substituted with one $R^4$ group.

In another preferred embodiment $R^{3a}$ represents a hydrogen atom or a $C_1$-$C_3$-alkyl-group.

In another preferred embodiment $R^{3a}$ represents a hydrogen atom.

In another preferred embodiment $R^{3b}$ represents a hydrogen atom or a group selected from $C_1$-$C_3$-alkyl-, $C_3$-$C_6$-cycloalkyl-, 4- to 6-membered heterocycloalkyl-, aryl-, heteroaryl-, halo-$C_1$-$C_3$-alkyl-; wherein said $C_1$-$C_3$-alkyl-, $C_3$-$C_6$-cycloalkyl-, 4- to 6-membered heterocycloalkyl-, aryl- or heteroaryl-group is optionally substituted, identically or differently, with 1, 2, 3, 4 or 5 $R^4$ groups.

In another preferred embodiment $R^{3b}$ represents a hydrogen atom or a group selected from $C_1$-$C_3$-alkyl-, $C_3$-$C_6$-cycloalkyl-, 4- to 6-membered heterocycloalkyl-, halo-$C_1$-$C_3$-alkyl-; wherein said $C_1$-$C_3$-alkyl-, $C_3$-$C_6$-cycloalkyl- or 4- to 6-membered heterocycloalkyl-group is optionally substituted, identically or differently, with 1, 2 or 3 $R^4$ groups.

In another preferred embodiment $R^{3b}$ represents a hydrogen atom or a $C_1$-$C_6$-alkyl-group; wherein said $C_1$-$C_6$-alkyl-group is optionally substituted, identically or differently, with 1, 2 or 3 $R^4$ groups.

In another preferred embodiment $R^{3b}$ represents a hydrogen atom or a $C_1$-$C_6$-alkyl-group; wherein said $C_1$-$C_6$-alkyl-group is optionally substituted, identically or differently, with 1 or 2 $R^4$ groups.

In another preferred embodiment $R^{3b}$ represents a hydrogen atom or a $C_1$-$C_3$-alkyl-group; wherein said $C_1$-$C_3$-alkyl-group is optionally substituted, identically or differently, with 1 or 2 $R^4$ groups.

In another preferred embodiment $R^{3b}$ represents a hydrogen atom or a $C_1$-$C_3$-alkyl-group; wherein said $C_1$-$C_3$-alkyl-group is optionally substituted with one $R^4$ group.

In another preferred embodiment $R^{3b}$ represents a hydrogen atom or a $C_1$-$C_3$-alkyl-group.

In another preferred embodiment $R^{3b}$ represents a hydrogen atom.

In another preferred embodiment $R^3$ together with $R^{3a}$ or $R^{3b}$ represent a 3- to 10-membered heterocycloalkyl- or a 4- to 10-membered heterocycloalkenyl-group, which is optionally substituted, one or more times, identically or differently, with halo-, hydroxyl-, cyano-.

In another preferred embodiment $R^3$ together with $R^{3a}$ represent a 3- to 10-membered heterocycloalkyl- or a 4- to 10-membered heterocycloalkenyl-group, which is optionally substituted, one or more times, identically or differently, with halo-, hydroxyl-, cyano-.

In another preferred embodiment $R^3$ together with $R^{3a}$ or $R^{3b}$ represent a 3- to 10-membered heterocycloalkyl-group, which is optionally substituted, one or more times, identically or differently, with halo-, hydroxyl-, cyano-.

In another preferred embodiment $R^3$ together with $R^{3a}$ or $R^{3b}$ represent a 3- to 10-membered heterocycloalkyl-group, which is optionally substituted, one or more times, identically or differently, with halo-.

In another preferred embodiment $R^3$ together with $R^{3a}$ represent a 3- to 10-membered heterocycloalkyl-group, which is optionally substituted, one or more times, identically or differently, with halo-.

In another preferred embodiment $R^4$ represents halo-, hydroxy-, cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl- or halo-$C_1$-$C_6$-alkoxy-$C_1$-$C_6$-alkyl-.

In another preferred embodiment $R^4$ represents halo-, hydroxy-, cyano-, nitro-, $C_1$-$C_3$-alkyl-, $C_2$-$C_3$-alkenyl-, $C_2$-$C_3$-alkynyl-, halo-$C_1$-$C_3$-alkyl-, $C_1$-$C_3$-alkoxy-, halo-$C_1$-$C_3$-alkoxy-, hydroxy-$C_1$-$C_3$-alkyl-, $C_1$-$C_3$-alkoxy-$C_1$-$C_3$-alkyl- or halo-$C_1$-$C_3$-alkoxy-$C_1$-$C_3$-alkyl-.

In another preferred embodiment $R^4$ represents halo-, hydroxy-, $C_1$-$C_3$-alkyl-, $C_2$-$C_3$-alkenyl-, $C_2$-$C_3$-alkynyl-, halo-$C_1$-$C_3$-alkyl-, $C_1$-$C_3$-alkoxy-, halo-$C_1$-$C_3$-alkoxy-, hydroxy-$C_1$-$C_3$-alkyl-, $C_1$-$C_3$-alkoxy-$C_1$-$C_3$-alkyl- or halo-$C_1$-$C_3$-alkoxy-$C_1$-$C_3$-alkyl-.

In another preferred embodiment $R^4$ represents halo-, $C_1$-$C_3$-alkyl-, $C_2$-$C_3$-alkenyl-, $C_2$-$C_3$-alkynyl-, halo-$C_1$-$C_3$-alkyl-, $C_1$-$C_3$-alkoxy-, halo-$C_1$-$C_3$-alkoxy-, $C_1$-$C_3$-alkoxy-$C_1$-$C_3$-alkyl- or halo-$C_1$-$C_3$-alkoxy-$C_1$-$C_3$-alkyl-.

In another preferred embodiment $R^4$ represents halo-, $C_1$-$C_3$-alkyl-, halo-$C_1$-$C_3$-alkyl-, $C_1$-$C_3$-alkoxy- or halo-$C_1$-$C_3$-alkoxy-.

In another preferred embodiment $R^4$ represents $C_1$-$C_3$-alkyl-.

In another preferred embodiment $R^4$ represents $R^5$—O—, —C(=O)—$R^5$, —O—C(=O)—$R^5$, —C(=O)—O—$R^5$, —N($R^{5a}$)—C(=O)—$R^{5b}$, —N($R^{5a}$)—C(=O)—N$R^{5b}R^{5c}$, —N$R^{5a}R^{5b}$, —C(=O)—N$R^{5a}R^{5b}$, $R^5$—S—, $R^5$—S(=O)—, $R^5$—S(=O)$_2$—, —N($R^{5a}$)—S(=O)—$R^{5b}$, —S(=O)—N$R^{5a}R^{5b}$, —N($R^{5a}$)—S(=O)$_2$—$R^{5b}$, —S(=O)$_2$—N$R^{5a}R^{5b}$, —S(=O)(=N$R^{5a}$)$R^{5b}$, —S(=O)(=N$R^{5a}$)$R^{5b}$ or —N=S(=O)($R^{5a}$)$R^{5b}$.

In another preferred embodiment $R^4$ represents $R^5$—O—, —C(=O)—$R^5$, —O—C(=O)—$R^5$ or —C(=O)—O—$R^5$.

In another preferred embodiment $R^4$ represents —N($R^{5a}$)—C(=O)—$R^{5b}$, —N($R^{5a}$)—C(=O)—N$R^{5b}R^{5c}$, —N$R^{5a}R^{5b}$ or —C(=O)—N$R^{5a}R^{5b}$.

In another preferred embodiment $R^4$ represents $R^5$—S—, $R^5$—S(=O)— or $R^5$—S(=O)$_2$—.

In another preferred embodiment $R^4$ represents —N($R^{5a}$)—S(=O)—$R^{5b}$, —S(=O)—N$R^{5a}R^{5b}$, —N($R^{5a}$)—S(=O)$_2$—$R^{5b}$, —S(=O)$_2$—N$R^{5a}R^{5b}$, —S(=O)(=N$R^{5a}$)$R^{5b}$, —S(=O)(=N$R^{5a}$)$R^{5b}$ or —N=S(=O)($R^{5a}$)$R^{5b}$.

In another preferred embodiment $R^4$ represents $R^5$—S(=O)—, $R^5$—S(=O)$_2$—, —C(=O)—$R^5$, —O—C(=O)—$R^5$, —C(=O)—O—$R^5$, —N($R^{5a}$)—C(=O)—$R^{5b}$, —N$R^{5a}R^{5b}$ or —C(=O)—N$R^{5a}R^{5b}$.

In another preferred embodiment $R^4$ represents halo-, hydroxy- or —N$R^{5a}R^{5b}$.

In another preferred embodiment $R^4$ represents halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —C(=O)—$R^5$, —C(=O)—O—$R^5$ or —O—C(=O)—$R^5$.

In another preferred embodiment $R^4$ represents halo-, hydroxy-, oxo-(O=), cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, $R^5$—O—, —C(=O)—$R^5$, —C(=O)—O—$R^5$, —O—C(=O)—$R^5$ or —C(=O)—N$R^{5a}R^{5b}$.

In another preferred embodiment $R^4$ represents halo-, hydroxy-, oxo-(O=), cyano-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, —C(=O)—$R^5$, —C(=O)—O—$R^5$, —O—C(=O)—$R^5$ or —C(=O)—N$R^{5a}R^{5b}$.

In another preferred embodiment $R^4$ represents halo-, hydroxy-, oxo-(O=), cyano-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, —C(=O)—$R^5$ or —C(=O)—N$R^{5a}R^{5b}$.

In another preferred embodiment $R^5$ represents a hydrogen atom or a $C_1$-$C_6$-alkyl-group.

In another preferred embodiment $R^5$ represents a hydrogen atom or a $C_1$-$C_3$-alkyl-group.

In another preferred embodiment $R^{5a}$ represents a hydrogen atom or a $C_1$-$C_6$-alkyl-group.

In another preferred embodiment $R^{5a}$ represents a hydrogen atom or a $C_1$-$C_3$-alkyl-group.

In another preferred embodiment $R^{5b}$ represents a hydrogen atom or a $C_1$-$C_6$-alkyl-group.

In another preferred embodiment $R^{5b}$ represents a hydrogen atom or a $C_1$-$C_3$-alkyl-group.

In another preferred embodiment $R^{5c}$ represents a hydrogen atom or a $C_1$-$C_6$-alkyl-group.

In another preferred embodiment $R^{5c}$ represents a hydrogen atom or a $C_1$-$C_3$-alkyl-group.

In another preferred embodiment
$R^{5a}$ and $R^{5b}$, or
$R^{5a}$ and $R^{5c}$, or
$R^{5b}$ and $R^{5c}$
together form a $C_2$-$C_6$-alkylene group, in which optionally one methylene is replaced by —O—, —C(=O)—, —NH—, or —N($C_1$-$C_4$-alkyl)-.

In another preferred embodiment $R^{5a}$ and $R^{5b}$ together form a $C_3$-$C_4$ alkylene group.

In another preferred embodiment $R^{5a}$ and $R^{5c}$ together form a $C_3$-$C_4$ alkylene group.

In another preferred embodiment $R^{5b}$ and $R^{5c}$ together form a $C_3$-$C_4$ alkylene group.

In another preferred embodiment p represents an integer of 0, 1 or 2.

In another preferred embodiment p represents an integer of 0 or 1.

In another preferred embodiment p represents an integer of 0.

In another preferred embodiment p represents an integer of 1.

In another preferred embodiment p represents an integer of 2.

In another preferred embodiment q represents an integer of 0, 1 or 2.

In another preferred embodiment q represents an integer of 0.

In another preferred embodiment q represents an integer of 1.

In another preferred embodiment q represents an integer of 2.

In another preferred embodiment p represents an integer of 0 or 1 and q represents an integer of 0, 1, 2 or 3.

In another preferred embodiment p represents an integer of 0 and q represents an integer of 1.

In another preferred embodiment p represents an integer of 1 and q represents an integer of 0.

In another preferred embodiment p represents an integer of 0 and q represents an integer of 0.

In another preferred embodiment p represents an integer of 1 and q represents an integer of 1.

In a further embodiment of the above-mentioned aspect, the invention relates to compounds of formula I, according to any of the above-mentioned embodiments, in the form of or a stereoisomer, a tautomer, an N-oxide, a hydrate, a solvate, or a salt thereof, or a mixture of same.

It is to be understood that the present invention relates also to any combination of the preferred embodiments described above.

Some examples of combinations are given hereinafter. However, the invention is not limited to these combinations.

In a preferred embodiment, the invention relates to compounds of formula I:

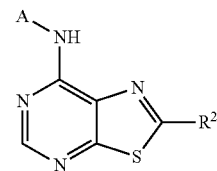

I in which:
A represents a group selected from:

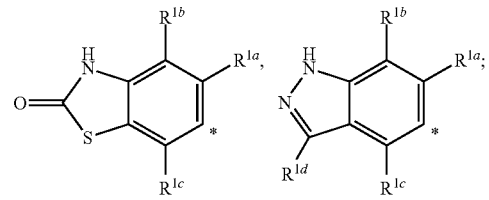

wherein * indicates the point of attachment of said groups with the rest of the molecule;

$R^{1a}$, $R^{1b}$, $R^{1c}$, $R^{1d}$ are the same or different and are independently selected from $R^1$;

$R^1$ represents a hydrogen atom or a halogen atom or a hydroxy-, cyano-, $C_1$-$C_6$-alkyl-, $C_2$-$C_6$-alkenyl-, $C_2$-$C_6$-alkynyl-, $C_1$-$C_6$-alkoxy-, halo-$C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O—, —$NR^{5a}R^{5b}$, —$SCF_3$ or —$SF_5$ group;

wherein said $C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O— group is optionally substituted, identically or differently, with 1, 2, 3, 4 or 5 $R^4$ groups;

$R^2$ represents a hydrogen atom, a halogen atom or a group selected from:
$C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl-, heteroaryl-, cyano-, —$(CH_2)_q$—X—$(CH_2)_p$ —$R^3$;
wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl- or heteroaryl-group is optionally substituted, identically or differently, with 1, 2, 3, 4 or 5 $R^4$ groups;

X represents a bond or a bivalent group selected from:
—O—, —S—, —S(=O)—, —S(=O)$_2$—, —S(=O)—($NR^{3a}$)—, —($NR^{3a}$)—S(=O)—, —S(=O)$_2$—($NR^{3a}$)—, —($NR^{3a}$)—S(=O)$_2$—, —C(=O)—, —($NR^{3a}$)—, —C(=O)—O—, —O—C(=O)—, —C(=S)—O—, —O—C(=S)—, —C(=O)—($NR^{3a}$)—, —($NR^{3a}$)—C (=O)—, —(NR$^{3a}$)—C(=O)—(NR$^{3b}$)—, —O—C(=O)—(NR$^{3a}$)—, —(NR$^{3a}$)—C(=O)—O—;

R$^{3a}$, R$^{3b}$ are the same or different and are independently selected from R$^3$;

R$^3$ represents a hydrogen atom or a group selected from C$_1$-C$_6$-alkyl-, C$_3$-C$_6$-cycloalkyl-, 3- to 10-membered heterocycloalkyl-, aryl-, heteroaryl-; wherein said C$_1$-C$_6$-alkyl-, C$_3$-C$_6$-cycloalkyl-, 3- to 10-membered heterocycloalkyl-, aryl- or heteroaryl-group is optionally substituted, identically or differently, with 1, 2, 3, 4 or 5 R$^4$ groups;

or

R$^3$ together with R$^{3a}$ or R$^{3b}$ represent a 3- to 10-membered heterocycloalkyl- or a 4- to 10-membered heterocycloalkenyl-group, which is optionally substituted, identically or differently, with 1, 2, 3, 4 or 5 R$^4$ groups;

R$^4$ represents halo-, hydroxy-, oxo-(O=), cyano-, nitro-, C$_1$-C$_6$-alkyl-, C$_2$-C$_6$-alkenyl-, C$_2$-C$_6$-alkynyl-, halo-C$_1$-C$_6$-alkyl-, C$_1$-C$_6$-alkoxy-, halo-C$_1$-C$_6$-alkoxy-, hydroxy-C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, R$^5$—O—, —C(=O)—R$^5$, —C(=O)—O—R$^5$, —O—C(=O)—R$^5$, —N(R$^{5a}$)—C(=O)—R$^{5b}$, —N(R$^{5a}$)—C(=O)—NR$^{5b}$R$^{5c}$, —NR$^{5a}$R$^{5b}$, —C(=O)—NR$^{5a}$R$^{5b}$, R$^5$—S—, R$^5$—S(=O)—, R$^5$—S(=O)$_2$—, —N(R$^{5a}$)—S(=O)—R$^{5b}$, —S(=O)—NR$^{5a}$R$^{5b}$, —N(R$^{5a}$)—S(=O)$_2$—R$^{5b}$, —S(=O)$_2$—NR$^{5a}$R$^{5b}$, —S(=O)(=NR$^{5a}$)R$^{5b}$, —S(=O)(=NR$^{5a}$)R$^{5b}$ or —N=S(=O)(R$^{5a}$)R$^{5b}$;

R$^{5a}$, R$^{5b}$, R$^{5c}$ are the same or different and are independently selected from R$^5$;

R$^5$ represents a hydrogen atom, a C$_1$-C$_6$-alkyl- or a C$_3$-C$_6$-cycloalkyl-group;

or

R$^{5a}$ and R$^{5b}$, or R$^{5a}$ and R$^{5c}$, or R$^{5b}$ and R$^{5c}$ together may form a C$_2$-C$_6$-alkylene group, in which optionally one methylene can be replaced by —O—, —C(=O)—, —NH—, or —N(C$_1$-C$_4$-alkyl)-;

p represents an integer of 0, 1, 2 or 3;

q represents an integer of 0, 1, 2 or 3;

or a tautomer, an N-oxide, a hydrate, a solvate, or a salt thereof, or a mixture of same;

with the proviso that A is not

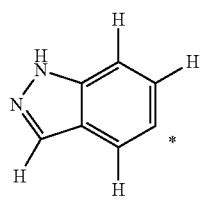

when R$^2$ is

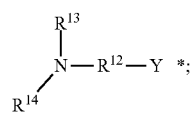

in which:

Y is a direct bond or a group selected from:

—O—, —C(=O)—, —S(=O)$_m$—, —N(R$^{18}$)—, —N(R$^{18}$)C(=O)—, —C(=O)N(R$^{18}$)—, —S(=O)$_m$N(R$^{18}$)—;

R$^{12}$ is a direct bond, an optionally substituted, straight or branched C$_1$-C$_{10}$-alkylene group, which is optionally interposed with a group N(R$^{15}$) where R$^{15}$ is hydrogen or a C$_1$-C$_3$-alkyl group;

R$^{13}$ and R$^{14}$ are independently selected from an optionally substituted C$_1$-C$_{10}$-alkyl-group, an optionally substituted C$_2$-C$_{10}$-alkenyl-group, an optionally substituted C$_2$-C$_{10}$-alkynyl-group or an optionally substituted heterocyclic group;

R$^{18}$ is hydrogen or an optionally substituted C$_1$-C$_4$-alkyl-group;

m is 0, 1 or 2;

* indicates the point of attachment of said groups with the rest of the molecule;

or R$^{13}$ and R$^{14}$ together with the nitrogen atom to which they are attached form an optionally substituted heterocyclic ring, which optionally contains additional heteroatoms;

or R$^{13}$ together with R$^{12}$ or R$^{18}$ and the nitrogen atom(s) to which they are attached form an optionally substituted heterocyclic ring which optionally contains additional heteroatoms;

or R$^{13}$ and R$^{14}$ together with R$^{12}$ form an optionally substituted bridged ring structure;

or R$^{12}$ together with R$^{18}$ may form an optionally substituted cycloalkyl or heterocyclic ring.

In another preferred embodiment, the invention relates to compounds of formula I:

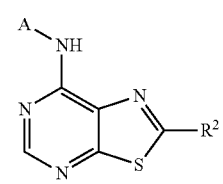

I in which:

A represents a group selected from:

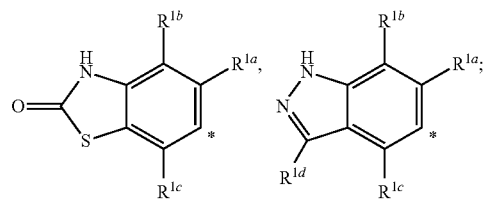

wherein * indicates the point of attachment of said groups with the rest of the molecule;

R$^{1a}$, R$^{1b}$, R$^{1c}$, R$^{1d}$ are the same or different and are independently selected from R$^1$;

R$^1$ represents a hydrogen atom or a halogen atom or a hydroxy-, cyano-, C$_1$-C$_6$-alkyl-, C$_2$-C$_6$-alkenyl-, C$_2$-C$_6$-alkynyl-, C$_1$-C$_6$-alkoxy-, halo-C$_1$-C$_6$-alkoxy-, C$_3$-C$_6$-cycloalkyl-, C$_4$-C$_8$-cycloalkenyl-, C$_3$-C$_6$-cycloalkyloxy-, (3- to 10-membered heterocycloalkyl)-, (3- to 10-membered heterocycloalkyl)-O—, C$_5$-C$_8$-cycloalkenyloxy-, (5- to 10-membered heterocycloalkenyl)-, (5- to 10-membered heterocycloalkenyl)-O—, —NR$^{5a}$R$^{5b}$, —SCF$_3$ or —SF$_5$ group;

wherein said C$_1$-C$_6$-alkyl-, C$_2$-C$_6$-alkenyl-, C$_2$-C$_6$-alkynyl-, C$_1$-C$_6$-alkoxy-, C$_3$-C$_6$-cycloalkyl-, C$_4$-C$_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O— group is optionally substituted, identically or differently, with 1, 2, 3, 4 or 5 $R^4$ groups;

$R^2$ represents a halogen atom or a group selected from: $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl-, heteroaryl-, cyano-, —$(CH_2)_q$—X—$(CH_2)_p$—$R^3$;
wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl- or heteroaryl-group is optionally substituted, identically or differently, with 1, 2, 3, 4 or 5 $R^4$ groups;

X represents a bond or a bivalent group selected from:
—O—, —S—, —S(=O)—, —S(=O)$_2$—, —S(=O)—$(NR^{3a})$—, —$(NR^{3a})$—S(=O)—, —C(=O)—, —$(NR^{3a})$—, —C(=O)—O—, —O—C(=O)—, —C(=S)—O—, —O—C(=S)—, —C(=O)—$(NR^{3a})$—, —$(NR^{3a})$—C(=O)—, —$(NR^{3a})$—C(=O)—$(NR^{3b})$—, —O—C(=O)—$(NR^{3a})$—, —$(NR^{3a})$—C(=O)—O—;

$R^{3a}$, $R^{3b}$ are the same or different and are independently selected from $R^3$;

$R^3$ represents a hydrogen atom or a group selected from $C_1$-$C_6$-alkyl-, $C_3$-$C_6$-cycloalkyl-, 3- to 10-membered heterocycloalkyl-, aryl-, heteroaryl-;
wherein said $C_1$-$C_6$-alkyl-, $C_3$-$C_6$-cycloalkyl-, 3- to 10-membered heterocycloalkyl-, aryl- or heteroaryl-group is optionally substituted, identically or differently, with 1, 2, 3, 4 or 5 $R^4$ groups;

or $R^3$ together with $R^{3a}$ or $R^{3b}$ represent a 3- to 10-membered heterocycloalkyl- or a 4- to 10-membered heterocycloalkenyl-group, which is optionally substituted, identically or differently, with 1, 2, 3, 4 or 5 $R^4$ groups;

$R^4$ represents halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —C(=O)—$R^5$, —C(=O)—O—$R^5$, —O—C(=O)—$R^5$, —N($R^{5a}$)—C(=O)—$R^{5b}$, —N($R^{5a}$)—C(=O)—$NR^{5b}R^{5c}$, —$NR^{5a}R^{5b}$, —C(=O)—$NR^{5a}R^{5b}$, $R^5$—S—, $R^5$—S(=O)—, $R^5$—S(=O)$_2$—, —N($R^{5a}$)—S(=O)—$R^{5b}$, —S(=O)—$NR^{5a}R^{5b}$, —N($R^{5a}$)—S(=O)$_2$—$R^{5b}$, —S(=O)$_2$—$NR^{5a}R^{5b}$, —S(=O)(=$NR^{5a}$)$R^{5b}$, —S(=O)(=$NR^{5a}$)$R^{5b}$ or —N=S(=O)($R^{5a}$)$R^{5b}$;

$R^{5a}$, $R^{5b}$, $R^{5c}$ are the same or different and are independently selected from $R^5$;

$R^5$ represents a hydrogen atom, a $C_1$-$C_6$-alkyl- or a $C_3$-$C_6$-cycloalkyl-group;

or $R^{5a}$ and $R^{5b}$,
or $R^{5a}$ and $R^{5c}$,
or $R^{5b}$ and $R^{5c}$ together may form a $C_2$-$C_6$-alkylene group, in which optionally one methylene can be replaced by —O—, —C(=O)—, —NH—, or —N($C_1$-$C_4$-alkyl)-;

p represents an integer of 0, 1, 2 or 3;
q represents an integer of 0, 1, 2 or 3;

or a tautomer, an N-oxide, a hydrate, a solvate, or a salt thereof, or a mixture of same;
with the proviso that A is not

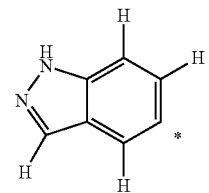

when $R^2$ is

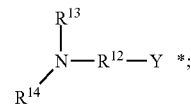

in which:

Y is a direct bond or a group selected from:
—O—, —C(=O)—, —S(=O)$_m$—, —N($R^{18}$)—, —N($R^{18}$)C(=O)—, —C(=O)N($R^{18}$)—, —S(=O)$_m$N($R^{18}$)—;

$R^{12}$ is a direct bond, an optionally substituted, straight or branched $C_1$-$C_{10}$-alkylene group, which is optionally interposed with a group N($R^{15}$) where $R^{15}$ is hydrogen or a $C_1$-$C_3$-alkyl group;

$R^{13}$ and $R^{14}$ are independently selected from an optionally substituted $C_1$-$C_{10}$-alkyl-group, an optionally substituted $C_2$-$C_{10}$-alkenyl-group, an optionally substituted $C_2$-$C_{10}$-alkynyl-group or an optionally substituted heterocyclic group;

$R^{18}$ is hydrogen or an optionally substituted $C_1$-$C_4$-alkyl-group;

m is 0, 1 or 2;

* indicates the point of attachment of said groups with the rest of the molecule;

or $R^{13}$ and $R^{14}$ together with the nitrogen atom to which they are attached form an optionally substituted heterocyclic ring, which optionally contains additional heteroatoms;

or $R^{13}$ together with $R^{12}$ or $R^{18}$ and the nitrogen atom(s) to which they are attached form an optionally substituted heterocyclic ring which optionally contains additional heteroatoms;

or $R^{13}$ and $R^{14}$ together with $R^{12}$ form an optionally substituted bridged ring structure;

or $R^{12}$ together with $R^{18}$ may form an optionally substituted cycloalkyl or heterocyclic ring.

In another preferred embodiment, the invention relates to compounds of formula I:

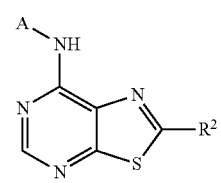

I in which:

A represents a group selected from:

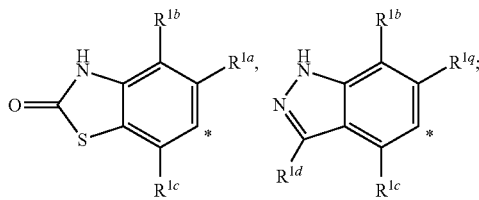

wherein * indicates the point of attachment of said groups with the rest of the molecule;

$R^{1a}$, $R^{1b}$, $R^{1c}$, $R^{1d}$ are the same or different and are independently selected from $R^1$;

$R^1$ represents a hydrogen atom or a halogen atom or a hydroxy-, cyano-, $C_1$-$C_6$-alkyl-, halo-$C_1$-$C_6$-alkyl-, $C_2$-$C_6$-alkenyl-, $C_2$-$C_6$-alkynyl-, $C_1$-$C_6$-alkoxy-, halo-$C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O—, —$NR^{5a}R^{5b}$, —$SCF_3$ or —$SF_5$ group;

wherein said $C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O— group is optionally substituted, identically or differently, with 1, 2, 3, 4 or 5 $R^4$ groups;

$R^{1q}$ represents a halogen atom or a hydroxy-, cyano-, $C_1$-$C_6$-alkyl-, halo-$C_1$-$C_6$-alkyl-, $C_2$-$C_6$-alkenyl-, $C_2$-$C_6$-alkynyl-, $C_1$-$C_6$-alkoxy-, halo-$C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O—, —$NR^{5a}R^{5b}$, —$SCF_3$ or —$SF_5$ group;

wherein said $C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O— group is optionally substituted, identically or differently, with 1, 2, 3, 4 or 5 $R^4$ groups;

$R^2$ represents a halogen atom or a group selected from: $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl-, heteroaryl-, halo-$C_1$-$C_3$-alkyl-, cyano-, —$(CH_2)_q$—X—$(CH_2)_p$—$R^3$;

wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl- or heteroaryl-group is optionally substituted, identically or differently, with 1, 2, 3, 4 or 5 $R^4$ groups;

X represents a bond or a bivalent group selected from:
—O—, —S—, —S(=O)—, —S(=O)$_2$—, —S(=O)—($NR^{3a}$)—, —($NR^{3a}$)—S(=O)—, —C(=O)—, —($NR^{3a}$)—, —C(=O)—O—, —O—C(=O)—, —C(=S)—O—, —O—C(=S)—, —C(=O)—($NR^{3a}$)—, —($NR^{3a}$)—C(=O)—, —($NR^{3a}$)—C(=O)—($NR^{3b}$)—, —O—C(=O)—($NR^{3a}$)—, —($NR^{3a}$)—C(=O)—O—;

$R^{3a}$, $R^{3b}$ are the same or different and are independently selected from $R^3$;

$R^3$ represents a hydrogen atom or a group selected from $C_1$-$C_6$-alkyl-, $C_3$-$C_6$-cycloalkyl-, 3- to 10-membered heterocycloalkyl-, aryl-, heteroaryl-, halo-$C_1$-$C_3$-alkyl-;

wherein said $C_1$-$C_6$-alkyl-, $C_3$-$C_6$-cycloalkyl-, 3- to 10-membered heterocycloalkyl-, aryl- or heteroaryl-group is optionally substituted, identically or differently, with 1, 2, 3, 4 or 5 $R^4$ groups;

or $R^3$ together with $R^{3a}$ or $R^{3b}$ represent a 3- to 10-membered heterocycloalkyl- or a 4- to 10-membered heterocycloalkenyl-group, which is optionally substituted, identically or differently, with 1, 2, 3, 4 or 5 $R^4$ groups;

$R^4$ represents halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —C(=O)—$R^5$, —C(=O)—O—$R^5$, —O—C(=O)—$R^5$, —N($R^{5a}$)—C(=O)—$R^{5b}$, —N($R^{5a}$)—C(=O)—$NR^{5b}R^{5c}$, —$NR^{5a}R^{5b}$, —C(=O)—$NR^{5a}R^{5b}$, $R^5$—S—, $R^5$—S(=O)—, $R^5$—S(=O)$_2$—, —N($R^{5a}$)—S(=O)—$R^{5b}$, —S(=O)—$NR^{5a}R^{5b}$, —N($R^{5a}$)—S(=O)$_2$—$R^{5b}$, —S(=O)$_2$—$NR^{5a}R^{5b}$, —S(=O)(=$NR^{5a}$)$R^{5b}$, —S(=O)(=$NR^{5a}$)$R^{5b}$ or —N=S(=O)($R^{5a}$)$R^{5b}$;

$R^{5a}$, $R^{5b}$, $R^{5c}$ are the same or different and are independently selected from $R^5$;

$R^5$ represents a hydrogen atom, a $C_1$-$C_6$-alkyl- or a $C_3$-$C_6$-cycloalkyl-group;

or $R^{5a}$ and $R^{5b}$, or $R^{5a}$ and $R^{5c}$, or $R^{5b}$ and $R^{5c}$ together may form a $C_2$-$C_6$-alkylene group, in which optionally one methylene can be replaced by —O—, —C(=O)—, —NH—, or —N($C_1$-$C_4$-alkyl)-;

p represents an integer of 0, 1, 2 or 3;

q represents an integer of 0, 1, 2 or 3;

or a tautomer, an N-oxide, a hydrate, a solvate, or a salt thereof, or a mixture of same.

In another preferred embodiment, the invention relates to compounds of formula I:

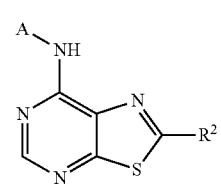

I in which:

A represents a group selected from:

[structures showing a benzothiazolone with R$^{1b}$, R$^{1a}$, R$^{1c}$ substituents and an indazole with R$^{1b}$, R$^{1q}$, R$^{1d}$, R$^{1c}$ substituents]

wherein * indicates the point of attachment of said groups with the rest of the molecule;

R$^{1a}$, R$^{1b}$, R$^{1c}$, R$^{1d}$ are the same or different and are independently selected from R$^1$;

R$^1$ represents a hydrogen atom or a halogen atom or a hydroxy-, cyano-, C$_1$-C$_6$-alkyl-, halo-C$_1$-C$_6$-alkyl-, C$_2$-C$_6$-alkenyl-, C$_2$-C$_6$-alkynyl-, C$_1$-C$_6$-alkoxy-, halo-C$_1$-C$_6$-alkoxy-, C$_3$-C$_6$-cycloalkyl-, C$_4$-C$_8$-cycloalkenyl-, C$_3$-C$_6$-cycloalkyloxy-, (3- to 10-membered heterocycloalkyl)-, (3- to 10-membered heterocycloalkyl)-O—, C$_5$-C$_8$-cycloalkenyloxy-, (5- to 10-membered heterocycloalkenyl)-, (5- to 10-membered heterocycloalkenyl)-O—, —NR$^{5a}$R$^{5b}$, —SCF$_3$ or —SF$_5$ group;

wherein said C$_1$-C$_6$-alkyl-, C$_2$-C$_6$-alkenyl-, C$_2$-C$_6$-alkynyl-, C$_1$-C$_6$-alkoxy-, C$_3$-C$_6$-cycloalkyl-, C$_4$-C$_8$-cycloalkenyl-, C$_3$-C$_6$-cycloalkyloxy-, (3- to 10-membered heterocycloalkyl)-, (3- to 10-membered heterocycloalkyl)-O—, C$_5$-C$_8$-cycloalkenyloxy-, (5- to 10-membered heterocycloalkenyl)-, (5- to 10-membered heterocycloalkenyl)-O— group is optionally substituted, identically or differently, with 1, 2, 3, 4 or 5 R$^4$ groups;

R$^{1q}$ represents a halogen atom or a hydroxy-, cyano-, C$_1$-C$_6$-alkyl-, halo-C$_1$-C$_6$-alkyl-, C$_2$-C$_6$-alkenyl-, C$_2$-C$_6$-alkynyl-, C$_1$-C$_6$-alkoxy-, halo-C$_1$-C$_6$-alkoxy-, C$_3$-C$_6$-cycloalkyl-, C$_4$-C$_8$-cycloalkenyl-, C$_3$-C$_6$-cycloalkyloxy-, (3- to 10-membered heterocycloalkyl)-, (3- to 10-membered heterocycloalkyl)-O—, C$_5$-C$_8$-cycloalkenyloxy-, (5- to 10-membered heterocycloalkenyl)-, (5- to 10-membered heterocycloalkenyl)-O—, —NR$^{5a}$R$^{5b}$, —SCF$_3$ or —SF$_5$ group;

wherein said C$_1$-C$_6$-alkyl-, C$_2$-C$_6$-alkenyl-, C$_2$-C$_6$-alkynyl-, C$_1$-C$_6$-alkoxy-, C$_3$-C$_6$-cycloalkyl-, C$_4$-C$_8$-cycloalkenyl-, C$_3$-C$_6$-cycloalkyloxy-, (3- to 10-membered heterocycloalkyl)-, (3- to 10-membered heterocycloalkyl)-O—, C$_5$-C$_8$-cycloalkenyloxy-, (5- to 10-membered heterocycloalkenyl)-, (5- to 10-membered heterocycloalkenyl)-O— group is optionally substituted, identically or differently, with 1, 2, 3, 4 or 5 R$^4$ groups;

R$^2$ represents a hydrogen atom, a halogen atom or a group selected from:

C$_1$-C$_6$-alkyl-, C$_3$-C$_6$-cycloalkyl-, C$_4$-C$_6$-cycloalkenyl-, C$_2$-C$_6$-alkenyl-, C$_2$-C$_6$-alkynyl-, 3- to 10-membered heterocycloalkyl-, 4- to 10-membered heterocycloalkenyl-, aryl-, heteroaryl-, halo-C$_1$-C$_3$-alkyl-, cyano-, —(CH$_2$)$_q$—X—(CH$_2$)$_p$—R$^3$;

wherein said C$_1$-C$_6$-alkyl-, C$_3$-C$_6$-cycloalkyl-, C$_4$-C$_6$-cycloalkenyl-, C$_2$-C$_6$-alkenyl-, C$_2$-C$_6$-alkynyl-, 3- to 10-membered heterocycloalkyl-, 4- to 10-membered heterocycloalkenyl-, aryl- or heteroaryl-group is optionally substituted, identically or differently, with 1, 2, 3, 4 or 5 R$^4$ groups;

X represents a bond or a bivalent group selected from: —O—, —S—, —S(=O)—, —S(=O)$_2$—, —S(=O)—(NR$^{3a}$)—, —(NR$^{3a}$)—S(=O)—, —S(=O)$_2$—(NR$^{3a}$)—, —(NR$^{3a}$)—S(=O)$_2$—, —C(=O)—, —(NR$^{3a}$)—, —C(=O)—O—, —O—C(=O)—, —C(=S)—O—, —O—C(=S)—, —C(=O)—(NR$^{3a}$)—, —(NR$^{3a}$)—C(=O)—, —(NR$^{3a}$)—C(=O)—(NR$^{3b}$)—, —O—C(=O)—(NR$^{3a}$)—, —(NR$^{3a}$)—C(=O)—O—;

R$^{3a}$, R$^{3b}$ are the same or different and are independently selected from R$^3$;

R$^3$ represents a hydrogen atom or a group selected from C$_1$-C$_6$-alkyl-, C$_3$-C$_6$-cycloalkyl-, 3- to 10-membered heterocycloalkyl-, aryl-, heteroaryl-, halo-C$_1$-C$_3$-alkyl-;

wherein said C$_1$-C$_6$-alkyl-, C$_3$-C$_6$-cycloalkyl-, 3- to 10-membered heterocycloalkyl-, aryl- or heteroaryl-group is optionally substituted, identically or differently, with 1, 2, 3, 4 or 5 R$^4$ groups;

or

R$^3$ together with R$^{3a}$ or R$^{3b}$ represent a 3- to 10-membered heterocycloalkyl- or a 4- to 10-membered heterocycloalkenyl-group, which is optionally substituted, identically or differently, with 1, 2, 3, 4 or 5 R$^4$ groups;

R$^4$ represents halo-, hydroxy-, oxo-(O=), cyano-, nitro-, C$_1$-C$_6$-alkyl-, C$_2$-C$_6$-alkenyl-, C$_2$-C$_6$-alkynyl-, halo-C$_1$-C$_6$-alkyl-, C$_1$-C$_6$-alkoxy-, halo-C$_1$-C$_6$-alkoxy-, hydroxy-C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, R$^5$—O—, —C(=O)—R$^5$, —C(=O)—O—R$^5$, —O—C(=O)—R$^5$, —N(R$^{5a}$)—C(=O)—R$^{5b}$, —N(R$^{5a}$)—C(=O)—NR$^{5b}$R$^{5c}$, —NR$^{5a}$R$^{5b}$, —C(=O)—NR$^{5a}$R$^{5b}$, R$^5$—S—, R$^5$—S(=O)—, R$^5$—S(=O)$_2$—, —N(R$^{5a}$)—S(=O)—R$^{5b}$, —S(=O)—NR$^{5a}$R$^{5b}$, —N(R$^{5a}$)—S(=O)$_2$—R$^{5b}$, —S(=O)$_2$—NR$^{5a}$R$^{5b}$, —S(=O)(=NR$^{5a}$)R$^{5b}$, —S(=O)(=NR$^{5a}$)R$^{5b}$ or —N=S(=O)(R$^{5a}$)R$^{5b}$;

R$^{5a}$, R$^{5b}$, R$^{5c}$ are the same or different and are independently selected from R$^5$;

R$^5$ represents a hydrogen atom, a C$_1$-C$_6$-alkyl- or a C$_3$-C$_6$-cycloalkyl-group;

or

R$^{5a}$ and R$^{5b}$, or R$^{5a}$ and R$^{5c}$, or R$^{5b}$ and R$^{5c}$ together may form a C$_2$-C$_6$-alkylene group, in which optionally one methylene can be replaced by —O—, —C(=O)—, —NH—, or —N(C$_1$-C$_4$-alkyl)-;

p represents an integer of 0, 1, 2 or 3;

q represents an integer of 0, 1, 2 or 3;

or a tautomer, an N-oxide, a hydrate, a solvate, or a salt thereof, or a mixture of same.

In another preferred embodiment, the invention relates to compounds of formula I:

[structure of formula I showing A-NH group attached to a thiazolopyrimidine bearing R$^2$]

I in which:

A represents a group selected from:

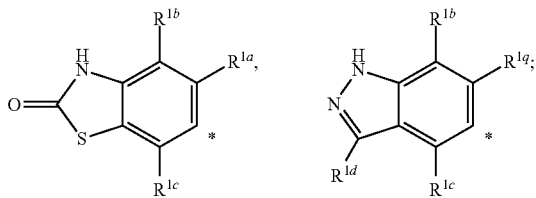

wherein * indicates the point of attachment of said groups with the rest of the molecule;

$R^{1a}$ represents a hydrogen atom or a halogen atom or a hydroxy-, cyano-, $C_1$-$C_6$-alkyl-, halo-$C_1$-$C_6$-alkyl-, $C_2$-$C_6$-alkenyl-, $C_2$-$C_6$-alkynyl-, $C_1$-$C_6$-alkoxy-, halo-$C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O—, —$NR^{5a}R^{5b}$, —$SCF_3$ or —$SF_5$ group;

wherein said $C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O— group is optionally substituted, identically or differently, with 1, 2, 3, 4 or 5 $R^4$ groups;

each of $R^{1b}$, $R^{1c}$, and $R^{1d}$ represents a hydrogen atom;

$R^{1q}$ represents a halogen atom or a hydroxy-, cyano-, $C_1$-$C_6$-alkyl-, halo-$C_1$-$C_6$-alkyl-, $C_2$-$C_6$-alkenyl-, $C_2$-$C_6$-alkynyl-, $C_1$-$C_6$-alkoxy-, halo-$C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O—, —$NR^{5a}R^{5b}$, —$SCF_3$ or —$SF_5$ group;

wherein said $C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O— group is optionally substituted, identically or differently, with 1, 2, 3, 4 or 5 $R^4$ groups;

$R^2$ represents a halogen atom or a group selected from: $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl-, heteroaryl-, halo-$C_1$-$C_3$-alkyl-, cyano-, —$(CH_2)_q$—X—$(CH_2)_p$—$R^3$;

wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl- or heteroaryl-group is optionally substituted, identically or differently, with 1, 2, 3, 4 or 5 $R^4$ groups;

X represents a bond or a bivalent group selected from: —O—, —S—, —S(=O)—, —S(=O)$_2$—, —S(=O)—($NR^{3a}$)—, —($NR^{3a}$)—S(=O)—, —C(=O)—, —($NR^{3a}$)—, —C(=O)—O—, —O—C(=O)—, —C(=S)—O—, —O—C(=S)—, —C(=O)—($NR^{3a}$)—, —($NR^{3a}$)—C(=O)—, —($NR^{3a}$)—C(=O)—($NR^{3b}$)—, —O—C(=O)—($NR^{3a}$)—, —($NR^{3a}$)—C(=O)—O—;

$R^{3a}$, $R^{3b}$ are the same or different and are independently selected from $R^3$;

$R^3$ represents a hydrogen atom or a group selected from $C_1$-$C_6$-alkyl-, $C_3$-$C_6$-cycloalkyl-, 3- to 10-membered heterocycloalkyl-, aryl-, heteroaryl-, halo-$C_1$-$C_3$-alkyl-;

wherein said $C_1$-$C_6$-alkyl-, $C_3$-$C_6$-cycloalkyl-, 3- to 10-membered heterocycloalkyl-, aryl- or heteroaryl-group is optionally substituted, identically or differently, with 1, 2, 3, 4 or 5 $R^4$ groups;

or $R^3$ together with $R^{3a}$ or $R^{3b}$ represent a 3- to 10-membered heterocycloalkyl- or a 4- to 10-membered heterocycloalkenyl-group, which is optionally substituted, identically or differently, with 1, 2, 3, 4 or 5 $R^4$ groups;

$R^4$ represents halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —C(=O)—$R^5$, —C(=O)—O—$R^5$, —O—C(=O)—$R^5$, —N($R^{5a}$)—C(=O)—$R^{5b}$, —N($R^{5a}$)—C(=O)—$NR^{5b}R^{5c}$, —$NR^{5a}R^{5b}$, —C(=O)—$NR^{5a}R^{5b}$, $R^5$—S—, $R^5$—S(=O)—, $R^5$—S(=O)$_2$—, —N($R^{5a}$)—S(=O)—$R^{5b}$, —S(=O)—$NR^{5a}R^{5b}$, —N($R^{5a}$)—S(=O)$_2$—$R^{5b}$, —S(=O)$_2$—$NR^{5a}R^{5b}$, —S(=O)(=$NR^{5a}$)$R^{5b}$, —S(=O)(=$NR^{5a}$)$R^{5b}$ or —N=S(=O)($R^{5a}$)$R^{5b}$;

$R^{5a}$, $R^{5b}$, $R^{5c}$ are the same or different and are independently selected from $R^5$;

$R^5$ represents a hydrogen atom, a $C_1$-$C_6$-alkyl- or a $C_3$-$C_6$-cycloalkyl-group;

or $R^{5a}$ and $R^{5b}$, or $R^{5a}$ and $R^{5c}$, or $R^{5b}$ and $R^{5c}$ together may form a $C_2$-$C_6$-alkylene group, in which optionally one methylene can be replaced by —O—, —C(=O)—, —NH—, or —N($C_1$-$C_4$-alkyl)-;

p represents an integer of 0, 1, 2 or 3;

q represents an integer of 0, 1, 2 or 3;

or a tautomer, an N-oxide, a hydrate, a solvate, or a salt thereof, or a mixture of same.

In another preferred embodiment, the invention relates to compounds of formula I:

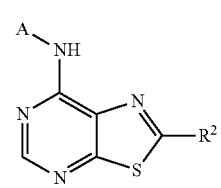

I in which:

A represents a group selected from:

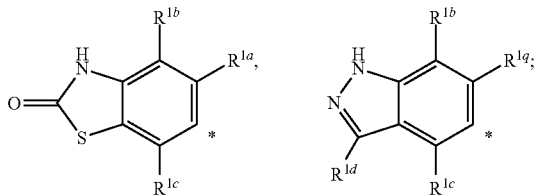

wherein * indicates the point of attachment of said groups with the rest of the molecule;

$R^{1a}$ represents a hydrogen atom or a halogen atom or a hydroxy-, cyano-, $C_1$-$C_6$-alkyl-, halo-$C_1$-$C_6$-alkyl-, $C_2$-$C_6$-alkenyl-, $C_2$-$C_6$-alkynyl-, $C_1$-$C_6$-alkoxy-, halo-$C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O—, —$NR^{5a}R^{5b}$, —$SCF_3$ or —$SF_5$ group;

wherein said $C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O— group is optionally substituted, identically or differently, with 1, 2, 3, 4 or 5 $R^4$ groups;

each of $R^{1b}$, $R^{1c}$, and $R^{1d}$ represents a hydrogen atom;

$R^{1q}$ represents a halogen atom or a hydroxy-, cyano-, $C_1$-$C_6$-alkyl-, halo-$C_1$-$C_6$-alkyl-, $C_2$-$C_6$-alkenyl-, $C_2$-$C_6$-alkynyl-, $C_1$-$C_6$-alkoxy-, halo-$C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O—, —$NR^{5a}R^{5b}$, —$SCF_3$ or —$SF_5$ group;

wherein said $C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O— group is optionally substituted, identically or differently, with 1, 2, 3, 4 or 5 $R^4$ groups;

$R^2$ represents a hydrogen atom, a halogen atom or a group selected from:

$C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl-, heteroaryl-, halo-$C_1$-$C_3$-alkyl-, cyano-, —$(CH_2)_q$—X—$(CH_2)_p$—$R^3$;

wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl- or heteroaryl-group is optionally substituted, identically or differently, with 1, 2, 3, 4 or 5 $R^4$ groups;

X represents a bond or a bivalent group selected from: —O—, —S—, —S(=O)—, —S(=O)$_2$—, —S(=O)—(NR$^{3a}$)—, —(NR$^{3a}$)—S(=O)—, —S(=O)$_2$—(NR$^{3a}$)—, —(NR$^{3a}$)—S(=O)$_2$—, —C(=O)—, —(NR$^{3a}$)—, —C(=O)—O—, —O—C(=O)—, —C(=S)—O—, —O—C(=S)—, —C(=O)—(NR$^{3a}$)—, —(NR$^{3a}$)—C(=O)—, —(NR$^{3a}$)—C(=O)—(NR$^{3b}$)—, —O—C(=O)—(NR$^{3a}$)—, —(NR$^{3a}$)—C(=O)—O—;

$R^{3a}$, $R^{3b}$ are the same or different and are independently selected from $R^3$;

$R^3$ represents a hydrogen atom or a group selected from $C_1$-$C_6$-alkyl-, $C_3$-$C_6$-cycloalkyl-, 3- to 10-membered heterocycloalkyl-, aryl-, heteroaryl-, halo-$C_1$-$C_3$-alkyl-;

wherein said $C_1$-$C_6$-alkyl-, $C_3$-$C_6$-cycloalkyl-, 3- to 10-membered heterocycloalkyl-, aryl- or heteroaryl-group is optionally substituted, identically or differently, with 1, 2, 3, 4 or 5 $R^4$ groups;

or $R^3$ together with $R^{3a}$ or $R^{3b}$ represent a 3- to 10-membered heterocycloalkyl- or a 4- to 10-membered heterocycloalkenyl-group, which is optionally substituted, identically or differently, with 1, 2, 3, 4 or 5 $R^4$ groups;

$R^4$ represents halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —C(=O)—$R^5$, —C(=O)—O—$R^5$, —O—C(=O)—$R^5$, —N($R^{5a}$)—C(=O)—$R^{5b}$, —N($R^{5a}$)—C(=O)—$NR^{5b}R^{5c}$, —$NR^{5a}R^{5b}$, —C(=O)—$NR^{5a}R^{5b}$, $R^5$—S—, $R^5$—S(=O)—, $R^5$—S(=O)$_2$—, —N($R^{5a}$)—S(=O)—$R^{5b}$, —S(=O)—$NR^{5a}R^{5b}$, —N($R^{5a}$)—S(=O)$_2$—$R^{5b}$, —S(=O)$_2$—$NR^{5a}R^{5b}$, —S(=O)(=N$R^{5a}$)$R^{5b}$, —S(=O)(=N$R^{5a}$)$R^{5b}$ or —N=S(=O)($R^{5a}$)$R^{5b}$;

$R^{5a}$, $R^{5b}$, $R^{5c}$ are the same or different and are independently selected from $R^5$;

$R^5$ represents a hydrogen atom, a $C_1$-$C_6$-alkyl- or a $C_3$-$C_6$-cycloalkyl-group;

or $R^{5a}$ and $R^{5b}$, or $R^{5a}$ and $R^{5c}$, or $R^{5b}$ and $R^{5c}$ together may form a $C_2$-$C_6$-alkylene group, in which optionally one methylene can be replaced by —O—, —C(=O)—, —NH—, or —N($C_1$-$C_4$-alkyl)-;

p represents an integer of 0, 1, 2 or 3;

q represents an integer of 0, 1, 2 or 3;

or a tautomer, an N-oxide, a hydrate, a solvate, or a salt thereof, or a mixture of same.

In another preferred embodiment, the invention relates to compounds of formula I:

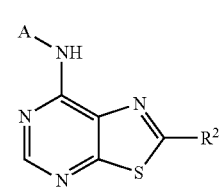

in which:
A represents a group selected from:

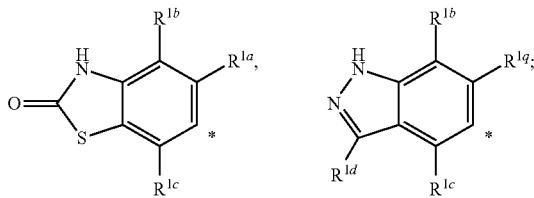

wherein * indicates the point of attachment of said groups with the rest of the molecule;
$R^{1a}$ represents a hydrogen atom or a group selected from: $C_1$-$C_3$-alkyl-, $C_1$-$C_3$-alkoxy-, halo-;
each of
$R^{1b}$, $R^{1c}$, and $R^{1d}$ represents a hydrogen atom;
$R^{1q}$ represents a hydrogen atom or a group selected from: $C_1$-$C_3$-alkyl-, $C_1$-$C_3$-alkoxy-, halo-;
$R^2$ represents a group selected from: $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, aryl-, —$(CH_2)_q$—$(C_3$-$C_6$-cycloalkyl), —$(CH_2)_q$-(aryl);
wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, aryl-, —$(CH_2)_q$—$(C_3$-$C_6$-cycloalkyl) or —$(CH_2)_q$-(aryl) group is optionally substituted, identically or differently, with 1, 2 or 3 $R^4$ groups;
$R^4$ represents halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —C(=O)—$R^5$, —C(=O)—O—$R^5$, —O—C(=O)—$R^5$;
$R^5$ represents a hydrogen atom, a $C_1$-$C_6$-alkyl- or a $C_3$-$C_6$-cycloalkyl-group;
q represents an integer of 1 or 2;
or a tautomer, an N-oxide, a hydrate, a solvate, or a salt thereof, or a mixture of same.

In another preferred embodiment, the invention relates to compounds of formula I:

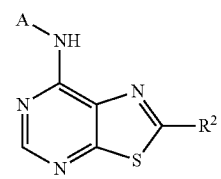

I in which:
A represents a group selected from:

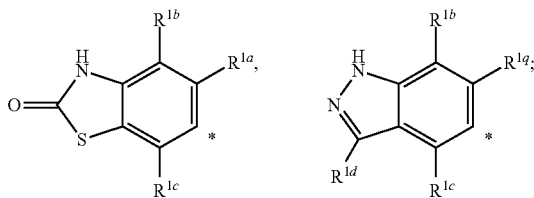

wherein * indicates the point of attachment of said groups with the rest of the molecule;
$R^{1a}$ represents a hydrogen atom or a group selected from: $C_1$-$C_3$-alkyl-, $C_1$-$C_3$-alkoxy-, halo-;
each of
$R^{1b}$, $R^{1c}$, and $R^{1d}$ represents a hydrogen atom;
$R^{1q}$ represents a hydrogen atom or a group selected from: $C_1$-$C_3$-alkyl-, $C_1$-$C_3$-alkoxy-, halo-;
$R^2$ represents a hydrogen atom or a group selected from: $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, aryl-, —$(CH_2)_q$—$(C_3$-$C_6$-cycloalkyl), —$(CH_2)_q$-(aryl), —$(CH_2)_q$—X—$(CH_2)_p$—$R^3$;

wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, aryl-, —$(CH_2)_q$—$(C_3$-$C_6$-cycloalkyl) or —$(CH_2)_q$-(aryl) group is optionally substituted, identically or differently, with 1, 2 or 3 $R^4$ groups;

X represents a bond or a bivalent group selected from: —O—, —C(=O)—, —C(=O)—$(NR^{3a})$—, —$(NR^{3a})$—C(=O)—;

$R^{3a}$ represents a hydrogen atom or a group selected from $C_1$-$C_6$-alkyl-, $C_3$-$C_6$-cycloalkyl-, 3- to 10-membered heterocycloalkyl-, aryl-;
wherein said $C_1$-$C_6$-alkyl-, $C_3$-$C_6$-cycloalkyl-, 3- to 10-membered heterocycloalkyl- or aryl-group is optionally substituted, identically or differently, with 1, 2 or 3 $R^4$ groups;

$R^4$ represents halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —C(=O)—$R^5$, —C(=O)—O—$R^5$, —O—C(=O)—$R^5$, —C(=O)—$NR^{5a}R^{5b}$;

$R^5$ represents a hydrogen atom, a $C_1$-$C_6$-alkyl- or a $C_3$-$C_6$-cycloalkyl-group;

p represents an integer of 0 or 1;
q represents an integer of 0, 1, 2 or 3;
or a tautomer, an N-oxide, a hydrate, a solvate, or a salt thereof, or a mixture of same.

In another preferred embodiment, the invention relates to compounds of formula I:

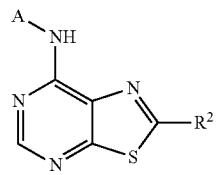

I in which:
A represents a group selected from:

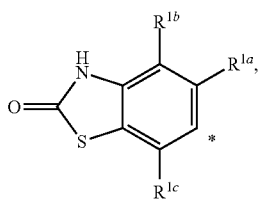 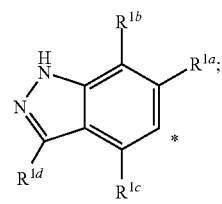

wherein * indicates the point of attachment of said groups with the rest of the molecule;

$R^{1a}$, $R^{1b}$, $R^{1c}$, $R^{1d}$ are the same or different and are independently selected from $R^1$;

$R^1$ represents a hydrogen atom or a halogen atom or a hydroxy-, cyano-, $C_1$-$C_6$-alkyl-, halo-$C_1$-$C_6$-alkyl-, $C_2$-$C_6$-alkenyl-, $C_2$-$C_6$-alkynyl-, $C_1$-$C_6$-alkoxy-, halo-$C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O—, —$NR^{5a}R^{5b}$, —$SCF_3$ or —$SF_5$ group;

wherein said $C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O— group is optionally substituted, identically or differently, with 1, 2, 3, 4 or 5 $R^4$ groups;

$R^2$ represents a halogen atom or a group selected from: $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, aryl-, halo-$C_1$-$C_3$-alkyl-, cyano-, —$(CH_2)_q$—X—$(CH_2)_p$—$R^3$;
wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl- or aryl-group is optionally substituted, identically or differently, with 1, 2, 3, 4 or 5 $R^4$ groups;

X represents a bond or a bivalent group selected from: —O—, —S—, —S(=O)—, —S(=O)$_2$—, —C(=O)—, —C(=O)—O—, —O—C(=O)—, —C(=S)—O—, —O—C(=S)—;

$R^{3a}$, $R^{3b}$ are the same or different and are independently selected from $R^3$;

$R^3$ represents a hydrogen atom or a group selected from $C_1$-$C_6$-alkyl-, $C_3$-$C_6$-cycloalkyl-, aryl-, halo-$C_1$-$C_3$-alkyl-;
wherein said $C_1$-$C_6$-alkyl-, $C_3$-$C_6$-cycloalkyl- or aryl-group is optionally substituted, identically or differently, with 1, 2, 3, 4 or 5 $R^4$ groups;

$R^4$ represents halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —C(=O)—$R^5$, —C(=O)—O—$R^5$ or —O—C(=O)—$R^5$;

$R^5$ represents a hydrogen atom, a $C_1$-$C_6$-alkyl- or a $C_3$-$C_6$-cycloalkyl-group;

p represents an integer of 0, 1, 2 or 3;
q represents an integer of 0, 1, 2 or 3;
or a tautomer, an N-oxide, a hydrate, a solvate, or a salt thereof, or a mixture of same.

In another preferred embodiment, the invention relates to compounds of formula I:

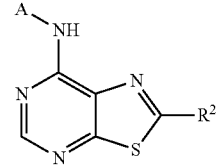

I in which:
A represents a group selected from:

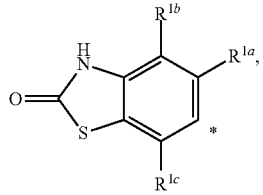 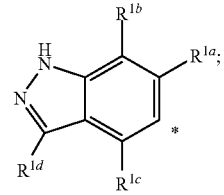

wherein * indicates the point of attachment of said groups with the rest of the molecule;

$R^{1a}$, $R^{1b}$, $R^{1c}$, $R^{1d}$ are the same or different and are independently selected from $R^1$;

$R^1$ represents a hydrogen atom or a halogen atom or a hydroxy-, cyano-, $C_1$-$C_6$-alkyl-, halo-$C_1$-$C_6$-alkyl-, $C_2$-$C_6$-alkenyl-, $C_2$-$C_6$-alkynyl-, $C_1$-$C_6$-alkoxy-, halo-$C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O—, —$NR^{5a}R^{5b}$, —$SCF_3$ or —$SF_5$ group;

wherein said $C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O— group is optionally substituted, identically or differently, with 1, 2, 3, 4 or 5 $R^4$ groups;

$R^2$ represents a hydrogen atom or a halogen atom or a group selected from:

$C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, aryl-, halo-$C_1$-$C_3$-alkyl-, cyano-, —$(CH_2)_q$—X—$(CH_2)_p$—$R^3$; wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl- or aryl-group is optionally substituted, identically or differently, with 1, 2, 3, 4 or 5 $R^4$ groups;

X represents a bond or a bivalent group selected from: —O—, —S—, —S(═O)—, —S(═O)$_2$—, —C(═O)—, —C(═O)—O—, —O—C(═O)—, —C(═S)—O—, —O—C(═S)—, —C(═O)—($NR^{3a}$)—, —($NR^{3a}$)—C(═O)—;

$R^{3a}$, $R^{3b}$ are the same or different and are independently selected from $R^3$;

$R^3$ represents a hydrogen atom or a group selected from $C_1$-$C_6$-alkyl-, $C_3$-$C_6$-cycloalkyl-, aryl-, halo-$C_1$-$C_3$-alkyl-;

wherein said $C_1$-$C_6$-alkyl-, $C_3$-$C_6$-cycloalkyl- or aryl-group is optionally substituted, identically or differently, with 1, 2, 3, 4 or 5 $R^4$ groups;

$R^4$ represents halo-, hydroxy-, oxo-(O═), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —C(═O)—$R^5$, —C(═O)—O—$R^5$, —O—C(═O)—$R^5$, —C(═O)—$NR^{5a}R^{5b}$;

$R^5$ represents a hydrogen atom, a $C_1$-$C_6$-alkyl- or a $C_3$-$C_6$-cycloalkyl-group;

p represents an integer of 0, 1, 2 or 3;

q represents an integer of 0, 1, 2 or 3;

or a tautomer, an N-oxide, a hydrate, a solvate, or a salt thereof, or a mixture of same.

In another preferred embodiment, the invention relates to compounds of formula I:

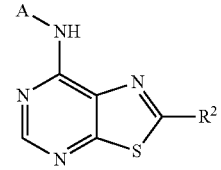

in which:

A represents a group selected from:

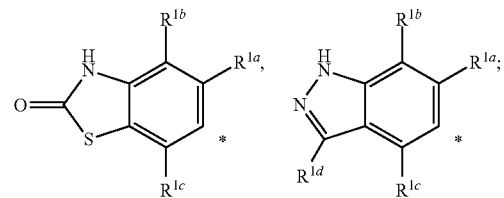

wherein * indicates the point of attachment of said groups with the rest of the molecule;

$R^{1a}$ represents a hydrogen atom or a group selected from: $C_1$-$C_3$-alkyl-, $C_1$-$C_3$-alkoxy-, halo-;

each of $R^{1b}$, $R^{1c}$, and $R^{1d}$ represents a hydrogen atom;

$R^2$ represents a halogen atom or a group selected from: $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, aryl-, cyano-, —$(CH_2)_q$—X—$(CH_2)_p$—$R^3$;

wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl- or aryl-group is optionally substituted, identically or differently, with 1, 2 or 3 $R^4$ groups;

X represents a bond or a bivalent group selected from: —O—, —S—, —S(═O)—, —S(═O)$_2$—, —S(═O)($NR^{3a}$)—, —($NR^{3a}$)—S(═O)—, —C(═O)—, —($NR^{3a}$)—, —C(═O)—O—, —O—C(═O)—, —C(═S)—O—, —O—C(═S)—, —C(═O)—($NR^{3a}$)—, —($NR^{3a}$)—C(═O)—, —($NR^{3a}$)—C(═O)—($NR^{3b}$)—, —O—C(═O)—($NR^{3a}$)—, —($NR^{3a}$)—C(═O)—O—;

$R^{3a}$, $R^{3b}$ are the same or different and are independently selected from $R^3$;

$R^3$ represents a hydrogen atom or a group selected from $C_1$-$C_6$-alkyl-, $C_3$-$C_6$-cycloalkyl-, aryl-;

wherein said $C_1$-$C_6$-alkyl-, $C_3$-$C_6$-cycloalkyl- or aryl-group is optionally substituted, identically or differently, with 1, 2 or 3 $R^4$ groups;

$R^4$ represents halo-, hydroxy-, oxo-(O═), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —C(═O)—$R^5$, —C(═O)—O—$R^5$, —O—C(═O)—$R^5$;

$R^5$ represents a hydrogen atom, a $C_1$-$C_6$-alkyl- or a $C_3$-$C_6$-cycloalkyl-group;

p represents an integer of 0, 1, 2 or 3;

q represents an integer of 0, 1, 2 or 3;

or a tautomer, an N-oxide, a hydrate, a solvate, or a salt thereof, or a mixture of same;

with the proviso that A is not

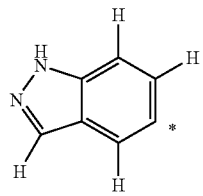

when R² is

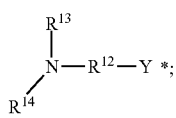

in which:
Y is a direct bond or a group selected from:
—O—, —C(=O)—, —S(=O)$_m$—, —N(R$^{18}$)—, —N(R$^{18}$)C(=O)—, —C(=O)N(R$^{18}$)—, —S(=O)$_m$N(R$^{18}$)—;
R$^{12}$ is a direct bond, an optionally substituted, straight or branched C$_1$-C$_{10}$-alkylene group, which is optionally interposed with a group N(R$^{15}$) where R$^{15}$ is hydrogen or a C$_1$-C$_3$-alkyl group;
R$^{13}$ and R$^{14}$ are independently selected from an optionally substituted C$_1$-C$_{10}$-alkyl-group, an optionally substituted C$_2$-C$_{10}$-alkenyl-group, an optionally substituted C$_2$-C$_{10}$-alkynyl-group or an optionally substituted heterocyclic group;
R$^{18}$ is hydrogen or an optionally substituted C$_1$-C$_4$-alkyl-group;
m is 0, 1 ort;
* indicates the point of attachment of said groups with the rest of the molecule;
or R$^{13}$ and R$^{14}$ together with the nitrogen atom to which they are attached form an optionally substituted heterocyclic ring, which optionally contains additional heteroatoms;
or R$^{13}$ together with R$^{12}$ or R$^{18}$ and the nitrogen atom(s) to which they are attached form an optionally substituted heterocyclic ring which optionally contains additional heteroatoms;
or R$^{13}$ and R$^{14}$ together with R$^{12}$ form an optionally substituted bridged ring structure;
or R$^{12}$ together with R$^{18}$ may form an optionally substituted cycloalkyl or heterocyclic ring.

It is to be understood that the present invention relates to any sub-combination within any embodiment or aspect of the present invention of compounds of general formula I, supra.

More particularly still, the present invention covers compounds of general formula I which are disclosed in the Examples section of this text, infra.

In accordance with another aspect, the present invention covers methods of preparing compounds of the present invention, said methods comprising the steps as described in the Experimental Section herein.

In a preferred embodiment, the present invention relates to a method of preparing compounds of general formula I, supra, in which method an intermediate compound of general formula III:

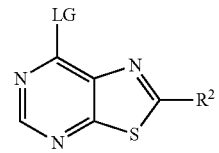

in which R² is as defined for general formula I, supra, and LG represents a leaving group;

is allowed to react with an intermediate compound of general formula II-A or II-B:

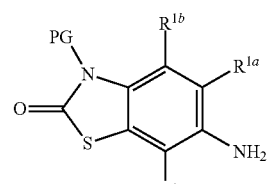

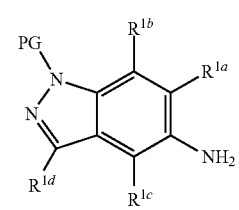

in which R$^{1a}$, R$^{1b}$, R$^{1c}$ and R$^{1d}$ are as defined for general formula I, supra, and PG represents a protective group or a hydrogen atom;

thus providing a compound of general formula I'-A, I'-B or I:

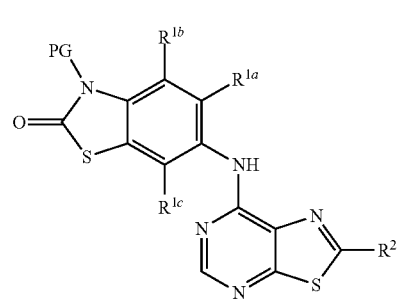

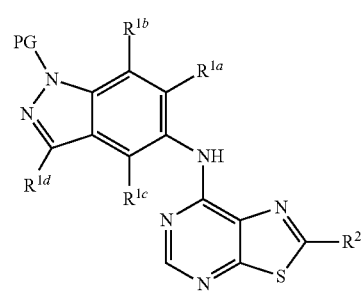

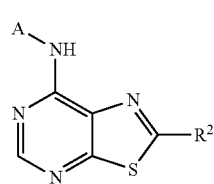

in which $R^{1a}$, $R^{1b}$, $R^{1c}$, $R^{1d}$, $R^2$, and A are as defined supra, and PG represents a protective group or a hydrogen atom.

In another aspect, the present invention also relates to intermediate compounds which are useful for the preparation of compounds of general formula I, supra. In a preferred embodiment, the intermediate compound is selected from the group consisting of:

7-Chloro-2-(cyclopropylmethyl)[1,3]thiazolo[5,4-d]pyrimidine,
7-Chloro-2-cyclobutyl[1,3]thiazolo[5,4-d]pyrimidine,
7-Chloro-2-cyclohexyl[1,3]thiazolo[5,4-d]pyrimidine,
2-Benzyl-7-chloro[1,3]thiazolo[5,4-d]pyrimidine,
7-Chloro-2-(methoxymethyl)[1,3]thiazolo[5,4-d]pyrimidine,
ethyl 4-(7-chloro[1,3]thiazolo[5,4-d]pyrimidin-2-yl)butanoate,
ethyl 3-(7-chloro[1,3]thiazolo[5,4-d]pyrimidin-2-yl)propanoate,
7-chloro-2-(2-phenylethyl)[1,3]thiazolo[5,4-d]pyrimidine,
2-[(benzyloxy)methyl]-7-chloro[1,3]thiazolo[5,4-d]pyrimidine,
N,N-dimethyl-7-(methylsulfonyl)[1,3]thiazolo[5,4-d]pyrimidine-2-carboxamide,
[7-(methylsulfonyl)[1,3]thiazolo[5,4-d]pyrimidin-2-yl](piperidin-1-yl)methanone,
N-[2-(dimethylamino)-2-oxoethyl]-N-methyl-7-(methylsulfonyl)[1,3]thiazolo[5,4-d]pyrimidine-2-carboxamide,
N-[3-(dimethylamino)-3-oxopropyl]-N-methyl-7-(methylsulfonyl)[1,3]thiazolo[5,4-d]pyrimidine-2-carboxamide.

In another aspect, the present invention relates to the use of an intermediate compound for the preparation of the compounds of general formula I, supra.

Synthesis of Compounds of General Formula I of the Present Invention

Compounds of general formulae I'-A, I'-B, II-A, II-B, III, IV, V and VI wherein $R^{1a}$, $R^{1b}$, $R^{1c}$, $R^{1d}$, $R^2$ and A have the meaning as given for general formula I, supra, $LG^1$ and $LG^2$ represent a leaving group LG and $PG^1$ and $PG^2$ represent a protective group or a hydrogen atom, can be synthesized according to the procedures depicted in Scheme 1.

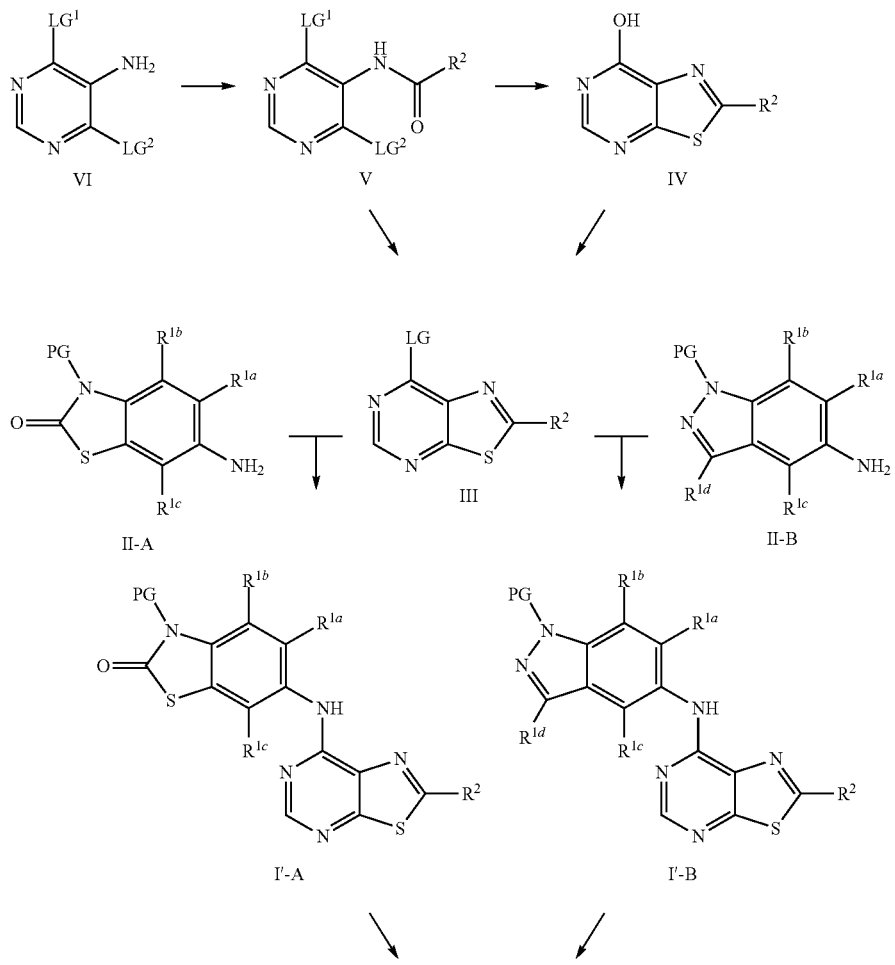

Scheme 1

-continued

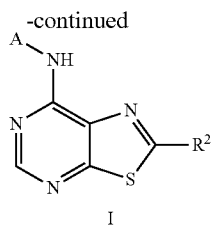
I

Scheme 1 exemplifies one route that allows variations and modifications in $R^2$ at different stages of the synthesis. However, also other routes may be used to synthesise the target compounds, in accordance with common general knowledge of a person skilled in the art of organic synthesis. The order of transformations exemplified in the Scheme is therefore not intended to be limiting. In addition, interconversion of any of the substituents, $R^{1a}$, $R^{1b}$, $R^{1c}$, $R^{1d}$, $R^2$ can be achieved before and/or after the exemplified transformations.

These modifications can be such as the introduction of protective groups (PG) like, for example, $PG^1$ and/or $PG^2$, cleavage of protective groups, reduction or oxidation of functional groups, halogenation, metallation, substitution or other reactions known to a person skilled in the art.

These transformations include those which introduce a functionality which allows for further interconversion of substituents. Appropriate protective groups and their introduction and cleavage are well-known to a person skilled in the art (see for example T. W. Greene and P. G. M. Wuts in Protective Groups in Organic Synthesis, 3$^{rd}$ edition, Wiley 1999). Specific examples are described in the subsequent paragraphs. Further, it is possible that two or more successive steps may be performed without work-up being performed between said steps, e.g. a "one-pot" reaction, as it is well-known to a person skilled in the art.

Compounds of formulae II-A, II-B, III, IV, V or VI are commercially available or can be synthesized according to procedures known to a person skilled in the art.

Compounds of formulae III, V or VI in which $LG^1$ and $LG^2$ are the same or different and represent a leaving group LG like, for example, a halogen atom as, for example, a chlorine or bromine atom may be commercially available or are obtained from compounds of formula IV by reacting the alcohol with a halogenation agent like, for example, phosphorus trichloride or phosphorus tribromide with or without an additional inert solvent as, for example, toluene at temperatures ranging from room temperature to the boiling point of the solvent, for example. Compounds of formula III in which LG represents a leaving group like, for example, an alkylsulfonate as, for example, methanesulfonate or trifluoromethanesulfonate or 1,1,2,2,3,3,4,4,4-nonafluorobutane-1-sulfonate or an arylsulfonate like, for example, benzenesulfonate or 4-methylbenzenesulfonate are obtained from compounds of formula IV by reacting the alcohol with a suitable alkylsulfonyl halide as, for example, methanesulfonyl chloride or trifluoromethanesulfonyl chloride or 1,1,2,2,3,3,4,4,4-nonafluorobutane-1-sulfonyl fluoride or by reacting the alcohol with a suitable arylsulfonyl halide as, for example, benzenesulfonyl chloride or 4-methylbenzenesulfonyl chloride in an inert solvent like, for example, tetrahydrofuran or toluene or dichloromethane optionally in the presence of a suitable base like, for example, triethylamine or pyridine or N,N-dimethylpyridin-4-amine at temperatures ranging from −40° C. to the boiling point of the solvent, for example.

Compounds of formula I'-A can be synthesized by reacting compounds of formula II-A with a compound of general formula III with $R^{1a}$, $R^{1b}$, $R^{1c}$ and $R^2$ as defined for general formula I. The amino group present in optionally substituted 6-amino-1,3-benzothiazol-2(3H)-one II-A displaces LG in compounds of general formula III to form amines of general formula I'-A or I.

Compounds of formula I'-B can be synthesized by reacting compounds of formula II-B with a compound of general formula III with $R^{1b}$, $R^{1c}$, $R^{1d}$ and $R^2$ as defined for general formula I. The amino group present in optionally substituted 5-amino-1H-indazole II-B displaces LG in compounds of general formula III to form amines of general formula I'-B or I.

Compounds of general formula III can be reacted with amines of formula II-A or II-B in which PG represents a protective group or a hydrogen atom optionally in the presence of an acid like, for example, hydrochloric acid in an inert solvent like, for example, ethanol or 1,4-dioxane at temperatures ranging from room temperature to the boiling point of the solvent, for example, to give compounds of general formula I'-A, I'-B or I.

The conversion of compounds of general formula I'-A or I'-B, in which PG represents a protective group, into compounds of the general formula I, can be accomplished by appropriate cleavage methods which are well-known to a person skilled in the art (see for example T. W. Greene and P. G. M. Wuts in Protective Groups in Organic Synthesis, 3$^{rd}$ edition, Wiley 1999).

Compounds of general formula I'-A, I'-B or I can also be built by Ullmann-type coupling reactions in the presence of suitable catalysts, such as, for example, copper based catalysts like copper(II)diacetate or copper(I)chloride in the presence of a suitable base, like for example, caesium carbonate starting from compounds of general formula II. Optionally, suitable ligands like N,N-dimethylglycine or phenyl hydrogen pyrrolidin-2-ylphosphonate can be added. The reaction can be performed at temperatures ranging from −40° C. to the boiling point of the solvent, for example. In a similar way, palladium catalysed amination reactions can be employed to form compounds of general formula I'-A, I'-B or I from compounds of formulae II-A or II-B with III; for a contemporary review on such aminations see e.g. David S. Surry and Stephen L Buchwald, Chem. Sci. 2011, 2, 27, and the literature cited therein.

Compounds of general formula I, I'-A, I'-B, II-A, II-B, III and IV in which $R^{1a}$, $R^{1b}$, $R^{1c}$, $R^{1d}$ and/or $R^2$ represent a halogen atom such as, for example, a chlorine, bromine or iodine atom, can be further modified via coupling reactions such as, for example Ullmann-, Negishi-, Suzuki- or Sonogashira-type coupling reactions. Said coupling reactions are performed in the presence of suitable catalysts, such as, for example, copper- or palladium based catalysts like, for example, copper(II)diacetate, copper(I)chloride, Palladium (II) acetate, tetrakis(triphenylphosphine)palladium (0), bis(triphenylphosphine)palladium (II) chloride or (1,1,-bis(diphenylphosphino) ferrocene)-dichloropalladium (II) and optionally suitable additives such as, for example, phosphines like, for example, P(oTol)₃ or triphenylphosphine and, and optionally with a suitable base, such as, for example, potassium carbonate, sodium 2-methylpropan-2-olate, tetrabutylammonium fluoride or tribasic potassium phosphate in a suitable solvent, such as, for example, tetrahydrofuran.

Examples of such coupling reactions may be found in the textbook entitled "Metal-Catalyzed Cross-Coupling Reactions", Armin de Meijere (Editor), François Diederich (Editor) September 2004, Wiley Interscience ISBN: 978-3-527-30518-6.

Compounds of general formulae I, I'-A, I'-B, II-A, II-B, III and IV in which $R^{1a}$, $R^{1b}$, $R^{1c}$, $R^{1d}$ and/or $R^2$ represent a halogen atom such as a fluorine, chlorine, bromine or iodine atom, can also be further modified via substitution reactions. Said halogen atoms in $R^{1a}$, $R^{1b}$, $R^{1c}$, $R^{1d}$ and/or $R^2$ can be substituted by nucleophiles like primary or secondary amines, alkoxides, thiolates or carbon anion bearing groups to add secondary or tertiary amines, ethers, thioethers or carbon attached groups. The reactions are performed in inert solvents like tetrahydrofuran.

Furthermore, residues in compounds of formulae I, I'-A, I'-B, II-A, II-B, III, IV and V can be optionally modified using, for example, oxidation-, reduction-, substitution- or elimination-reactions and conditions that are well known to a person skilled in the art of organic synthesis. For example, thioethers can be oxidized using oxidation reagents like 3-chlorobenzenecarboperoxoic acid, oxone or dimethyldioxirane in inert solvents like dichloromethane or acetone, respectively. Depending on the stoichiometric ratio of oxidation reagent to the aforementioned compounds sulfoxides or sulfones or mixtures thereof will be obtained.

Further, the compounds of formula I of the present invention can be converted to any salt as described herein, by any method which is known to the person skilled in the art. Similarly, any salt of a compound of formula I of the present invention can be converted into the free compound, by any method which is known to the person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallisation. In some cases, impurities may be removed by stirring using a suitable solvent. In some cases, the compounds may be purified by chromatography, particularly flash chromatography, using for example pre-packed silica gel cartridges, e.g. from Separtis such as Isolute® Flash silica gel or Isolute® Flash NH₂ silica gel in combination with a suitable chromatographic system such as an Isolera system (Biotage) and eluents such as, for example, gradients of hexane/ethyl acetate or dichloromethane/methanol. In some cases, the compounds may be purified by preparative HPLC using, for example, a Waters autopurifier equipped with a diode array detector and/or on-line electrospray ionisation mass spectrometer in combination with a suitable pre-packed reverse phase column and eluents such as, for example, gradients of water and acetonitrile which may contain additives such as trifluoroacetic acid, formic acid or aqueous ammonia.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "x HCl", "x CF₃COOH", "x Na⁺", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

EXAMPLES

Chemical naming of the examples and intermediates was performed using ACD software by ACD/LABS (Name Batch version 12.01.)

Example 1

6-{[2-(Cyclopropylmethyl)[1,3]thiazolo[5,4-d]pyrimidin-7-yl]amino}-1,3-benzothiazol-2(3H)-one

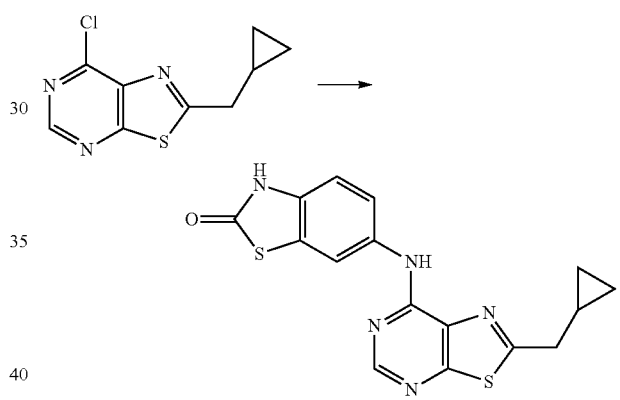

A mixture comprising 22 mg (97 μmol) 7-chloro-2-(cyclopropylmethyl)[1,3]thiazolo[5,4-d]pyrimidine (prepared according to intermediate example 1a), 16.2 mg 6-amino-1,3-benzothiazol-2(3H)-one, 0.5 mL ethanol and 5.5 μL hydrochloric acid (4M in dioxane) was reacted at 110° C. overnight. The crude product was purified by chromatography to give 16.1 mg (44%) of the title compound.

¹H-NMR (DMSO-d6): δ=0.39 (2H), 0.64 (2H), 1.20 (1H), 3.06 (2H), 7.09 (1H), 7.69 (1H), 8.09 (1H), 8.46 (1H), 10.04 (1H), 11.82 (1H) ppm.

Example 1a

7-Chloro-2-(cyclopropylmethyl)[1,3]thiazolo[5,4-d]pyrimidine

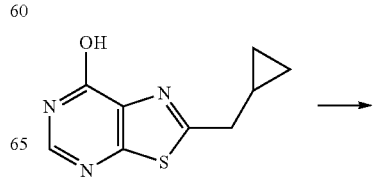

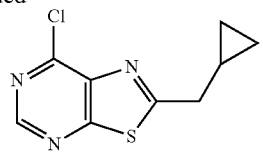

A mixture comprising 97 mg (468 μmol) 2-(cyclopropylmethyl)[1,3]thiazolo[5,4-d]pyrimidin-7-ol (prepared according to intermediate example 1b), and 2.6 mL phosphorus oxychloride was heated at 100° C. for 2.5 hours. Toluene was added and the solvents removed. The residue was purified by chromatography to give 50 mg (47%) of the title compound.

Example 1b 2-(Cyclopropylmethyl)[1,3]thiazolo[5,4-d]pyrimidin-7-ol

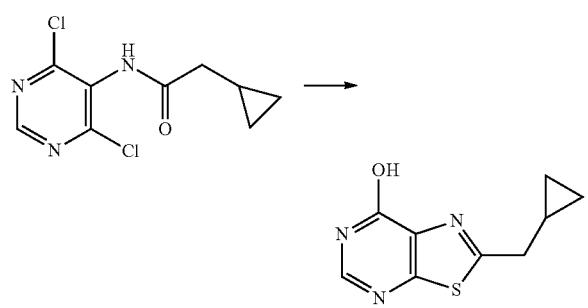

A mixture comprising 254 mg (1.03 mmol) 2-cyclopropyl-N-(4,6-dichloropyrimidin-5-yl)acetamide (prepared according to intermediate example 1c), 78.6 mg thiourea, 13.8 μL formic acid and 3.0 mL ethanol was heated at 90° C. for 12 hours. The precipitate was washed with water and diethyl ether to give 103 mg (48%) of the title compound.

Example 1c

2-Cyclopropyl-N-(4,6-dichloropyrimidin-5-yl)acetamide

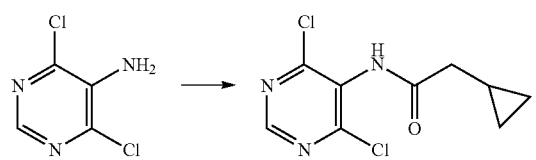 [SMILES: Nc1c(Cl)ncnc1Cl ; O=C(CC1CC1)Nc1c(Cl)ncnc1Cl]

A mixture comprising 500 mg (3.05 mmol) 4,6-dichloropyrimidin-5-amine (CAS-No 5413-85-4), 850 μL cyclopropylacetyl chloride and 2.0 mL tetrahydrofuran was heated at 60° C. for 2.5 days. Diethyl ether was added. The precipitate was filtered off and washed with diethyl ether to give 260 mg (35%) of the title compound.

Example 2

6-[(2-Cyclobutyl[1,3]thiazolo[5,4-d]pyrimidin-7-yl)amino]-1,3-benzothiazol-2(3H)-one 33 mg (146 μmol) 7-chloro-2-cyclobutyl[1,3]thiazolo[5,4-d]pyrimidine (prepared according to intermediate example 2a) were transformed in analogy to example 1 to give after working up and purification 36.8 mg (67%) of the title compound.
$^1$H-NMR (DMSO-d6): δ=1.95 (1H), 2.09 (1H), 2.36-2.52 (4H), 4.03 (1H), 7.09 (1H), 7.68 (1H), 8.08 (1H), 8.45 (1H), 9.94 (1H), 11.82 (1H) ppm.

Example 2a

7-Chloro-2-cyclobutyl[1,3]thiazolo[5,4-d]pyrimidine 208 mg (1.00 μmol) 2-cyclobutyl[1,3]thiazolo[5,4-d]pyrimidin-7-ol (prepared according to intermediate example 2b) were transformed in analogy to intermediate example 1a to give after working up and purification 110 mg (49%) of the title compound.

Example 2b

2-Cyclobutyl[1,3]thiazolo[5,4-d]pyrimidin-7-ol

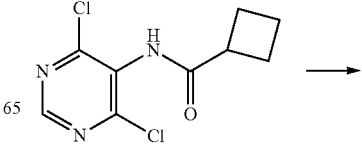

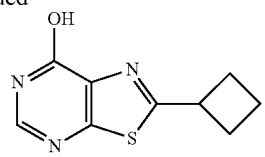

521 mg (2.12 mmol) N-(4,6-dichloropyrimidin-5-yl)cyclobutanecarboxamide (prepared according to intermediate example 2c) were transformed in analogy to intermediate example 1b to give after working up and purification 215 mg (49%) of the title compound.

Example 2c

N-(4,6-Dichloropyrimidin-5-yl)cyclobutanecarboxamide

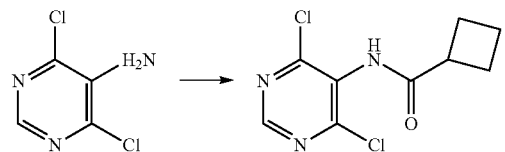 [SMILES: Nc1c(Cl)ncnc1Cl ; O=C(Nc1c(Cl)ncnc1Cl)C1CCC1]

500 mg (3.05 mmol) 4,6-dichloropyrimidin-5-amine (CAS-No 5413-85-4) were transformed in analogy to intermediate example 1c using cyclobutanecarbonyl chloride to give after working up and purification 528 mg (70%) of the title compound.

Example 3

6-[(2-Cyclohexyl[1,3]thiazolo[5,4-d]pyrimidin-7-yl)amino]-1,3-benzothiazol-2(3H)-one

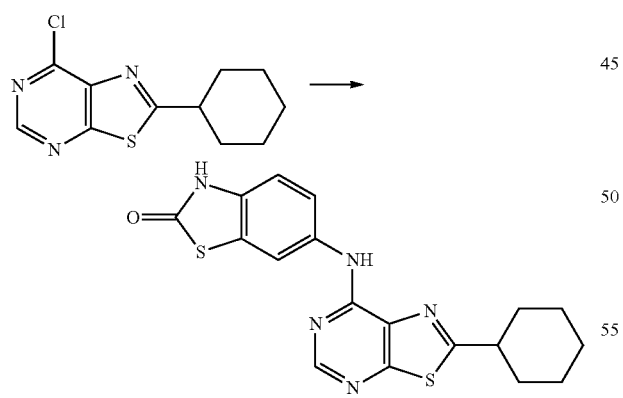

33 mg (130 µmol) 7-chloro-2-cyclohexyl[1,3]thiazolo[5,4-d]pyrimidine (prepared according to intermediate example 3a) were transformed in analogy to example 1 to give after working up and purification 38.5 mg (73%) of the title compound.

$^{1}$H-NMR (DMSO-d6): δ=1.27 (1H), 1.42 (2H), 1.59 (2H), 1.70 (1H), 1.82 (2H), 2.13 (2H), 3.14 (1H), 7.10 (1H), 7.67 (1H), 8.07 (1H), 8.45 (1H), 9.89 (1H), 11.82 (1H) ppm.

Example 3a

7-Chloro-2-cyclohexyl[1,3]thiazolo[5,4-d]pyrimidine

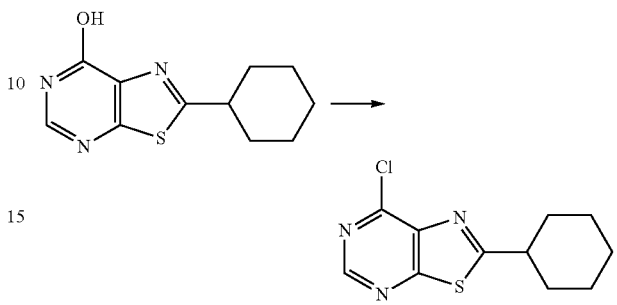

156 mg (663 µmol) 2-cyclohexyl[1,3]thiazolo[5,4-d]pyrimidin-7-ol (prepared according to intermediate example 3b) were transformed in analogy to intermediate example 1a to give after working up and purification 112 mg (67%) of the title compound.

Example 3b

2-Cyclohexyl[1,3]thiazolo[5,4-d]pyrimidin-7-ol

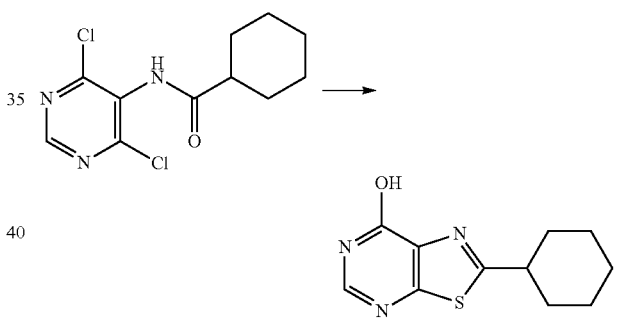

415 mg (1.51 mmol) N-(4,6-dichloropyrimidin-5-yl)cyclohexanecarboxamide (prepared according to intermediate example 3c) were transformed in analogy to intermediate example 1 b to give after working up and purification 163 mg (46%) of the title compound.

Example 3c

N-(4,6-Dichloropyrimidin-5-yl)cyclohexanecarboxamide

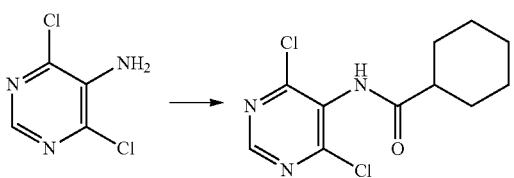 [SMILES: Nc1c(Cl)ncnc1Cl ; O=C(Nc1c(Cl)ncnc1Cl)C1CCCCC1]

500 mg (3.05 mmol) 4,6-dichloropyrimidin-5-amine (CAS-No 5413-85-4) were transformed in analogy to intermediate example 1c using cyclohexanecarbonyl chloride to give after working up and purification 421 mg (50%) of the title compound.

Example 4

2-Benzyl-N-(6-methoxy-1H-indazol-5-yl)[1,3]thiazolo[5,4-d]pyrimidin-7-amine

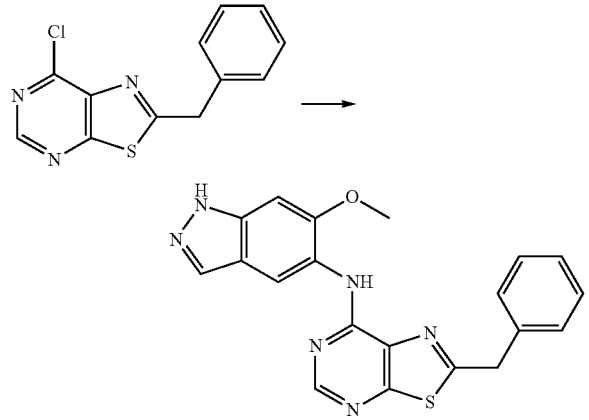

35 mg (134 µmol) 2-benzyl-7-chloro[1,3]thiazolo[5,4-d]pyrimidine (prepared according to intermediate example 4a) were transformed in analogy to example 1 using 6-methoxy-1H-indazol-5-amine to give after working up and purification 7.2 mg (13%) of the title compound.

¹H-NMR (DMSO-d6): δ=3.93 (3H), 4.52 (2H), 7.10 (1H), 7.33 (1H), 7.35-7.44 (4H), 8.00 (1H), 8.49 (1H), 8.52 (1H), 8.95 (1H), 12.87 (1H) ppm.

Example 4a

2-Benzyl-7-chloro[1,3]thiazolo[5,4-d]pyrimidine

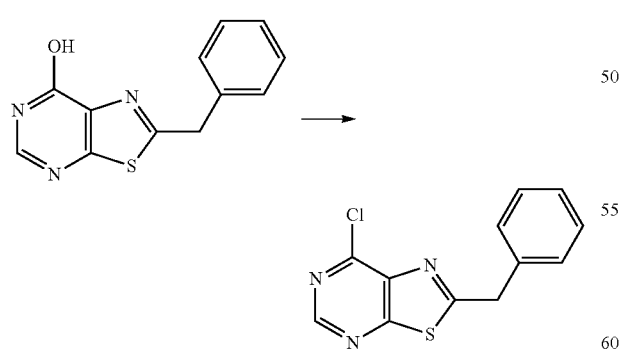

170 mg (699 µmol) 2-benzyl[1,3]thiazolo[5,4-d]pyrimidin-7-ol (prepared according to intermediate example 4b) were transformed in analogy to intermediate example 1b to give after working up and purification 73.9 mg (40%) of the title compound.

Example 4b

2-Benzyl[1,3]thiazolo[5,4-d]pyrimidin-7-ol

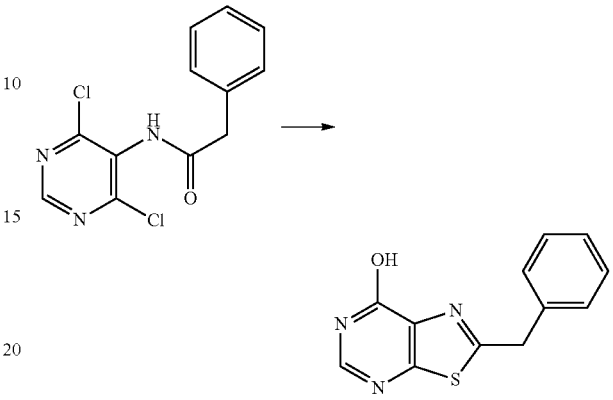

505 mg (1.79 mmol) N-(4,6-dichloropyrimidin-5-yl)-2-phenylacetamide (prepared according to intermediate example 4c) were transformed in analogy to intermediate example 1 b to give after working up and purification 176 mg (40%) of the title compound.

Example 4c

N-(4,6-Dichloropyrimidin-5-yl)-2-phenylacetamide 500 mg (3.05 mmol) 4,6-dichloropyrimidin-5-amine (CAS-No 5413-85-4) were transformed in analogy to intermediate example 1c using phenylacetyl chloride to give after working up and purification 512 mg (60%) of the title compound.

Example 5

N-(6-Methoxy-1H-indazol-5-yl)-2-(methoxymethyl)[1,3]thiazolo[5,4-d]pyrimidin-7-amine -continued

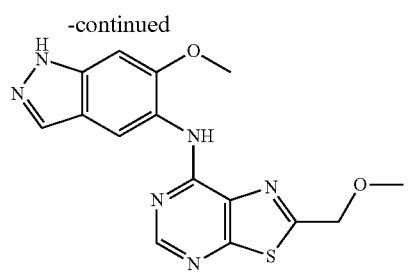

16 mg (74 μmol) 7-chloro-2-(methoxymethyl)[1,3]thiazolo[5,4-d]pyrimidine (prepared according to intermediate example 5a) were transformed in analogy to example 1 using 6-methoxy-1H-indazol-5-amine to give after working up and purification 12.3 mg (46%) of the title compound.

¹H-NMR (DMSO-d6): δ=3.48 (3H), 3.93 (3H), 4.88 (2H), 7.10 (1H), 8.00 (1H), 8.51 (1H), 8.53 (1H), 8.97 (1H), 12.87 (1H) ppm.

Example 5a

7-Chloro-2-(methoxymethyl)[1,3]thiazolo[5,4-d]pyrimidine

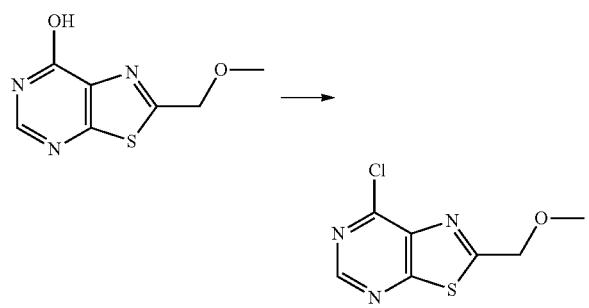

225 mg (1.14 mmol) 2-(methoxymethyl)[1,3]thiazolo[5,4-d]pyrimidin-7-ol (prepared according to intermediate example 5b) were transformed in analogy to intermediate example 1a to give after working up and purification 16 mg (7%) of the title compound.

Example 5b 2-(Methoxymethyl)[1,3]thiazolo[5,4-d]pyrimidin-7-ol

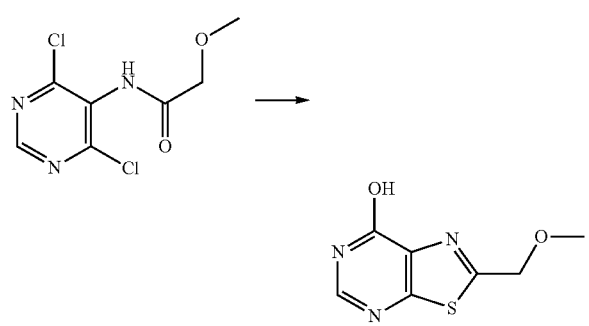

525 mg (2.22 mmol) N-(4,6-dichloropyrimidin-5-yl)-2-methoxyacetamide (prepared according to intermediate example 5c) were transformed in analogy to intermediate example 1b to give after working up and purification 233.5 mg (53%) of the title compound.

Example 5c

N-(4,6-Dichloropyrimidin-5-yl)-2-methoxyacetamide

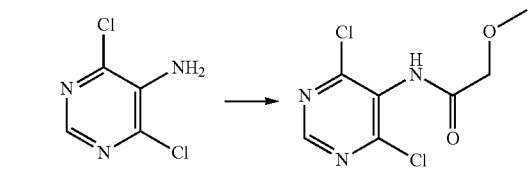

500 mg (3.05 mmol) 4,6-dichloropyrimidin-5-amine (CAS-No 5413-85-4) were transformed in analogy to intermediate example 1c using methoxyacetyl chloride to give after working up and purification 531 mg (74%) of the title compound.

Example 6

6-[(2-Cyclobutyl[1,3]thiazolo[5,4-d]pyrimidin-7-yl)amino]-5-methoxy-1,3-benzothiazol-2(3H)-one

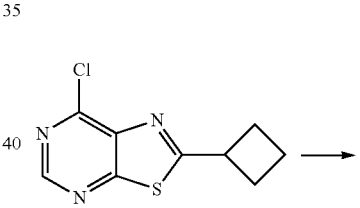

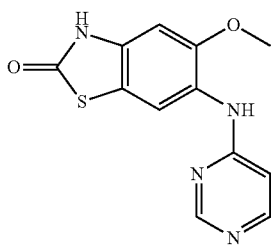

33 mg (146 μmol) 7-chloro-2-cyclobutyl[1,3]thiazolo[5,4-d]pyrimidine (prepared according to intermediate example 2a) were transformed in analogy to example 1 using 6-amino-5-methoxy-1,3-benzothiazol-2(3H)-one to give after working up and purification 10.5 mg (19%) of the title compound.

¹H-NMR (DMSO-d6): δ=1.95-2.17 (2H), 2.36-2.58 (4H), 3.89 (3H), 4.02 (1H), 6.88 (1H), 8.32 (1H), 8.47 (1H), 8.67 (1H), 11.51 (1H) ppm.

Example 7

6-[(2-Cyclohexyl[1,3]thiazolo[5,4-d]pyrimidin-7-yl)amino]-5-methoxy-1,3-benzothiazol-2(3H)-one

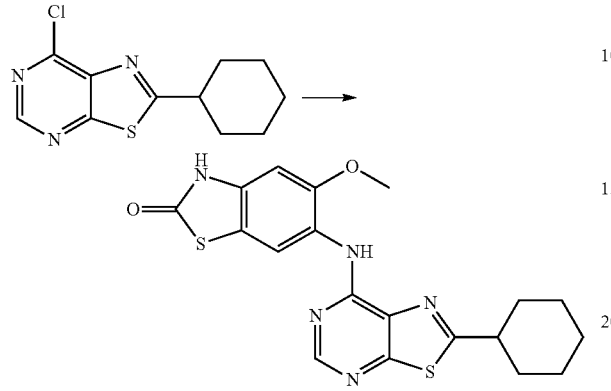

33 mg (130 µmol) 7-chloro-2-cyclohexyl[1,3]thiazolo[5,4-d]pyrimidine (prepared according to intermediate example 3a) were transformed in analogy to example 1 using 6-amino-5-methoxy-1,3-benzothiazol-2(3H)-one to give after working up and purification 14.8 mg (25%) of the title compound.

¹H-NMR (DMSO-d6): δ=1.22-1.87 (8H), 2.13 (2H), 3.14 (1H), 3.85 (3H), 6.82 (1H), 8.21 (1H), 8.44 (1H), 8.88 (1H), 11.84 (1H) ppm.

Example 8

2-Cyclohexyl-N-(1H-indazol-5-yl)[1,3]thiazolo[5,4-d]pyrimidin-7-amine

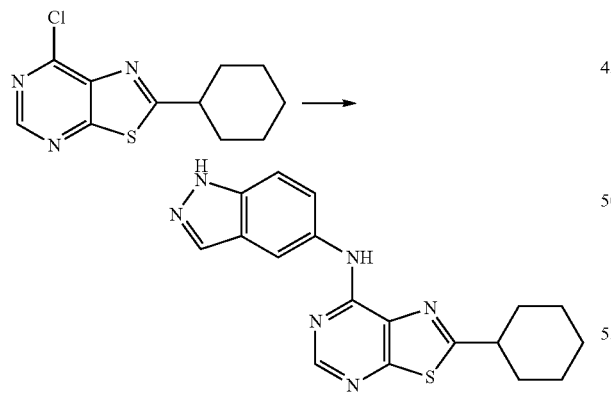

33 mg (130 µmol) 7-chloro-2-cyclohexyl[1,3]thiazolo[5,4-d]pyrimidine (prepared according to intermediate example 3a) were transformed in analogy to example 1 using 1H-indazol-5-amine to give after working up and purification 23.8 mg (50%) of the title compound.

¹H-NMR (DMSO-d6): δ=1.20-1.76 (6H), 1.85 (1H), 1.81 (1H), 2.17 (1H), 2.13 (1H), 3.15 (1H), 7.51 (1H), 7.70 (1H), 8.05 (1H), 8.24 (1H), 8.44 (1H), 9.84 (1H), 12.99 (1H) ppm.

Example 9

2-(Cyclopropylmethyl)-N-(1H-indazol-5-yl)[1,3]thiazolo[5,4-d]pyrimidin-7-amine

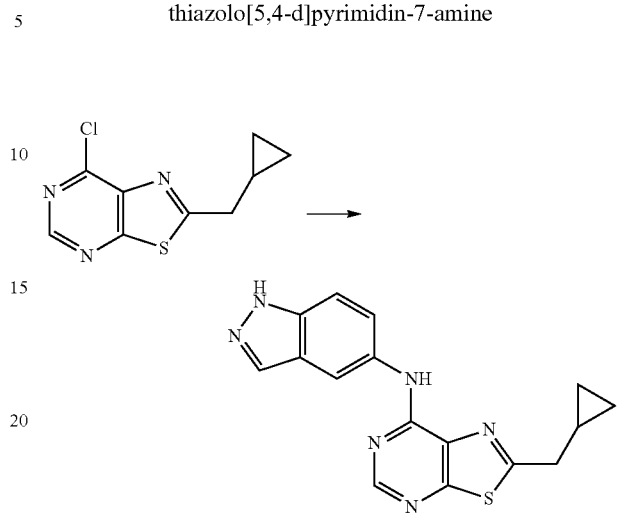

22 mg (97 µmol) 7-chloro-2-(cyclopropylmethyl)[1,3]thiazolo[5,4-d]pyrimidine (prepared according to intermediate example 1a) using 1H-indazol-5-amine to give after working up and purification 15.8 mg (48%) of the title compound.

¹H-NMR (DMSO-d6): δ=0.40 (2H), 0.64 (2H), 1.21 (1H), 3.06 (2H), 7.51 (1H), 7.72 (1H), 8.05 (1H), 8.26 (1H), 8.46 (1H), 10.00 (1H), 13.00 (1H) ppm.

Example 10

2-Cyclobutyl-N-(1H-indazol-5-yl)[1,3]thiazolo[5,4-d]pyrimidin-7-amine

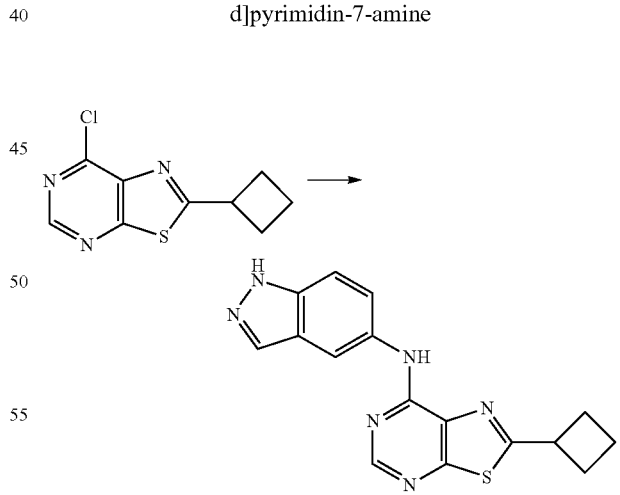

33 mg (146 µmol) 2-cyclobutyl[1,3]thiazolo[5,4-d]pyrimidin-7-ol (prepared according to intermediate example 2b) using 1H-indazol-5-amine to give after working up and purification 29.5 mg (59%) of the title compound.

¹H-NMR (DMSO-d6): δ=1.96 (1H), 2.09 (1H), 2.36-2.54 (4H), 4.04 (1H), 7.51 (1H), 7.71 (1H), 8.05 (1H), 8.24 (1H), 8.44 (1H), 9.90 (1H), 12.99 (1H) ppm.

Example 11

2-Benzyl-N-(1H-indazol-5-yl)[1,3]thiazolo[5,4-d]pyrimidin-7-amine

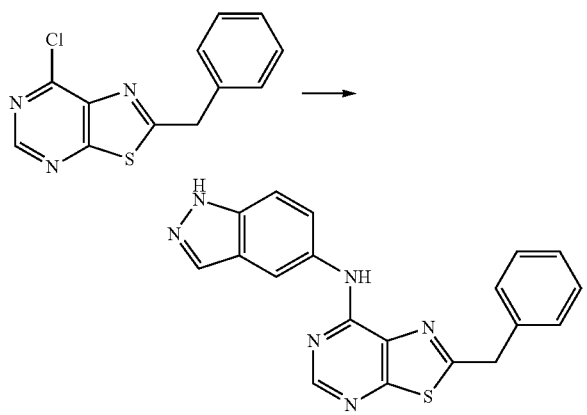

35 mg (134 μmol) 2-benzyl-7-chloro[1,3]thiazolo[5,4-d]pyrimidine (prepared according to intermediate example 4a) using 1H-indazol-5-amine to give after working up and purification 8.6 mg (17%) of the title compound.

$^1$H-NMR (DMSO-d6): δ=4.53 (2H), 7.28-7.46 (5H), 7.51 (1H), 7.73 (1H), 8.06 (1H), 8.26 (1H), 8.44 (1H), 10.12 (1H), 13.02 (1H) ppm.

Example 12

1-(3-Hydroxy-3-methylazetidin-1-yl)-4-[7-(1H-indazol-5-ylamino)[1,3]thiazolo[5,4-d]pyrimidin-2-yl]butan-1-one

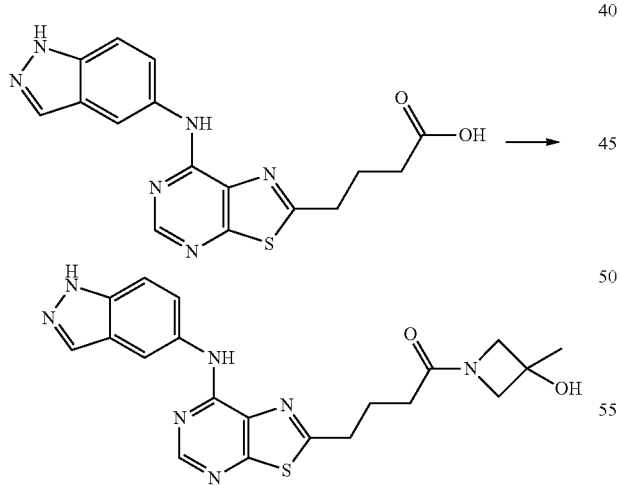

A mixture comprising 35 mg (99 μmol) 4-[7-(1H-indazol-5-ylamino)[1,3]thiazolo[5,4-d]pyrimidin-2-yl]butanoic acid (prepared according to intermediate example 12a), 1.7 mL N,N-dimethylformamide, 48.8 mg 3-methylazetidin-3-ol, 176 μL 2,4,6-tripropyl-1,3,5,2,4,6-trioxatriphosphinane 2,4,6-trioxide solution (50% in ethyl acetate) and 206 μL N-ethyl-N-isopropylpropan-2-amine was stirred at 40° C. overnight. Water was added, the solution was neutralized by addition of sodium hydroxide solution, the solvents were removed and the residue purified by chromatography to give 18.8 mg (43%) of the title compound.

$^1$H-NMR (DMSO-d6): δ=1.34 (3H), 2.02 (2H), 2.21 (2H), 3.16 (2H), 3.62-3.71 (2H), 3.91 (2H), 5.61 (1H), 7.51 (1H), 7.72 (1H), 8.06 (1H), 8.26 (1H), 8.45 (1H), 9.99 (1H), 13.01 (1H) ppm.

Example 12a

4-[7-(1H-Indazol-5-ylamino)[1,3]thiazolo[5,4-d]pyrimidin-2-yl]butanoic acid

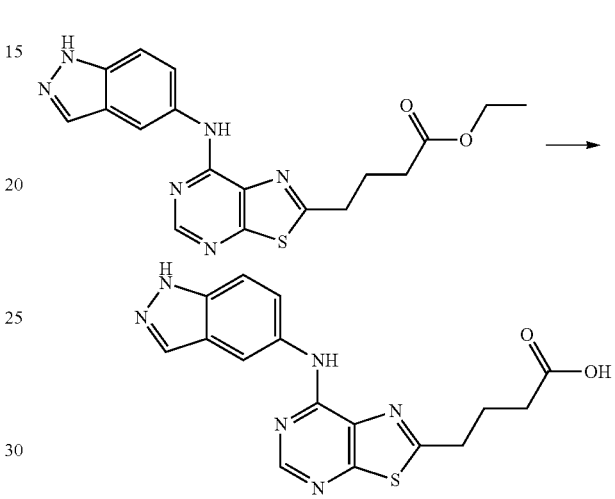

A mixture of 79 mg (207 μmol) ethyl 4-[7-(1H-indazol-5-ylamino)[1,3]thiazolo[5,4-d]pyrimidin-2-yl]butanoate (prepared according to intermediate example 12b), 1.2 mL methanol, 3.7 mL tetrahydrofurane and 1.24 mL aqueous lithium hydroxide (1 molar) was stirred at room temperature overnight. The mixture was acidified by addition of aqueous hydrochloric acid (4M) and extracted with dichloromethane. The organic layer was washed with brine and dried over sodium sulfate. After filtration and removal of the solvent, 72 mg (98%) of the title compound were isolated.

Example 12b

Indazol-5-ylamino)[1,3]thiazolo[5,4-d]pyrimidin-2-yl]butanoate

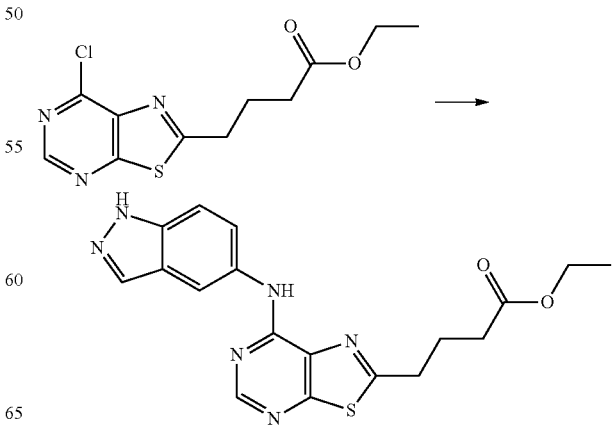

120 mg (420 µmol) ethyl 4-(7-chloro[1,3]thiazolo[5,4-d]pyrimidin-2-yl)butanoate (prepared according to intermediate example 12c) were transformed in analogy to example 1 using 1H-indazol-5-amine to give after working up and purification 82 mg (51%) of the title compound.

Example 12c

Ethyl 4-(7-chloro[1,3]thiazolo[5,4-d]pyrimidin-2-yl)butanoate

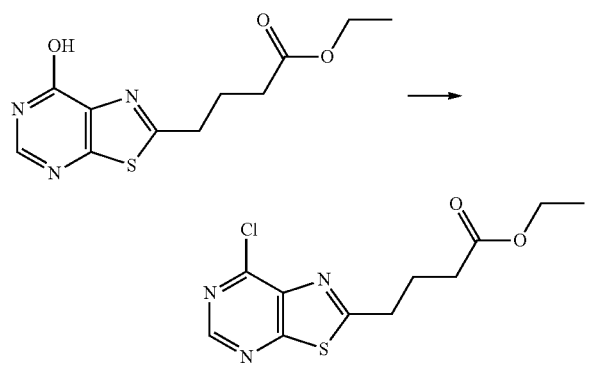

370 mg (1.38 mmol) ethyl 4-(7-hydroxy[1,3]thiazolo[5,4-d]pyrimidin-2-yl)butanoate (prepared according to intermediate example 12d) were transformed in analogy to intermediate example 1a to give after working up and purification 170 mg (43%) of the title compound.

Example 12d

Ethyl 4-(7-hydroxy[1,3]thiazolo[5,4-d]pyrimidin-2-yl)butanoate

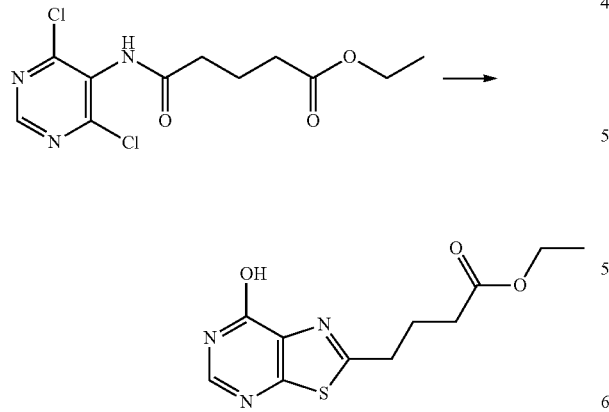

769 mg (2.63 mmol) ethyl 5-[(4,6-dichloropyrimidin-5-yl)amino]-5-oxopentanoate (prepared according to intermediate example 12e) were transformed in analogy to intermediate example 1b to give after working up and purification 380 mg (54%) of the title compound.

Example 12e

Ethyl 5-[(4,6-dichloropyrimidin-5-yl)amino]-5-oxopentanoate

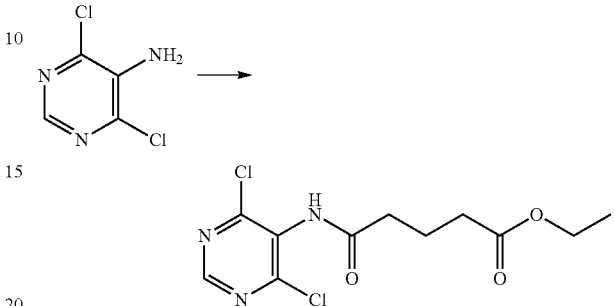

1.00 g (6.10 mmol) 4,6-dichloropyrimidin-5-amine (CAS-No. 5413-85-4) were transformed in analogy to intermediate example 1c using methyl 5-chloro-5-oxopentanoate to give after working up and purification 774 mg (43%) of the title compound.

Example 13

4-[7-(1H-Indazol-5-ylamino)[1,3]thiazolo[5,4-d]pyrimidin-2-yl]-N,N-dimethylbutanamide

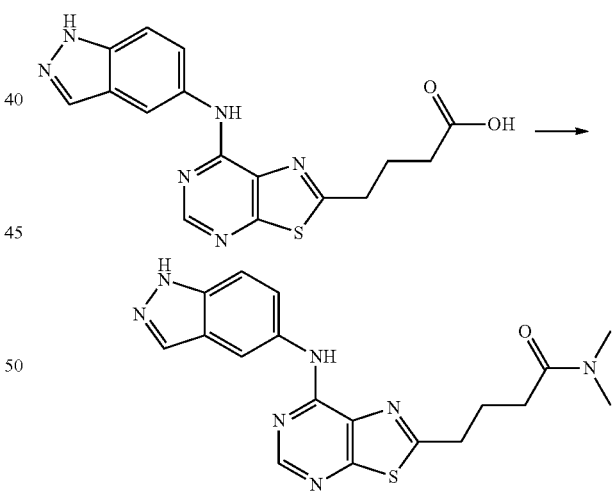

35 mg (99 µmol) 4-[7-(1H-indazol-5-ylamino)[1,3]thiazolo[5,4-d]pyrimidin-2-yl]butanoic acid (prepared according to intermediate example 12a) were transformed in analogy to example 12 using N-methylmethanamine to give after working up and purification 19.6 mg (49%) of the title compound.

$^1$H-NMR (DMSO-d6): δ=2.04 (2H), 2.45 (2H), 2.81 (3H), 2.94 (3H), 3.18 (2H), 7.51 (1H), 7.72 (1H), 8.06 (1H), 8.25 (1H), 8.45 (1H), 10.00 (1H), 13.01 (1H) ppm.

Example 14

1-(3-Hydroxy-3-methylazetidin-1-yl)-3-[7-(1H-indazol-5-ylamino)[1,3]thiazolo[5,4-d]pyrimidin-2-yl]propan-1-one

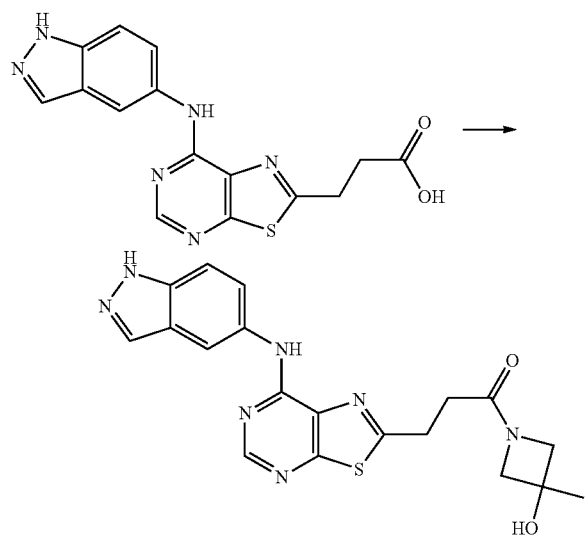

40 mg (118 μmol) 3-[7-(1H-indazol-5-ylamino)[1,3]thiazolo[5,4-d]pyrimidin-2-yl]propanoic acid (prepared according to intermediate example 14a) were transformed in analogy to example 12 to give after working up and purification 13.2 mg (25%) of the title compound.

$^1$H-NMR (DMSO-d6): δ=1.33 (3H), 2.68 (2H), 3.35 (2H), 3.69 (2H), 3.97 (2H), 5.65 (1H), 7.51 (1H), 7.70 (1H), 8.06 (1H), 8.24 (1H), 8.45 (1H), 9.95 (1H), 13.02 (1H) ppm.

Example 14a

3-[7-(1H-Indazol-5-ylamino)[1,3]thiazolo[5,4-d]pyrimidin-2-yl]propanoic acid

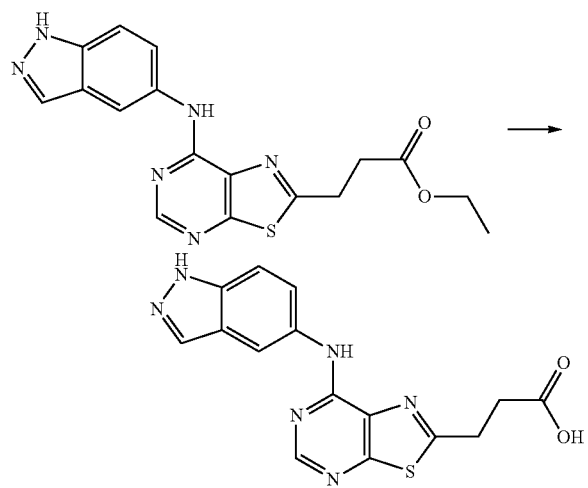

101 mg (274 μmol) ethyl 3-[7-(1H-indazol-5-ylamino)[1,3]thiazolo[5,4-d]pyrimidin-2-yl]propanoate (prepared according to intermediate example 14b) were transformed in analogy to intermediate example 12a to give after working up and purification 83 mg (89%) of the title compound.

Example 14b

Ethyl 3-[7-(1H-indazol-5-ylamino)[1,3]thiazolo[5,4-d]pyrimidin-2-yl]propanoate

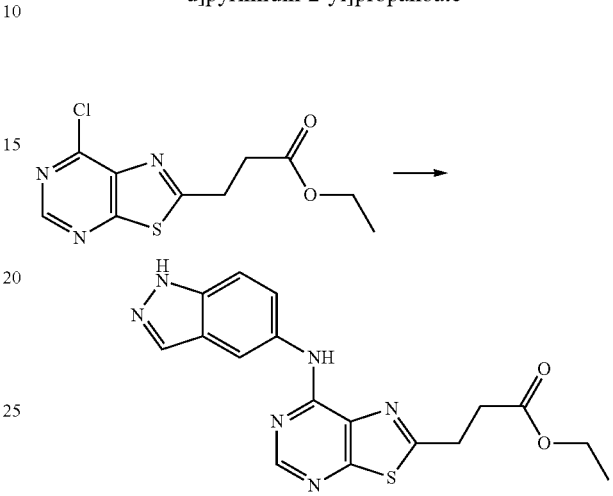

108 mg (397 μmol) ethyl 3-(7-chloro[1,3]thiazolo[5,4-d]pyrimidin-2-yl)propanoate (prepared according to intermediate example 14c) were transformed in analogy to example 1 using 1H-indazol-5-amine to give after working up and purification 106 mg (72%) of the title compound.

Example 14c

Ethyl 3-(7-chloro[1,3]thiazolo[5,4-d]pyrimidin-2-yl)propanoate

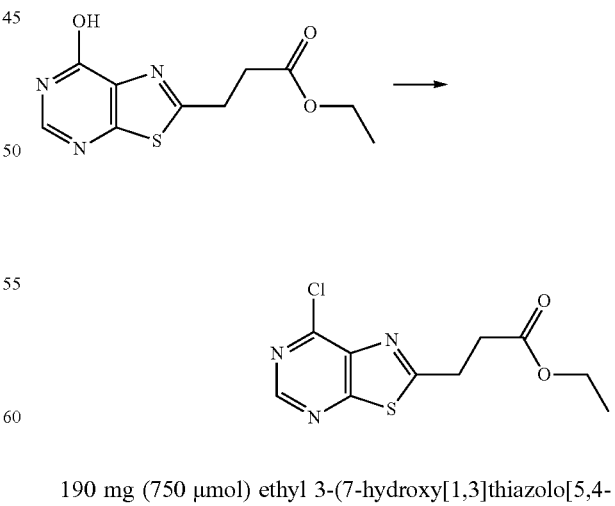

190 mg (750 μmol) ethyl 3-(7-hydroxy[1,3]thiazolo[5,4-d]pyrimidin-2-yl)propanoate (prepared according to intermediate example 14d) were transformed in analogy to intermediate example 1a to give after working up and purification 113 mg (55%) of the title compound.

Example 14d

Ethyl 3-(7-hydroxy[1,3]thiazolo[5,4-d]pyrimidin-2-yl)propanoate

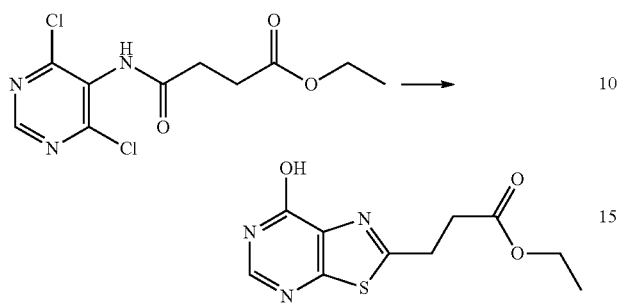

540 mg (1.94 mmol) ethyl 4-[(4,6-dichloropyrimidin-5-yl)amino]-4-oxobutanoate (prepared according to intermediate example 14e) were transformed in analogy to intermediate example 1b to give after working up and purification 204 mg (41%) of the title compound.

Example 14e

Ethyl 4-[(4,6-dichloropyrimidin-5-yl)amino]-4-oxobutanoate

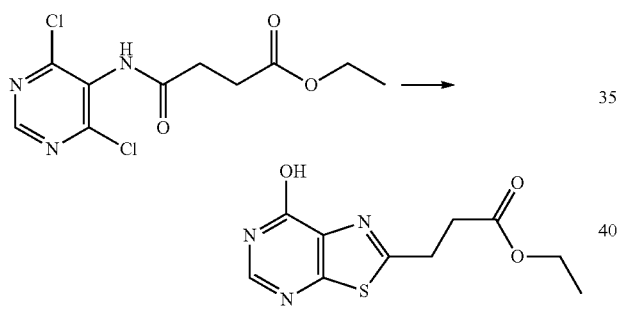

1.00 g (6.10 mmol) 4,6-dichloropyrimidin-5-amine (CAS-No. 5413-85-4) were transformed in analogy to intermediate example 1c using ethyl 4-chloro-4-oxobutanoate to give after working up and purification 545 mg (32%) of the title compound.

Example 15

N-(6-Methoxy-1H-indazol-5-yl)[1,3]thiazolo[5,4-d]pyrimidin-7-amine

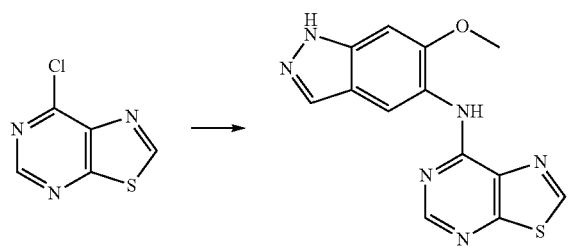 [SMILES: Clc1ncnc2scnc12 ; COc1cc2[nH]ncc2cc1Nc1ncnc2scnc12]

50 mg (291 µmol) 7-chloro[1,3]thiazolo[5,4-d]pyrimidine (CAS-No. 13316-12-6) were transformed in analogy to example 1 using 6-methoxy-1H-indazol-5-amine (CAS-No 749223-61-8) to give after working up and purification 11.4 mg (12%) of the title compound.

$^1$H-NMR (DMSO-d6): δ=3.95 (3H), 7.11 (1H), 8.01 (1H), 8.55-8.62 (2H), 9.09 (1H), 9.39 (1H), 12.88 (1H) ppm.

Example 16

N-(1H-Indazol-5-yl)[1,3]thiazolo[5,4-d]pyrimidin-7-amine

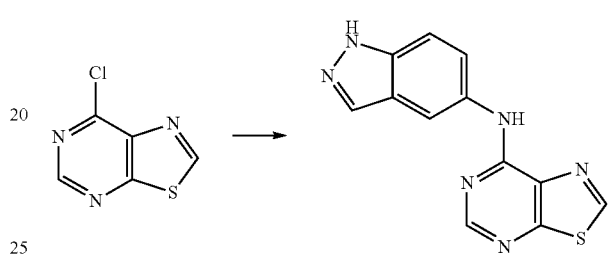

50 mg (291 µmol) 7-chloro[1,3]thiazolo[5,4-d]pyrimidine (CAS-No. 13316-12-6) were transformed in analogy to example 1 using 1H-indazol-5-amine to give after working up and purification 30.3 mg (37%) of the title compound.

$^1$H-NMR (DMSO-d6): δ=7.52 (1H), 7.74 (1H), 8.06 (1H), 8.29 (1H), 8.53 (1H), 9.38 (1H), 10.20 (1H), 13.02 (1H) ppm.

Example 17

2-(2-Phenylethyl)-N-[6-(propan-2-yloxy)-1H-indazol-5-yl][1,3]thiazolo[5,4-d]pyrimidin-7-amine

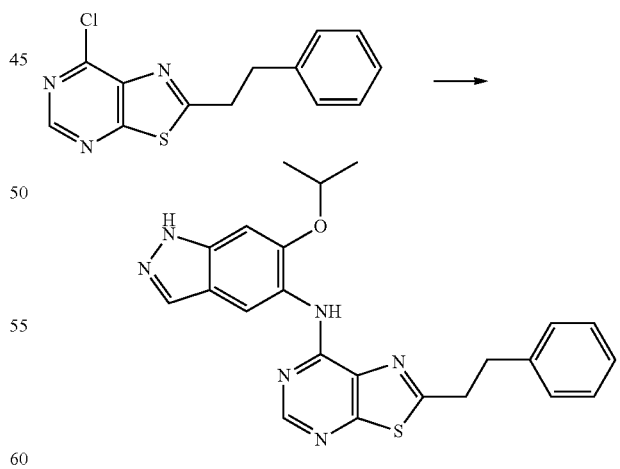

15 mg (54 µmol) 7-chloro-2-(2-phenylethyl)[1,3]thiazolo[5,4-d]pyrimidine (prepared according to intermediate example 17a) were transformed in analogy to example 1 using 6-isopropoxy-1H-indazol-5-amine (prepared according to intermediate example 17d) to give after working up and purification 8.7 mg (35%) of the title compound.

¹H-NMR (DMSO-d6): δ=1.36 (6H), 3.18 (2H), 3.49 (2H), 4.79 (1H), 7.14 (1H), 7.16-7.33 (5H), 8.01 (1H), 8.56 (1H), 8.73 (1H), 8.98 (1H), 12.82 (1H) ppm.

Example 17a

7-Chloro-2-(2-phenylethyl)[1,3]thiazolo[5,4-d]pyrimidine

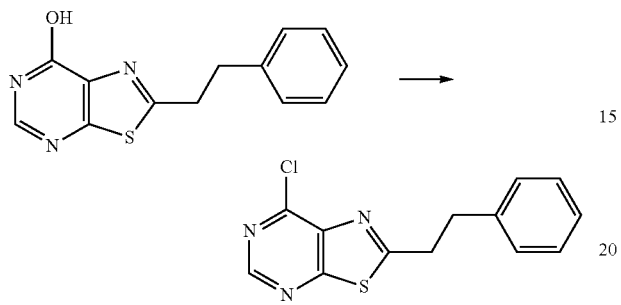

485 mg (1.89 mmol) (prepared according to intermediate example 17b) were transformed in analogy to intermediate example 7a to give after working up and purification 226 mg (43%) of the title compound.

Example 17b 2-(2-Phenylethyl)[1,3]thiazolo[5,4-d]pyrimidin-7-ol

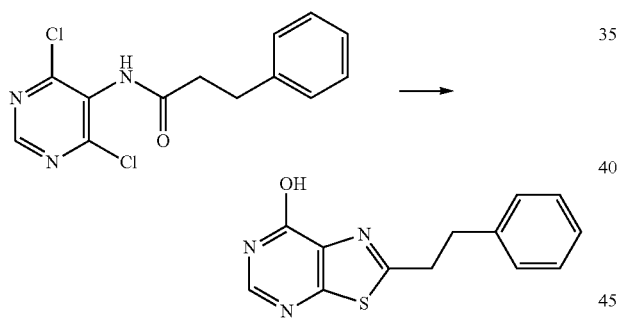

A mixture comprising 789 mg (2.66 mmol) N-(4,6-dichloropyrimidin-5-yl)-3-phenylpropanamide (prepared according to intermediate example 17c), 7.5 mL ethanol, 203 mg thiourea and 35.7 μL formic acid was heated at 90° C. for 12 hours. The formed precipitate was washed with ethanol and diethylether and purified by chromatography to give 230 mg (34%) of the title compound.

Example 17c

N-(4,6-Dichloropyrimidin-5-yl)-3-phenylpropanamide

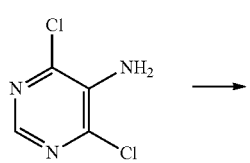

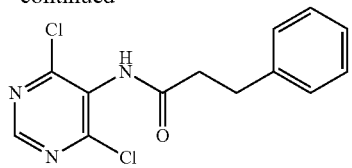

A mixture comprising 1.00 g (6.10 mmol) 4,6-dichloropyrimidin-5-amine (CAS-No. 5413-85-4), 4 mL tetrahydrofurane and 1.82 mL 3-phenylpropanoyl chloride was heated at 70° C. overnight. Dichloromethane and methanol were added the solvents removed and the residue was purified by chromatography to give 794 mg (44%) of the title compound.

Example 17d

6-Isopropoxy-1H-indazol-5-amine

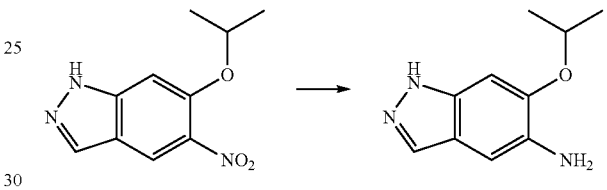

A mixture comprising 5.0 g (22.6 mmol) 6-isopropoxy-5-nitro-1H-indazole (purchased from Tractus chemicals, Unit 5, 3/F Harry Industrial Building; 4951 Au Pui Wan Street, Fo Tan; Shatin, New Territories; Hong Kong; Email: contact@tractuschem.com), 100 mL ethanol and 601 mg palladium on charcoal (10%) was heavily stirred under an atmosphere of hydrogen overnight. After filtration and removal of the solvent, the residue was washed with diethyl ether to give 3.64 g (80%) of the title compound.

Example 18

5-Methoxy-6-([1,3]thiazolo[5,4-d]pyrimidin-7-ylamino)-1,3-benzothiazol-2(3H)-one

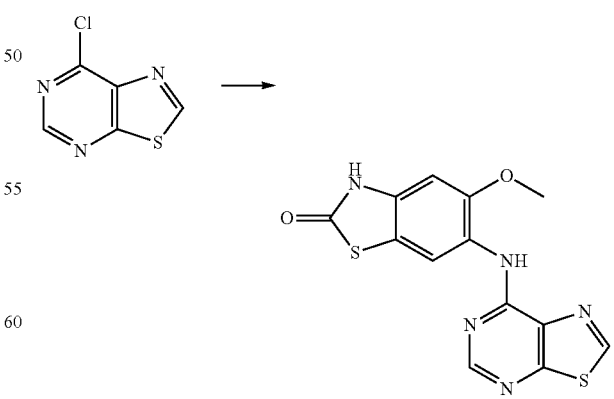

50 mg (291 μmol) 7-chloro[1,3]thiazolo[5,4-d]pyrimidine (CAS-No. 13316-12-6) were transformed in analogy to example 1 using 6-amino-5-methoxy-1,3-benzothiazol-2

(3H)-one (prepared according to intermediate example 18a) to give after working up and purification 68.1 mg (67%) of the title compound.

¹H-NMR (DMSO-d6): δ=3.85 (3H), 6.83 (1H), 8.22 (1H), 8.51 (1H), 9.12 (1H), 9.37 (1H), 11.85 (1H) ppm.

Example 18a

6-Amino-5-methoxy-1,3-benzothiazol-2(3H)-one

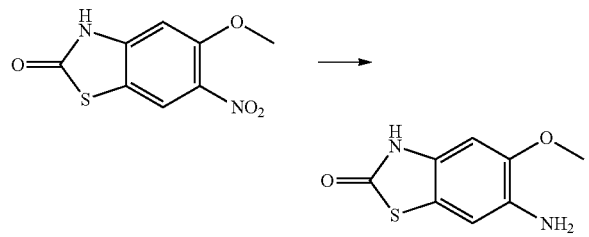

4.14 g (18.3 mmol) 5-methoxy-6-nitro-1,3-benzothiazol-2(3H)-one (prepared according to intermediate example 18b) were transformed in analogy to intermediate example 17d to give after working up and purification 2.15 g (57%) of the title compound.

Example 18b

5-Methoxy-6-nitro-1,3-benzothiazol-2(3H)-one

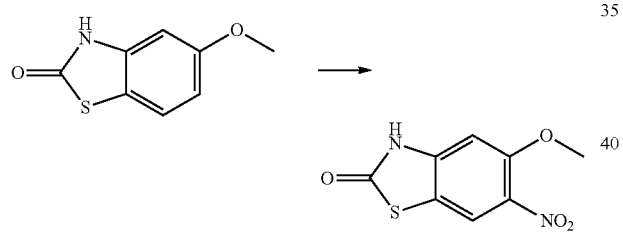

A solution of 6.00 g (33.1 mmol) 5-methoxy-1,3-benzothiazol-2(3H)-one (CAS-No 15193-51-8) in 80 mL sulfuric acid was cooled to −12° C. A mixture comprising 5.01 mL nitric acid (40%) and 4.80 mL sulfuric acid was added slowly. After 30 minutes the mixture was poured into ice-water. The precipitate was filtered, washed with water and hexane and dried to give 6.30 g (84%) of the title compound.

Example 19

6-([1,3]Thiazolo[5,4-d]pyrimidin-7-ylamino)-1,3-benzothiazol-2(3H)-one

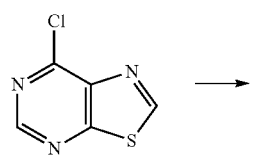

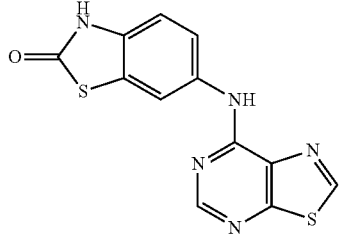

50 mg (291 µmol) 7-chloro[1,3]thiazolo[5,4-d]pyrimidine (CAS-No. 13316-12-6) were transformed in analogy to example 1 using 6-amino-1,3-benzothiazol-2(3H)-one to give after working up and purification 58.1 mg (61%) of the title compound.

¹H-NMR (DMSO-d6): δ=7.11 (1H), 7.71 (1H), 8.12 (1H), 8.53 (1H), 9.39 (1H), 10.25 (1H), 11.85 (1H) ppm.

Example 20

2-[(Benzyloxy)methyl]-N-(6-methoxy-1H-indazol-5-yl)[1,3]thiazolo[5,4-d]pyrimidin-7-amine 324 mg (1.11 mmol) 2-[(benzyloxy)methyl]-7-chloro[1,3]thiazolo[5,4-d]pyrimidine (prepared according to intermediate example 20a) were transformed in analogy to example 1 using 6-methoxy-1H-indazol-5-amine (CAS-No 749223-61-8) to give after working up and purification 9.2 mg (2%) of the title compound.

¹H-NMR (DMSO-d6): δ=3.93 (3H), 4.73 (2H), 4.99 (2H), 7.10 (1H), 7.31-7.46 (5H), 8.00 (1H), 8.44-8.56 (2H), 8.97 (1H), 12.87 (1H) ppm.

Example 20a

2-[(Benzyloxy)methyl]-7-chloro[1,3]thiazolo[5,4-d]pyrimidine

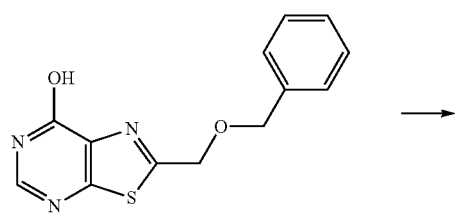

1.11 g (4.06 mmol) 2-[(benzyloxy)methyl][1,3]thiazolo[5,4-d]pyrimidin-7-ol (prepared according to intermediate example 20b) were transformed in analogy to intermediate example 1a to give after working up and purification 330 mg (28%) of the title compound.

Example 20b

2-[(Benzyloxy)methyl][1,3]thiazolo[5,4-d]pyrimidin-7-ol

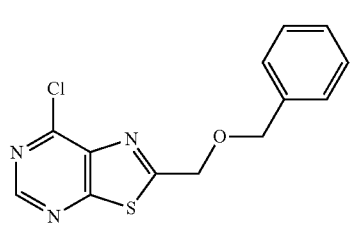

3.21 g (10.28 mmol) 2-(benzyloxy)-N-(4,6-dichloropyrimidin-5-yl)acetamide (prepared according to intermediate example 20c) were transformed in analogy to intermediate example 1b to give after working up and purification 1.12 g (40%) of the title compound.

Example 20c 2-(Benzyloxy)-N-(4,6-dichloropyrimidin-5-yl)acetamide

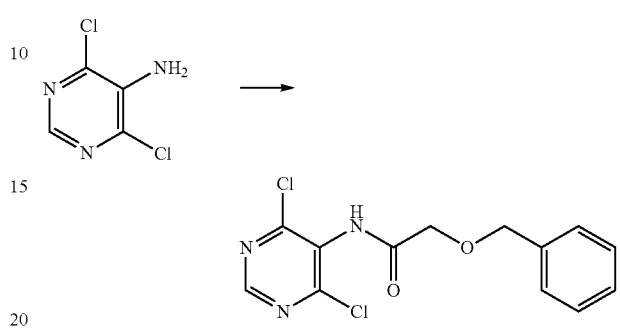

2.00 g (12.2 mmol) 4,6-dichloropyrimidin-5-amine (CAS-No. 5413-85-4) were transformed in analogy to intermediate example 1c using (benzyloxy)acetyl chloride to give after working up and purification 3.42 g (90%) of the title compound.

Example 21

3-[7-(1H-Indazol-5-ylamino)[1,3]thiazolo[5,4-d]pyrimidin-2-yl]-N,N-dimethylpropanamide

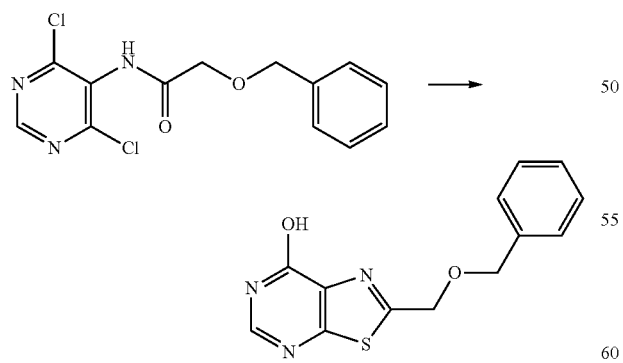

40 mg (118 µmol) 3-[7-(1H-indazol-5-ylamino)[1,3]thiazolo[5,4-d]pyrimidin-2-yl]propanoic acid (prepared according to intermediate example 14a) were transformed in analogy to example 12 using N-methylmethanamine to give after working up and purification 31.0 mg (68%) of the title compound.

$^1$H-NMR (DMSO-d6): δ=2.84 (3H), 2.93 (2H), 2.99 (3H), 3.36 (2H), 7.51 (1H), 7.71 (1H), 8.06 (1H), 8.24 (1H), 8.44 (1H), 9.94 (1H), 13.02 (1H) ppm.

Example 22

N-(6-Methoxy-1H-indazol-5-yl)-2-(2-phenylethyl)[1,3]thiazolo[5,4-d]pyrimidin-7-amine

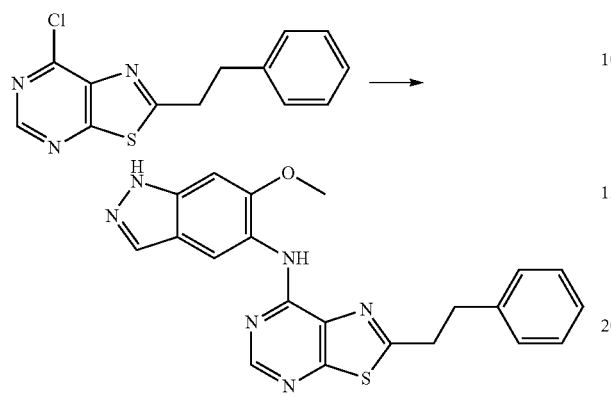

40 mg (145 μmol) 7-chloro-2-(2-phenylethyl)[1,3]thiazolo[5,4-d]pyrimidine (prepared according to intermediate example 17a) were transformed in analogy to example 1 using 6-methoxy-1H-indazol-5-amine (CAS-No 749223-61-8) to give after working up and purification 35.3 mg (57%) of the title compound.

$^1$H-NMR (DMSO-d6): δ=3.16 (2H), 3.48 (2H), 3.94 (3H), 7.10 (1H), 7.21 (1H), 7.27-7.34 (4H), 7.99 (1H), 8.50 (1H), 8.54 (1H), 8.90 (1H), 12.87 (1H) ppm.

Example 23

N-(1H-indazol-5-yl)-2-(2-phenylethyl)[1,3]thiazolo[5,4-d]pyrimidin-7-amine

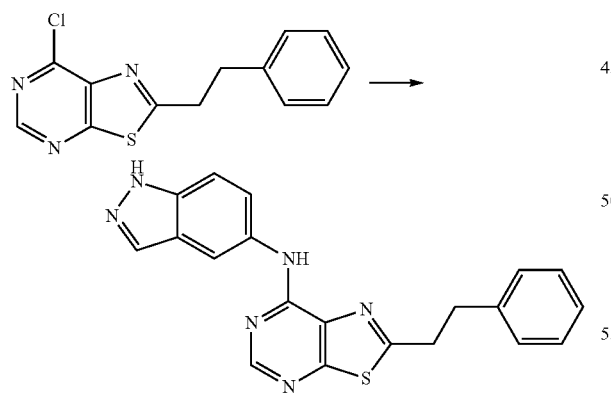

40 mg (145 μmol) 7-chloro-2-(2-phenylethyl)[1,3]thiazolo[5,4-d]pyrimidine (prepared according to intermediate example 17a) were transformed in analogy to example 1 using 1H-indazol-5-amine to give after working up and purification 35.5 mg (62%) of the title compound.

$^1$H-NMR (DMSO-d6): δ=3.17 (2H), 3.48 (2H), 7.18-7.33 (5H), 7.51 (1H), 7.72 (1H), 8.05 (1H), 8.25 (1H), 8.44 (1H), 9.98 (1H), 12.99 (1H) ppm.

Example 24

6-{[2-(2-Phenylethyl)[1,3]thiazolo[5,4-d]pyrimidin-7-yl]amino}-1,3-benzothiazol-2(3H)-one

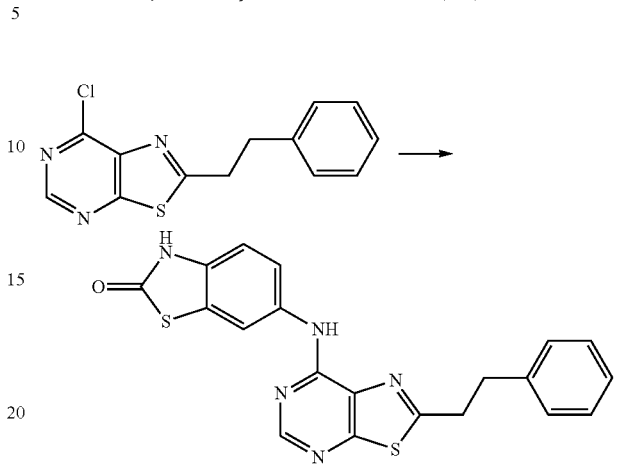

40 mg (145 μmol) 7-chloro-2-(2-phenylethyl)[1,3]thiazolo[5,4-d]pyrimidine (prepared according to intermediate example 17a) were transformed in analogy to example 1 using 6-amino-1,3-benzothiazol-2(3H)-one to give after working up and purification 40.4 mg (69%) of the title compound.

$^1$H-NMR (DMSO-d6): δ=3.16 (2H), 3.47 (2H), 7.10 (1H), 7.21 (1H), 7.27-7.32 (4H), 7.68 (1H), 8.08 (1H), 8.45 (1H), 10.02 (1H), 11.82 (1H) ppm.

Example 25

5-Methoxy-6-{[2-(2-phenylethyl)[1,3]thiazolo[5,4-d]pyrimidin-7-yl]amino}-1,3-benzothiazol-2(3H)-one

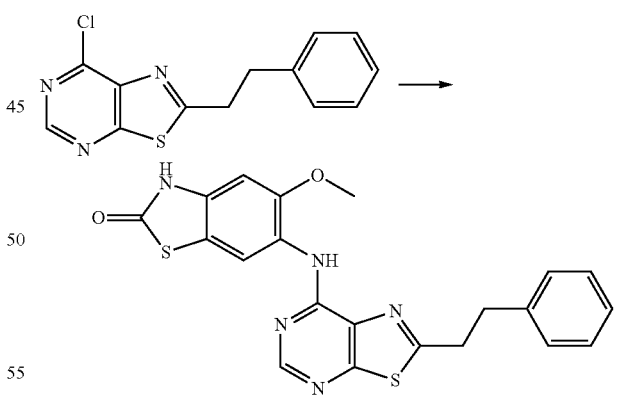

40 mg (145 μmol) 7-chloro-2-(2-phenylethyl)[1,3]thiazolo[5,4-d]pyrimidine (prepared according to intermediate example 17a) were transformed in analogy to example 1 using 6-amino-5-methoxy-1,3-benzothiazol-2(3H)-one (prepared according to intermediate example 18a) to give after working up and purification 47.2 mg (71%) of the title compound.

$^1$H-NMR (DMSO-d6): δ=3.15 (2H), 3.47 (2H), 3.85 (3H), 6.83 (1H), 7.18-7.33 (5H), 8.20 (1H), 8.44 (1H), 8.91 (1H), 11.81 (1H) ppm.

Example 26

4-{7-[(6-Methoxy-1H-indazol-5-yl)amino][1,3]thi-
azolo[5,4-d]pyrimidin-2-yl}-N, N-dimethylbutana-
mide

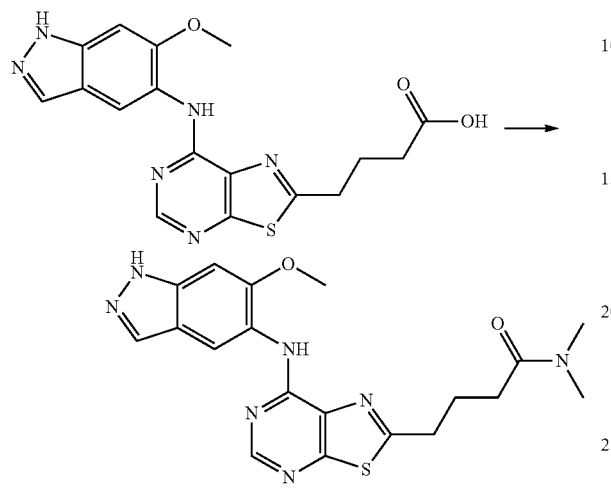

25.7 mg (67 µmol) 4-{7-[(6-methoxy-1H-indazol-5-yl) amino][1,3]thiazolo[5,4-d]pyrimidin-2-yl}butanoic acid (prepared according to intermediate example 26a) were transformed in analogy to example 12 using N-methylmethanamine to give after working up and purification 8.1 mg (28%) of the title compound.

$^1$H-NMR (DMSO-d6): δ=2.03 (2H), 2.46 (2H), 2.82 (3H), 2.95 (3H), 3.17 (2H), 3.94 (3H), 7.10 (1H), 8.00 (1H), 8.51 (1H), 8.56 (1H), 8.89 (1H), 12.90 (1H) ppm.

Example 26a

4-{7-[(6-Methoxy-1H-indazol-5-yl)amino][1,3]thi-
azolo[5,4-d]pyrimidin-2-yl}butanoic acid

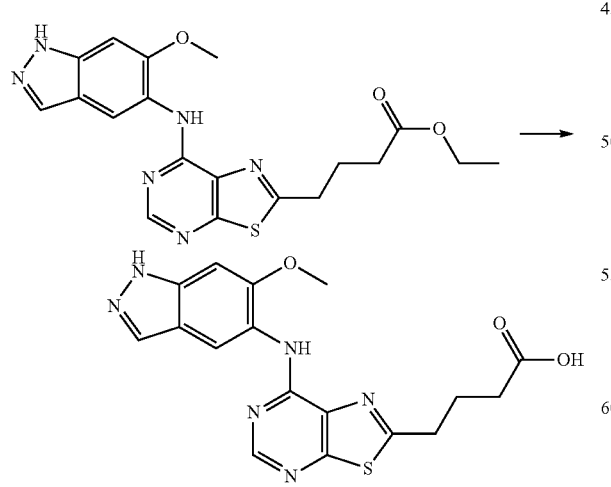

30 mg (73 µmol) ethyl 4-{7-[(6-methoxy-1H-indazol-5-yl)amino][1,3]thiazolo[5,4-d]pyrimidin-2-yl}butanoate (prepared according to intermediate example 26b) were transformed in analogy to intermediate example 12a to give after working up and purification 26.8 mg (96%) of the title compound.

Example 26b

Ethyl 4-{7-[(6-methoxy-1H-indazol-5-yl)amino][1,3]thiazolo[5,4-d]pyrimidin-2-yl}butanoate

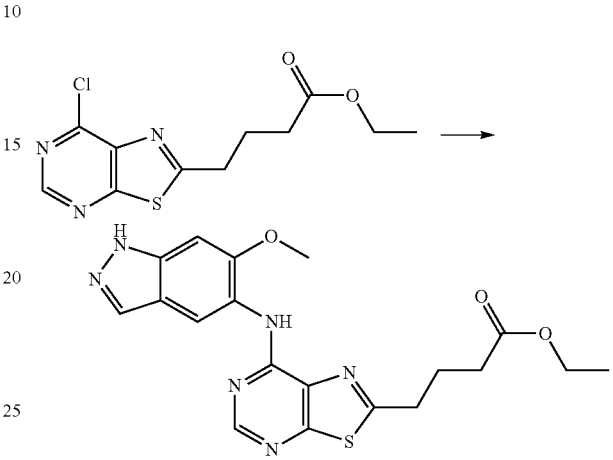

50 mg (175 µmol) ethyl 4-(7-chloro[1,3]thiazolo[5,4-d]pyrimidin-2-yl)butanoate (prepared according to intermediate example 12c) were transformed in analogy to example 1 using 6-methoxy-1H-indazol-5-amine (CAS-No 749223-61-8) to give after working up and purification 30.1 mg (42%) of the title compound.

Example 27

N,N-Dimethyl-7-[(2-oxo-2,3-dihydro-1,3-benzothi-
azol-6-yl)amino][1,3]thiazolo[5,4-d]pyrimidine-2-
carboxamide

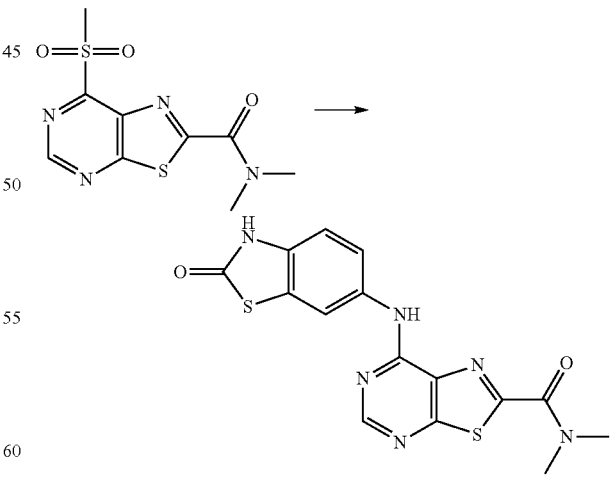

100 mg (349 µmol) N,N-dimethyl-7-(methylsulfonyl)[1,3]thiazolo[5,4-d]pyrimidine-2-carboxamide (prepared according to intermediate example 27a) were transformed in analogy to example 1 to give after working up and purification 122 mg (89%) of the title compound.

¹H-NMR (DMSO-d6): δ=3.09 (3H), 3.57 (3H), 7.14 (1H), 7.60 (1H), 8.01 (1H), 8.54 (1H), 10.08 (1H), 11.88 (1H) ppm.

Example 27a

N,N-Dimethyl-7-(methylsulfanyl)[1,3]thiazolo[5,4-d]pyrimidine-2-carboxamide

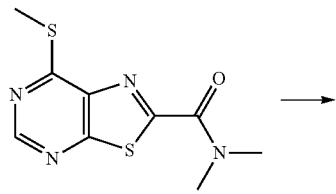

A mixture comprising 635 mg (2.50 mmol) N,N-dimethyl-7-(methylsulfanyl)[1,3]thiazolo[5,4-d]pyrimidine-2-carboxamide (prepared according to intermediate example 27b), 30 mL dichloromethane and 1.44 g 3-chlorobenzenecarboperoxoic acid (75%) was stirred at 20° C. for 2 hours. 15 mL dimethyl sulfoxide were added, the dichloromethane removed to give the title compound as 0.156 M solution in dimethyl sulfoxide Example 27b N,N-Dimethyl-7-(methylsulfanyl)[1,3]thiazolo[5,4-d]pyrimidine-2-carboxamide

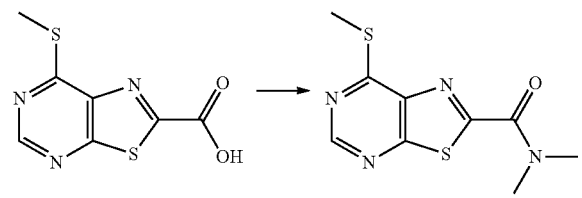 [SMILES: CSc1ncnc2sc(C(=O)O)nc12 ; CSc1ncnc2sc(C(=O)N(C)C)nc12]

1.00 g (4.40 mmol) 7-(methylsulfanyl)[1,3]thiazolo[5,4-d]pyrimidine-2-carboxylic acid (prepared according to WO2005/117890) were transformed in analogy to example 12 using N-methylmethanamine to give after working up and purification 907 mg (81%) of the title compound.

Example 28

7-[(5-Methoxy-2-oxo-2,3-dihydro-1,3-benzothiazol-6-yl)amino]-N,N-dimethyl[1,3]thiazolo[5,4-d]pyrimidine-2-carboxamide

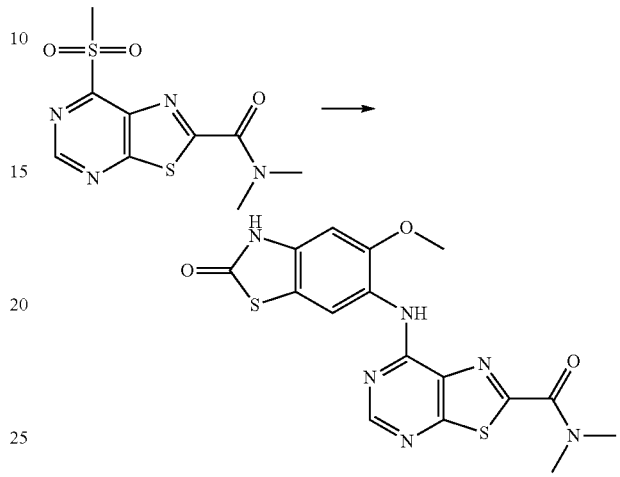

80 mg (279 μmol) N,N-Dimethyl-7-(methylsulfonyl)[1,3]thiazolo[5,4-d]pyrimidine-2-carboxamide (prepared according to intermediate example 27a) were transformed in analogy to example 1 using 6-amino-5-methoxy-1,3-benzothiazol-2(3H)-one (prepared according to intermediate example 18a) to give after working up and purification 85.1 mg (72%) of the title compound.

¹H-NMR (DMSO-d6): δ=3.08 (3H), 3.51 (3H), 3.79 (3H), 6.82 (1H), 7.90 (1H), 8.47 (1H), 9.44 (1H), 11.88 (1H) ppm.

Example 29

7-[(6-Methoxy-1H-indazol-5-yl)amino]-N,N-dimethyl[1,3]thiazolo[5,4-d]pyrimidine-2-carboxamide

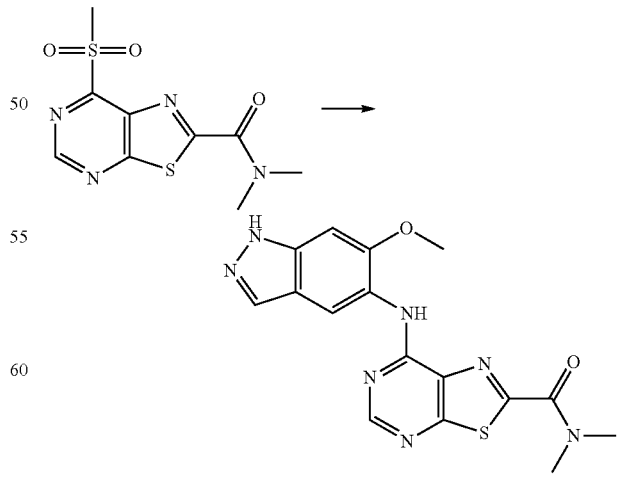

112.5 mg (393 μmol) N,N-Dimethyl-7-(methylsulfonyl)[1,3]thiazolo[5,4-d]pyrimidine-2-carboxamide (prepared according to intermediate example 27a) were transformed in analogy to example 1 using 6-methoxy-1H-indazol-5-amine (CAS-No 749223-61-8) to give after working up and purification 50.3 mg (33%) of the title compound.

$^1$H-NMR (DMSO-d6): δ=3.08 (3H), 3.49 (3H), 3.87 (3H), 7.09 (1H), 7.99 (1H), 8.24 (1H), 8.52 (1H), 9.38 (1H), 12.90 (1H) ppm.

Example 30

7-[(6-Ethoxy-1H-indazol-5-yl)amino]-N,N-dimethyl[1,3]thiazolo[5,4-d]pyrimidine-2-carboxamide

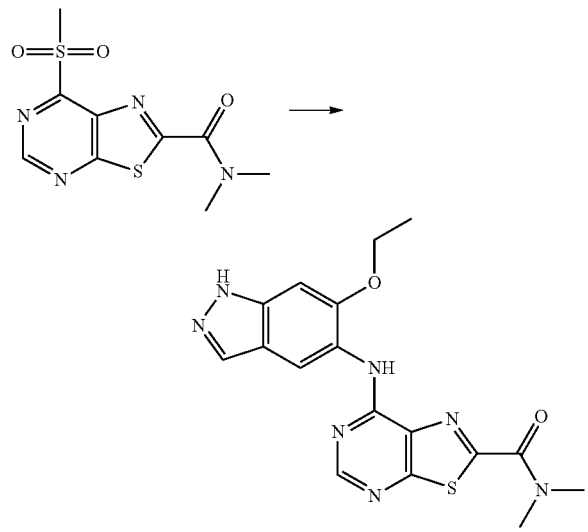

100 mg (349 μmol) N,N-Dimethyl-7-(methylsulfonyl)[1,3]thiazolo[5,4-d]pyrimidine-2-carboxamide (prepared according to intermediate example 27a) were transformed in analogy to example 1 using 6-ethoxy-1H-indazol-5-amine (prepared according to intermediate example 30a) to give after working up and purification 75.9 mg (54%) of the title compound.

$^1$H-NMR (DMSO-d6): δ=1.34 (3H), 3.09 (3H), 3.56 (3H), 4.16 (2H), 7.08 (1H), 8.01 (1H), 8.63 (2H), 9.21 (1H), 12.87 (1H) ppm.

Example 30a

6-Ethoxy-1H-indazol-5-amine

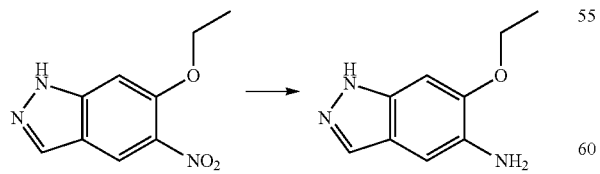

10.0 g (48.3 mmol) 6-ethoxy-5-nitro-1H-indazole (Supplier: Angene Chemicals, Hong Kong PO#2343258 & 2374166) were transformed in analogy to intermediate example 17d to give after working up and purification 5.08 g (59%) of the title compound.

Example 31

[7-(1H-Indazol-5-ylamino)[1,3]thiazolo[5,4-d]pyrimidin-2-yl](piperidin-1-yl)methanone

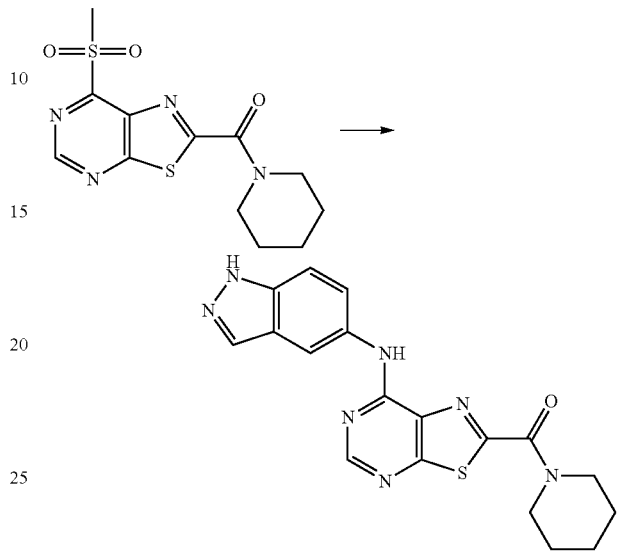

100 mg (306 μmol) [7-(methylsulfonyl)[1,3]thiazolo[5,4-d]pyrimidin-2-yl](piperidin-1-yl)methanone (prepared according to intermediate example 31a) were transformed in analogy to example 1 using 1H-indazol-5-amine to give after working up and purification 17.8 mg (15%) of the title compound.

$^1$H-NMR (DMSO-d6): δ=1.44-1.74 (6H), 3.65 (2H), 4.17 (2H), 7.55 (1H), 7.62 (1H), 8.08 (1H), 8.12 (1H), 8.51 (1H), 10.11 (1H), 13.07 (1H) ppm.

Example 31a

[7-(Methylsulfonyl)[1,3]thiazolo[5,4-d]pyrimidin-2-yl](piperidin-1-yl)methanone

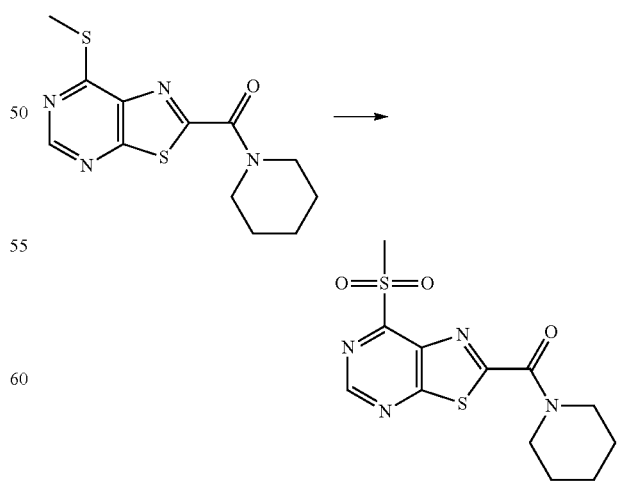

800 mg (272 μmol) [7-(methylsulfanyl)[1,3]thiazolo[5,4-d]pyrimidin-2-yl](piperidin-1-yl)methanone (prepared according to intermediate example 31b) were transformed in analogy to intermediate example 27a to give the title compound as 0.124 M dimethyl sulfoxide solution.

Example 31b

[7-(Methylsulfanyl)[1,3]thiazolo[5,4-d]pyrimidin-2-yl](piperidin-1-yl)methanone

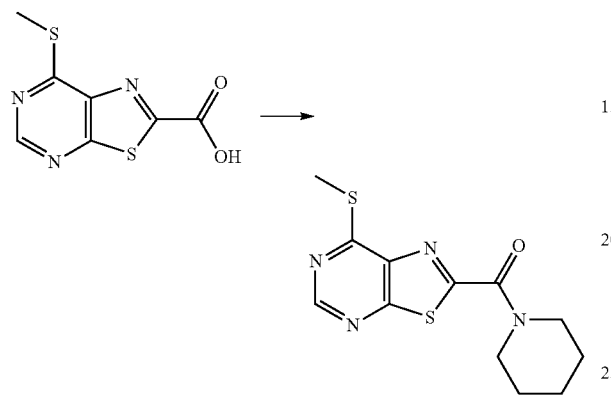

1.00 g (4.40 mmol) 7-(methylsulfanyl)[1,3]thiazolo[5,4-d]pyrimidine-2-carboxylic acid (prepared according to WO2005/117890) were transformed in analogy to example 12 using piperidine to give after working up and purification 998 mg (77%) of the title compound.

Example 32

6-{[2-(Piperidin-1-ylcarbonyl)[1,3]thiazolo[5,4-d]pyrimidin-7-yl]amino}-1,3-benzothiazol-2(3H)-one

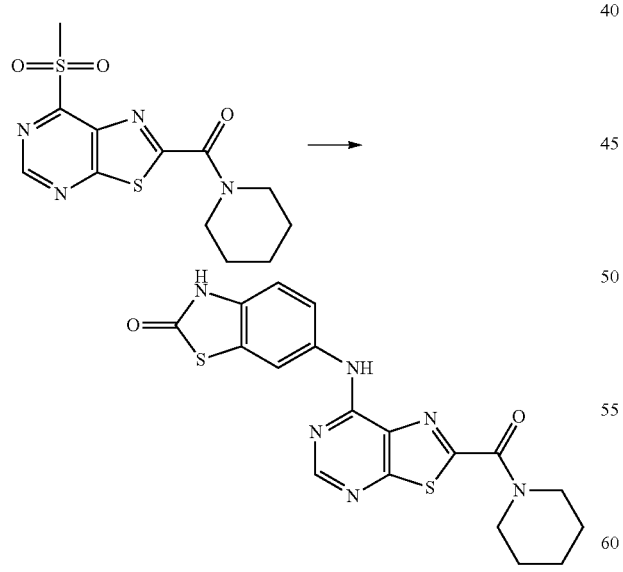

100 mg (306 μmol) [7-(methylsulfonyl)[1,3]thiazolo[5,4-d]pyrimidin-2-yl](piperidin-1-yl)methanone (prepared according to intermediate example 31a) were transformed in analogy to example 1 to give after working up and purification 91.9 mg (69%) of the title compound.

$^1$H-NMR (DMSO-d6): δ=1.49-1.73 (6H), 3.65 (2H), 4.15 (2H), 7.13 (1H), 7.58 (1H), 7.98 (1H), 8.53 (1H), 10.08 (1H), 11.86 (1H) ppm.

Example 33

{7-[(6-Methoxy-1H-indazol-5-yl)amino][1,3]thiazolo[5,4-d]pyrimidin-2-yl}(piperidin-1-yl)methanone

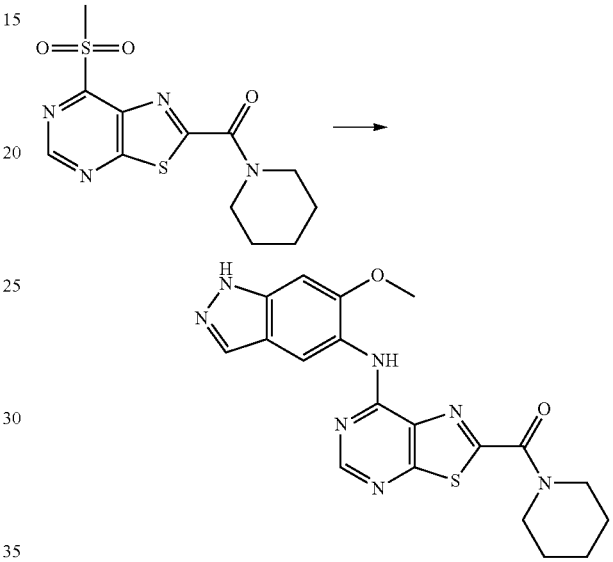

100 mg (306 μmol) [7-(methylsulfonyl)[1,3]thiazolo[5,4-d]pyrimidin-2-yl](piperidin-1-yl)methanone (prepared according to intermediate example 31a) were transformed in analogy to example 1 using 6-methoxy-1H-indazol-5-amine (CAS-No 749223-61-8) to give after working up and purification 68.8 mg (52%) of the title compound.

$^1$H-NMR (DMSO-d6): δ=1.42-1.73 (6H), 3.63 (2H), 3.86 (3H), 3.99-4.27 (2H), 7.08 (1H), 8.00 (1H), 8.26 (1H), 8.53 (1H), 9.39 (1H), 12.92 (1H) ppm.

Example 34

{7-[(6-Ethoxy-1H-indazol-5-yl)amino][1,3]thiazolo[5,4-d]pyrimidin-2-yl}(piperidin-1-yl)methanone

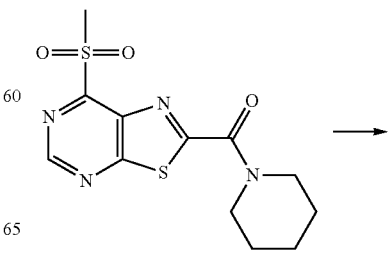

-continued

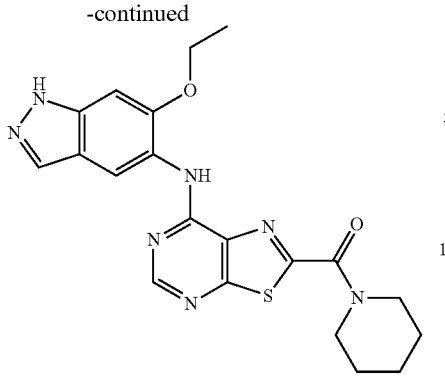

100 mg (306 μmol) [7-(methylsulfonyl)[1,3]thiazolo[5,4-d]pyrimidin-2-yl](piperidin-1-yl)methanone (prepared according to intermediate example 31a) were transformed in analogy to example 1 using 6-ethoxy-1H-indazol-5-amine (prepared according to intermediate example 30a) to give after working up and purification 40.9 mg (30%) of the title compound.

$^1$H-NMR (DMSO-d6): δ=1.32 (3H), 1.48-1.74 (6H), 3.64 (2H), 4.03-4.35 (4H), 7.07 (1H), 8.00 (1H), 8.62 (2H), 9.17 (1H), 12.86 (1H) ppm.

Example 35

Piperidin-1-yl(7-{[6-(propan-2-yloxy)-1H-indazol-5-yl]amino}[1,3]thiazolo[5,4-d]pyrimidin-2-yl)methanone

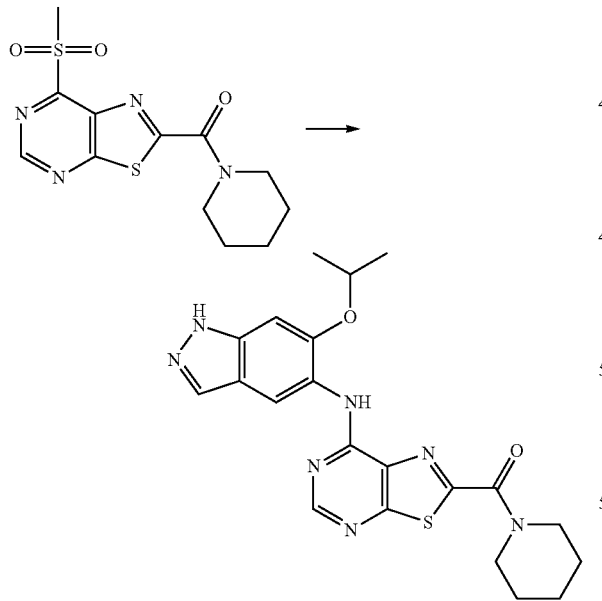

100 mg (306 μmol) [7-(methylsulfonyl)[1,3]thiazolo[5,4-d]pyrimidin-2-yl](piperidin-1-yl)methanone (prepared according to intermediate example 31a) were transformed in analogy to example 1 using 6-isopropoxy-1H-indazol-5-amine (prepared according to intermediate example 17d) to give after working up and purification 67.5 mg (48%) of the title compound.

$^1$H-NMR (DMSO-d6): δ=1.29 (6H), 1.48-1.76 (6H), 3.64 (2H), 4.01-4.38 (2H), 4.76 (1H), 7.12 (1H), 8.01 (1H), 8.64 (1H), 8.71 (1H), 9.12 (1H), 12.83 (1H) ppm.

Example 36

N-[2-(Dimethylamino)-2-oxoethyl]-7-(1H-indazol-5-ylamino)-N-methyl[1,3]thiazolo[5,4-d]pyrimidine-2-carboxamide

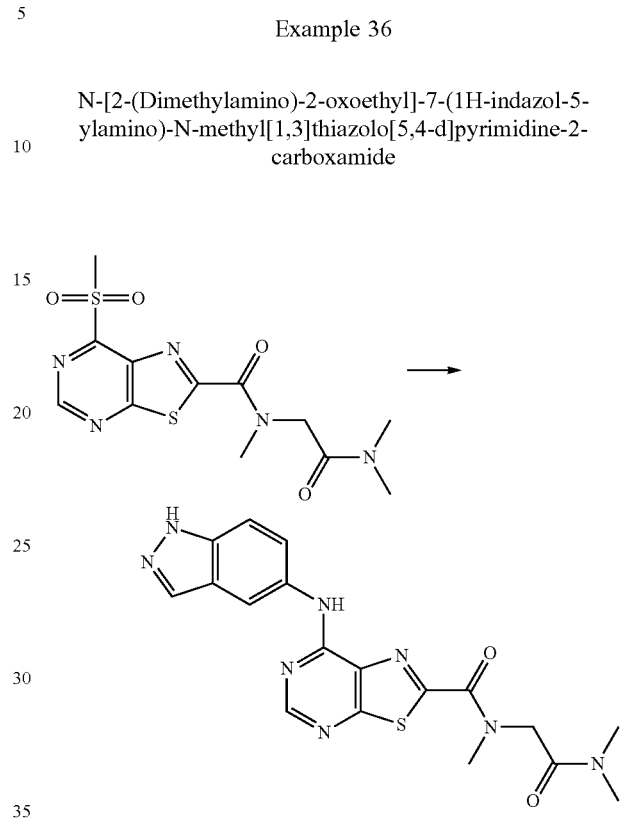

100 mg (280 μmol) N-[2-(dimethylamino)-2-oxoethyl]-N-methyl-7-(methylsulfonyl)[1,3]thiazolo[5,4-d]pyrimidine-2-carboxamide (prepared according to intermediate example 36a) were transformed in analogy to example 1 using 1H-indazol-5-amine to give after working up and purification 53.1 mg (44%) of the title compound.

$^1$H-NMR (DMSO-d6): δ=2.74+2.86 (3H), 3.00+3.02 (3H), 3.04+3.57 (3H), 4.40+5.23 (2H), 7.56 (1H), 7.66 (1H), 8.09 (1H), 8.16+8.23 (1H), 8.54 (1H), 9.98+10.15 (1H), 13.09 (1H) ppm.

Example 36a

N-[2-(Dimethylamino)-2-oxoethyl]-N-methyl-7-(methylsulfonyl)[1,3]thiazolo[5,4-d]pyrimidine-2-carboxamide

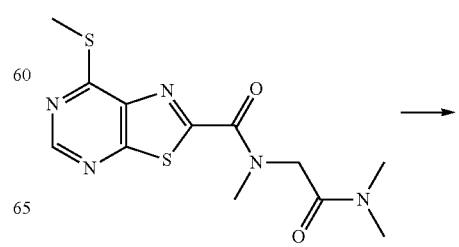

-continued

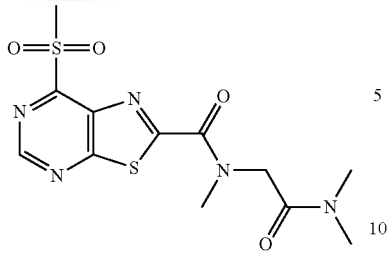

800 mg (2.46 mmol) N-[2-(dimethylamino)-2-oxoethyl]-N-methyl-7-(methylsulfanyl)[1,3]thiazolo[5,4-d]pyrimidine-2-carboxamide (prepared according to intermediate example 36b) were transformed in analogy to intermediate example 27a to give the title compound as 0.102 M dimethyl sulfoxide solution.

Example 36b

N-[2-(Dimethylamino)-2-oxoethyl]-N-methyl-7-(methylsulfanyl)[1,3]thiazolo[5,4-d]pyrimidine-2-carboxamide

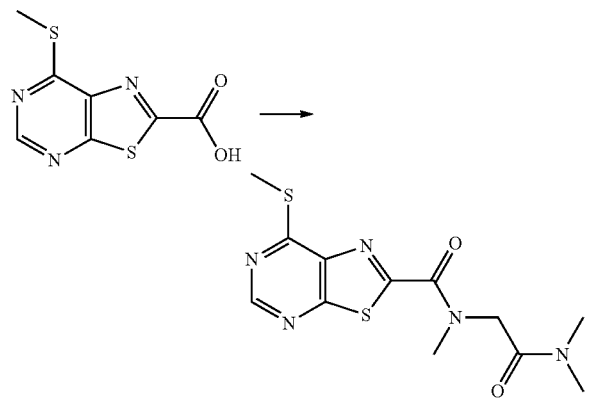

1.00 g (4.40 mmol) 7-(methylsulfanyl)[1,3]thiazolo[5,4-d]pyrimidine-2-carboxylic acid (prepared according to WO2005/117890) were transformed in analogy to example 12 using N,N,N²-trimethylglycinamide to give after working up and purification 1.03 g (72%) of the title compound.

Example 37

N-[2-(Dimethylamino)-2-oxoethyl]-N-methyl-7-[(2-oxo-2,3-dihydro-1,3-benzothiazol-6-yl)amino][1,3]thiazolo[5,4-d]pyrimidine-2-carboxamide

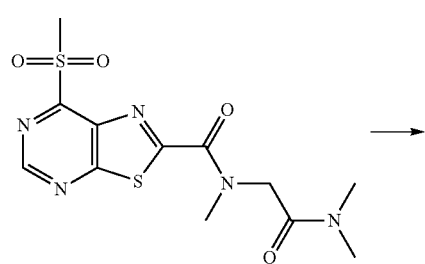

-continued

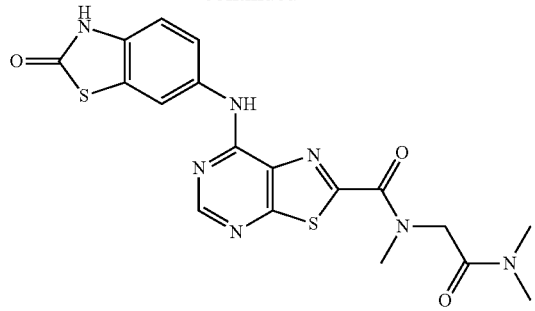

100 mg (280 µmol) N-[2-(dimethylamino)-2-oxoethyl]-N-methyl-7-(methylsulfonyl)[1,3]thiazolo[5,4-d]pyrimidine-2-carboxamide (prepared according to intermediate example 36a) were transformed in analogy to example 1 to give after working up and purification 114.2 mg (92%) of the title compound.
$^1$H-NMR (DMSO-d6): δ=2.73+2.86 (3H), 3.00 (3H), 3.04+3.57 (3H), 4.40+5.21 (2H), 7.13+7.15 (1H), 7.60+7.62 (1H), 8.02+8.07 (1H), 8.55 (1H), 9.98+10.12 (1H), 11.87 (1H) ppm.

Example 38

N-[2-(Dimethylamino)-2-oxoethyl]-7-[(6-methoxy-1H-indazol-5-yl)amino]-N-methyl[1,3]thiazolo[5,4-d]pyrimidine-2-carboxamide

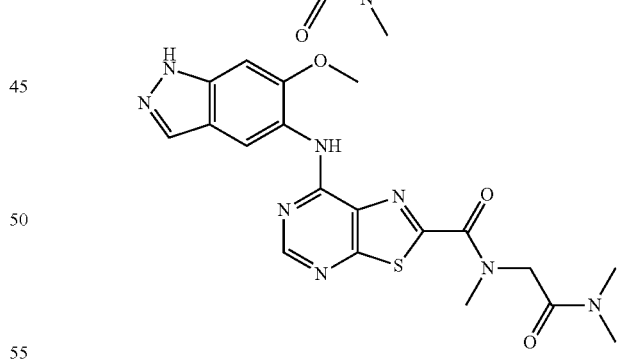

100 mg (280 µmol) N-[2-(dimethylamino)-2-oxoethyl]-N-methyl-7-(methylsulfonyl)[1,3]thiazolo[5,4-d]pyrimidine-2-carboxamide (prepared according to intermediate example 36a) were transformed in analogy to example 1 using 6-methoxy-1H-indazol-5-amine (CAS-No 749223-61-8) to give after working up and purification 20.1 mg (15%) of the title compound.
$^1$H-NMR (DMSO-d6): δ=2.78+2.85 (3H), 2.99+3.01 (3H), 3.04+3.50 (3H), 3.87+3.89 (3H), 4.38+5.13 (2H), 7.09+7.11 (1H), 8.00 (1H), 8.20+8.30 (1H), 8.52 (1H), 9.11+9.48 (1H), 12.92 (1H) ppm.

Example 39

N-[2-(Dimethylamino)-2-oxoethyl]-N-methyl-7-{[6-(propan-2-yloxy)-1H-indazol-5-yl]amino}[1,3]thiazolo[5,4-d]pyrimidine-2-carboxamide

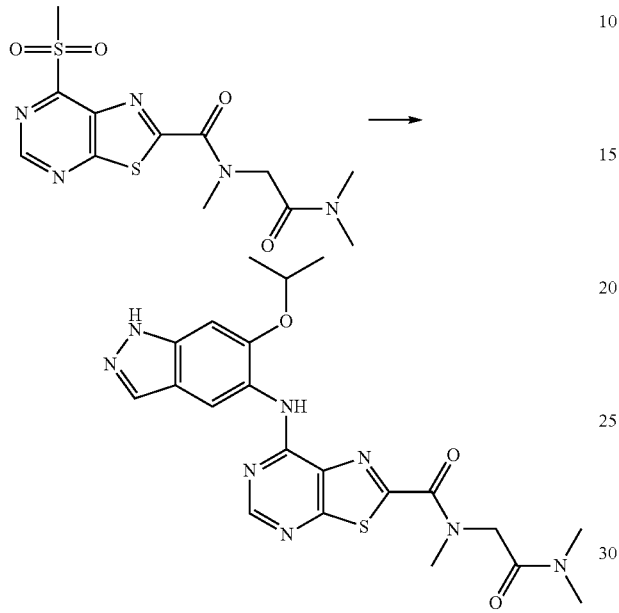

100 mg (280 µmol) N-[2-(dimethylamino)-2-oxoethyl]-N-methyl-7-(methylsulfonyl)[1,3]thiazolo[5,4-d]pyrimidine-2-carboxamide (prepared according to intermediate example 36a) were transformed in analogy to example 1 using 6-isopropoxy-1H-indazol-5-amine (prepared according to intermediate example 17d) to give after working up and purification 12.7 mg (9%) of the title compound.

$^1$H-NMR (DMSO-d6): δ=1.25+1.30 (6H), 2.76+2.86 (3H), 2.95+2.99 (3H), 3.02+3.59 (3H), 4.41+5.10 (2H), 4.70+4.78 (1H), 7.11+7.13 (1H), 8.00+8.02 (1H), 8.35+8.54 (1H), 8.57+8.73 (1H), 9.15+9.22 (1H), 12.85 (1H) ppm.

Example 40

N-[3-(Dimethylamino)-3-oxopropyl]-7-(1H-indazol-5-ylamino)-N-methyl[1,3]thiazolo[5,4-d]pyrimidine-2-carboxamide

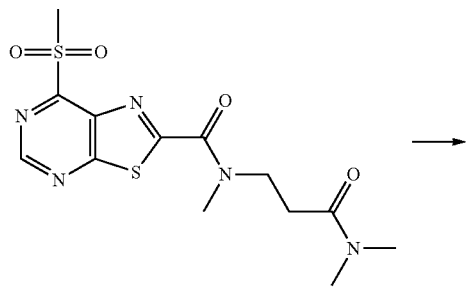

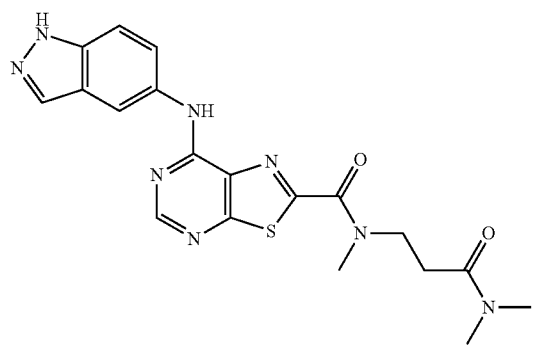

95 mg (256 µmol) N-[3-(dimethylamino)-3-oxopropyl]-N-methyl-7-(methylsulfonyl)[1,3]thiazolo[5,4-d]pyrimidine-2-carboxamide (prepared according to intermediate example 40a) were transformed in analogy to example 1 using 1H-indazol-5-amine to give after working up and purification 50.2 mg (44%) of the title compound.

$^1$H-NMR (DMSO-d6): δ=2.69+2.88 (2H), 2.80+2.83 (3H), 2.98+3.01 (3H), 3.12+3.60 (3H), 3.69+4.28 (2H), 7.54+7.57 (1H), 7.64+7.87 (1H), 8.09 (1H), 8.15+8.43 (1H), 8.52+8.60 (1H), 10.10 (1H), 13.07 (1H) ppm.

Example 40a

N-[3-(Dimethylamino)-3-oxopropyl]-N-methyl-7-(methylsulfonyl)[1,3]thiazolo[5,4-d]pyrimidine-2-carboxamide

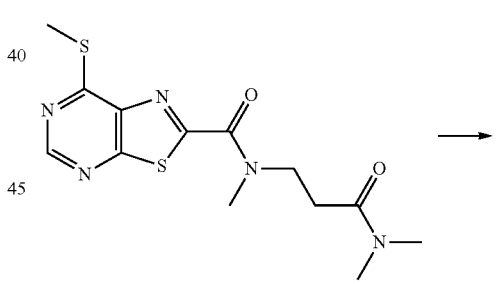

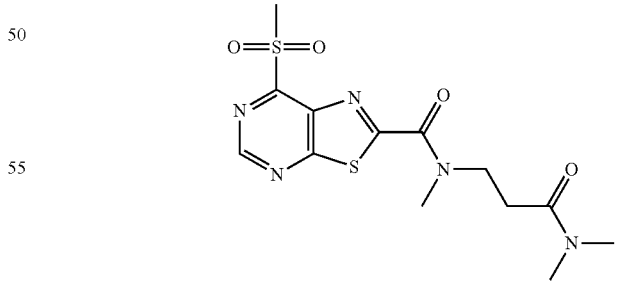

700 mg (2.06 µmol) N-[3-(dimethylamino)-3-oxopropyl]-N-methyl-7-(methylsulfanyl)[1,3]thiazolo[5,4-d]pyrimidine-2-carboxamide (prepared according to intermediate example 40a) were transformed in analogy to intermediate example 27a to give the title compound as 0.103 M dimethyl sulfoxide solution.

Example 40b

N-[3-(Dimethylamino)-3-oxopropyl]-N-methyl-7-(methylsulfanyl)[1,3]thiazolo[5,4-d]pyrimidine-2-carboxamide

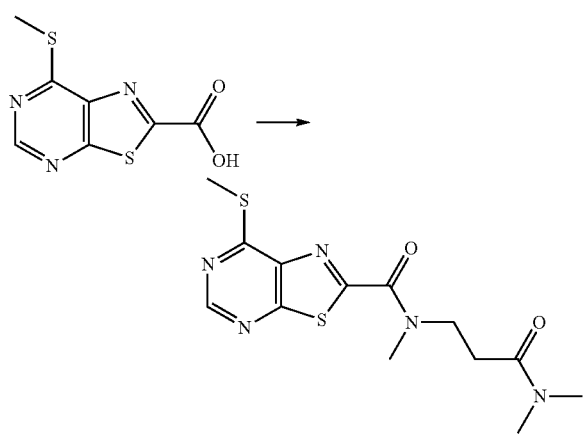

1.00 g (4.40 mmol) 7-(methylsulfanyl)[1,3]thiazolo[5,4-d]pyrimidine-2-carboxylic acid (prepared according to WO2005/117890) were transformed in analogy to example 12 using N,N,N³-trimethyl-beta-alaninamide to give after working up and purification 759 mg (51%) of the title compound.

Example 41

N-[3-(Dimethylamino)-3-oxopropyl]-N-methyl-7-[(2-oxo-2,3-dihydro-1,3-benzothiazol-6-yl)amino][1,3]thiazolo[5,4-d]pyrimidine-2-carboxamide

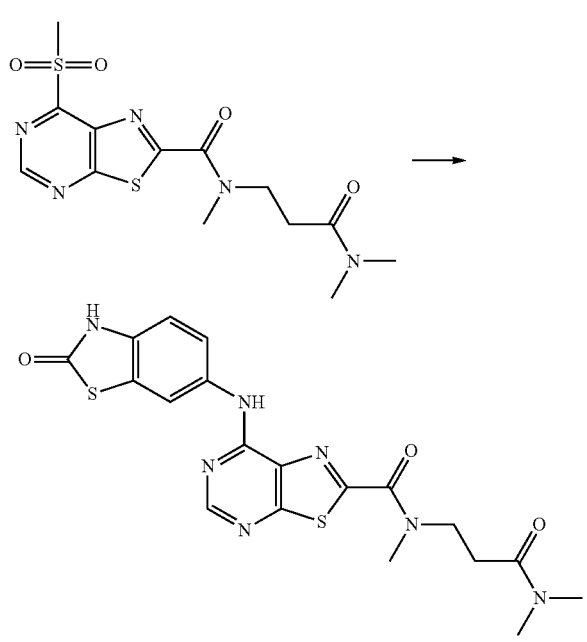

95 mg (256 μmol) N-[3-(dimethylamino)-3-oxopropyl]-N-methyl-7-(methylsulfonyl)[1,3]thiazolo[5,4-d]pyrimidine-2-carboxamide (prepared according to intermediate example 40a) were transformed in analogy to example 1 to give after working up and purification 67.7 mg (55%) of the title compound.

$^1$H-NMR (DMSO-d6): δ=2.72+2.89 (2H), 2.82+2.85 (3H), 3.00+3.03 (3H), 3.14+3.61 (3H), 3.71+4.27 (2H), 7.16 (1H), 7.62+7.85 (1H), 8.03+8.28 (1H), 8.56+8.62 (1H), 10.10+10.14 (1H), 11.92 (1H) ppm.

Example 42

N-[3-(Dimethylamino)-3-oxopropyl]-7-[(6-ethoxy-1H-indazol-5-yl)amino]-N-methyl[1,3]thiazolo[5,4-d]pyrimidine-2-carboxamide

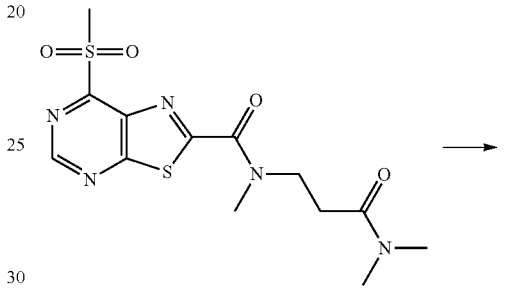

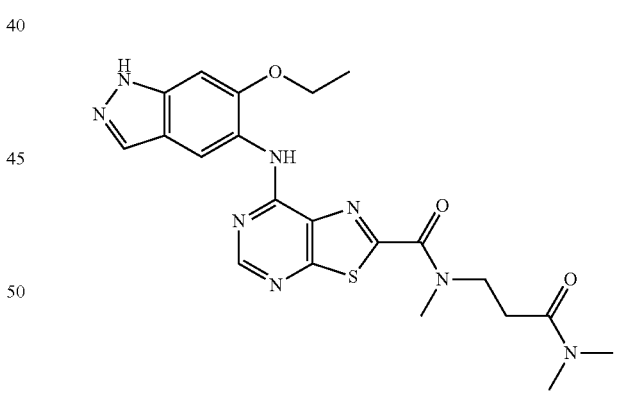

95 mg (256 μmol) N-[3-(dimethylamino)-3-oxopropyl]-N-methyl-7-(methylsulfonyl)[1,3]thiazolo[5,4-d]pyrimidine-2-carboxamide (prepared according to intermediate example 40a) were transformed in analogy to example 1 using 6-ethoxy-1H-indazol-5-amine (prepared according to intermediate example 30a) to give after working up and purification 40.7 mg (32%) of the title compound.

$^1$H-NMR (DMSO-d6): δ=1.33+1.36 (3H), 2.66-2.79 (2H), 2.71+2.85 (3H), 2.94+3.00 (3H), 3.10+3.62 (3H), 3.71+4.33 (2H), 4.19 (2H), 7.11 (1H), 8.03 (1H), 8.46+8.63 (1H), 8.61+8.66 (1H), 9.23+9.25 (1H), 12.90 (1H) ppm.

Example 43

7-(1H-Indazol-5-ylamino)-N,N-dimethyl[1,3]thi-
azolo[5,4-d]pyrimidine-2-carboxamide

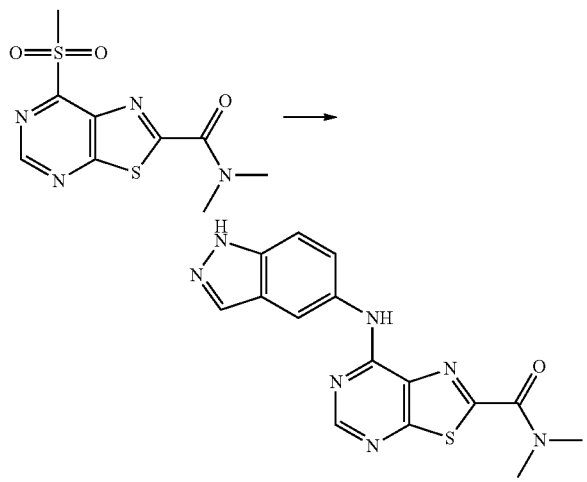

100 mg (349 µmol) N,N-Dimethyl-7-(methylsulfonyl)[1,3]thiazolo[5,4-d]pyrimidine-2-carboxamide (prepared according to intermediate example 27a) were transformed in analogy to example 1 using 1H-indazol-5-amine to give after working up and purification 33.8 mg (29%) of the title compound.

$^1$H-NMR (DMSO-d6): δ=3.09 (3H), 3.57 (3H), 7.55 (1H), 7.64 (1H), 8.08 (1H), 8.15 (1H), 8.52 (1H), 10.09 (1H), 13.07 (1H) ppm.

Example 44

N,N-Dimethyl-7-{[6-(propan-2-yloxy)-1H-indazol-5-yl]amino}[1,3]thiazolo[5,4-d]pyrimidine-2-carboxamide

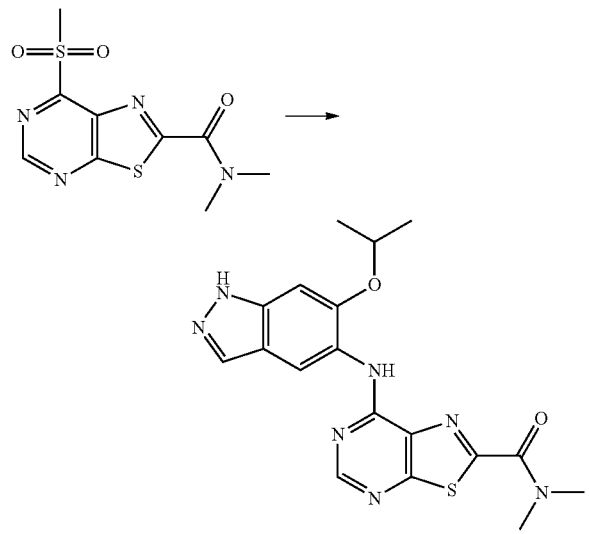

100 mg (349 µmol) N,N-Dimethyl-7-(methylsulfonyl)[1,3]thiazolo[5,4-d]pyrimidine-2-carboxamide (prepared according to intermediate example 27a) were transformed in analogy to example 1 using 6-isopropoxy-1H-indazol-5-amine (prepared according to intermediate example 17d) to give after working up and purification 17.8 mg (12%) of the title compound.

$^1$H-NMR (DMSO-d6): δ=1.31 (6H), 3.09 (3H), 3.58 (3H), 4.78 (1H), 7.12 (1H), 8.01 (1H), 8.65 (1H), 8.71 (1H), 9.14 (1H), 12.82 (1H) ppm.

Example 45

N-[2-(Dimethylamino)-2-oxoethyl]-7-[(6-ethoxy-1H-indazol-5-yl)amino]-N-methyl[1,3]thiazolo[5,4-d]pyrimidine-2-carboxamide

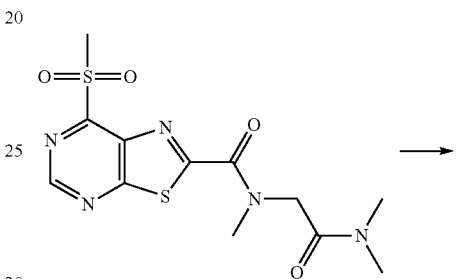

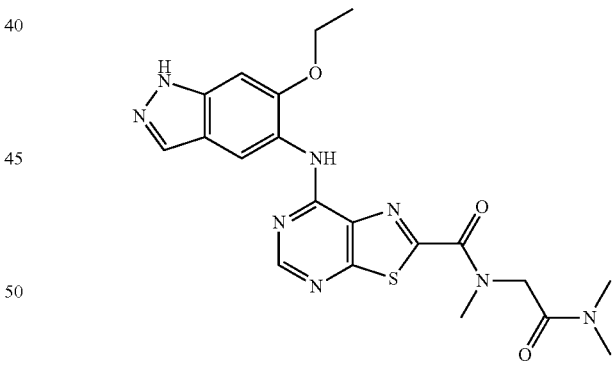

100 mg (280 µmol) N-[2-(dimethylamino)-2-oxoethyl]-N-methyl-7-(methylsulfonyl)[1,3]thiazolo[5,4-d]pyrimidine-2-carboxamide (prepared according to intermediate example 36a) were transformed in analogy to example 1 using 6-ethoxy-1H-indazol-5-amine (prepared according to intermediate example 30a) to give after working up and purification 10.3 mg (8%) of the title compound.

$^1$H-NMR (DMSO-d6): δ=1.29+1.34 (3H), 2.77+2.87 (3H), 2.97+3.01 (3H), 3.04+3.60 (3H), 3.57 (1H), 4.12-4.23 (2H), 4.42+5.11 (1H), 7.10 (1H), 8.01+8.03 (1H), 8.29+8.62 (1H), 8.54+8.66 (1H), 9.21+9.30 (1H), 12.90 (1H) ppm.

Example 46

N-[3-(Dimethylamino)-3-oxopropyl]-7-[(6-methoxy-1H-indazol-5-yl)amino]-N-methyl[1,3]thiazolo[5,4-d]pyrimidine-2-carboxamide

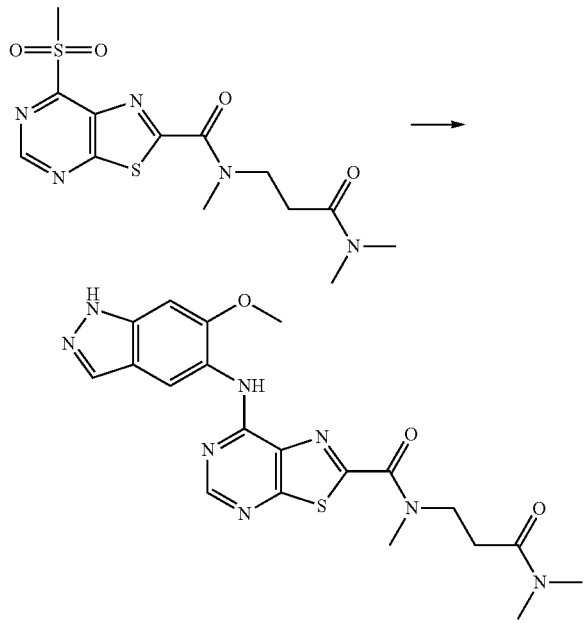

95 mg (256 μmol) N-[3-(dimethylamino)-3-oxopropyl]-N-methyl-7-(methylsulfonyl)[1,3]thiazolo[5,4-d]pyrimidine-2-carboxamide (prepared according to intermediate example 40a) were transformed in analogy to example 1 using 6-methoxy-1H-indazol-5-amine (CAS-No 749223-61-8) to give after working up and purification 30.2 mg (25%) of the title compound.

$^1$H-NMR (DMSO-d6): δ=2.68+2.78 (2H), 2.73+2.82 (3H), 2.95+2.97 (3H), 3.09+3.52 (3H), 3.67+4.26 (2H), 3.87+3.90 (3H), 7.09 (1H), 8.00 (1H), 8.22+8.37 (1H), 8.51+8.56 (1H), 9.18+9.40 (1H), 12.93 (1H) ppm.

Example 47

N-[3-(Dimethylamino)-3-oxopropyl]-7-[(6-isopropoxy-1H-indazol-5-yl)amino]-N-methyl[1,3]thiazolo[5,4-d]pyrimidine-2-carboxamide

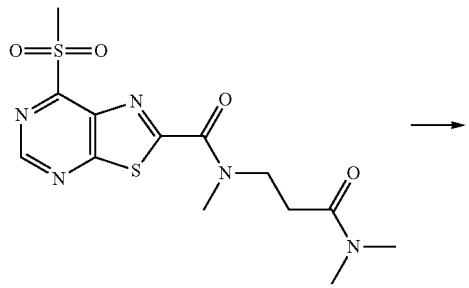

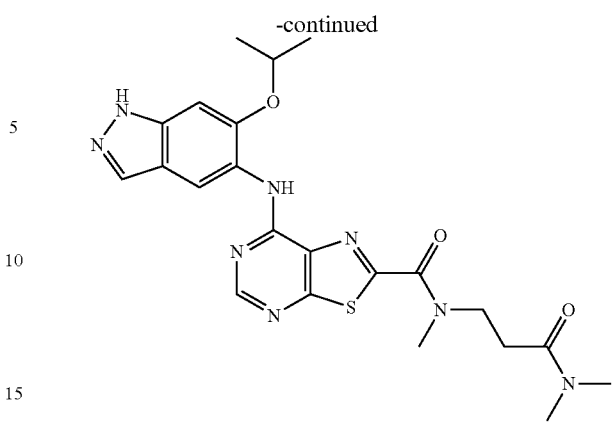

95 mg (256 μmol) N-[3-(dimethylamino)-3-oxopropyl]-N-methyl-7-(methylsulfonyl)[1,3]thiazolo[5,4-d]pyrimidine-2-carboxamide (prepared according to intermediate example 40a) were transformed in analogy to example 1 using 6-isopropoxy-1H-indazol-5-amine (prepared according to intermediate example 17d) to give after working up and purification 24.8 mg (19%) of the title compound.

$^1$H-NMR (DMSO-d6): δ=1.29+1.31 (6H), 2.65-2.75 (2H), 2.68+2.82 (3H), 2.90+2.97 (3H), 3.07+3.61 (3H), 3.69+4.32 (2H), 4.71-4.83 (1H), 7.11+7.13 (1H), 8.00+8.01 (1H), 8.52+8.71 (1H), 8.61+8.66 (1H), 9.15+9.17 (1H), 12.83 (1H) ppm.

Further, the compounds of formula I of the present invention can be converted to any salt as described herein, by any method which is known to the person skilled in the art. Similarly, any salt of a compound of formula I of the present invention can be converted into the free compound, by any method which is known to the person skilled in the art.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant serin threonin kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Biological Assays

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

MKNK1 Kinase Assay

MKNK1-inhibitory activity of compounds of the present invention was quantified employing the MKNK1 TR-FRET assay as described in the following paragraphs.

A recombinant fusion protein of Glutathione-S-Transferase (GST, N-terminally) and human full-lengt MKNK1 (amino acids 1-424 and T344D of accession number BAA 19885.1), expressed in insect cells using baculovirus expression system and purified via glutathione sepharose affinity chromatography, was purchased from Carna Biosciences (product no 02-145) and used as enzyme. As substrate for the kinase reaction the biotinylated peptide biotin-Ahx-IKKRKLTRRKSLKG (C-terminus in amide form) was used which can be purchased e.g. form the company Biosyntan (Berlin-Buch, Germany).

For the assay 50 nL of a 100 fold concentrated solution of the test compound in DMSO was pipetted into a black low volume 384 well microtiter plate (Greiner Bio-One, Frickenhausen, Germany), 2 µL of a solution of MKNK1 in aqueous assay buffer [50 mM HEPES pH 7.5, 5 mM $MgCl_2$, 1.0 mM dithiothreitol, 0.005% (v/v) Nonidet-P40 (Sigma)] was added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 16.7 µM=>final conc. in the 5 µL assay volume is 10 µM) and substrate (0.1 µM=>final conc. in the 5 µL assay volume is 0.06 µM) in assay buffer and the resulting mixture was incubated for a reaction time of 45 min at 22° C. The concentration of MKNK1 was adjusted depending of the activity of the enzyme lot and was chosen appropriate to have the assay in the linear range, typical concentrations were in the range of 0.05 µg/ml. The reaction was stopped by the addition of 5 µL of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 labeled ProteinG

[Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm were measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated.

MKNK1 Kinase High ATP Assay

MKNK1-inhibitory activity at high ATP of compounds of the present invention after their preincubation with MKNK1 was quantified employing the TR-FRET-based MKNK1 high ATP assay as described in the following paragraphs.

A recombinant fusion protein of Glutathione-S-Transferase (GST, N-terminally) and human full-length MKNK1 (amino acids 1-424 and T344D of accession number BAA 19885.1), expressed in insect cells using baculovirus expression system and purified via glutathione sepharose affinity chromatography, was purchased from Carna Biosciences (product no 02-145) and used as enzyme. As substrate for the kinase reaction the biotinylated peptide biotin-Ahx-IKKRKLTRRKSLKG (C-terminus in amide form) was used, which can be purchased e.g. from the company Biosyntan (Berlin-Buch, Germany).

For the assay 50 nL of a 100 fold concentrated solution of the test compound in DMSO was pipetted into a black low volume 384 well microtiter plate (Greiner Bio-One, Frickenhausen, Germany), 2 µL of a solution of MKNK1 in aqueous assay buffer [50 mM HEPES pH 7.5, 5 mM $MgCl_2$, 1.0 mM dithiothreitol, 0.005% (v/v) Nonidet-P40 (Sigma)] was added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 3.3 mM=>final conc. in the 5 µL assay volume is 2 mM) and substrate (0.1 µM=>final conc. in the 5 µL assay volume is 0.06 µM) in assay buffer and the resulting mixture was incubated for a reaction time of 30 min at 22° C. The concentration of MKNK1 was adjusted depending of the activity of the enzyme lot and was chosen appropriate to have the assay in the linear range, typical concentrations were in the range of 0.003 µg/mL. The reaction was stopped by the addition of 5 µL of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm were measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (e.g. 20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial dilutions, the exact concentrations may vary depending on the pipettor used) in duplicate values for each concentration and $IC_{50}$ values were calculated. Data are presented in Table 1.

TABLE 1

| Example | MKNK1 $IC_{50}$ [nM] |
|---------|----------------------|
| 1       | 37                   |
| 2       | 87                   |
| 3       | 197                  |
| 4       | 20                   |
| 5       | 25                   |
| 6       | n.d.                 |
| 7       | 354                  |
| 8       | 56                   |
| 9       | 36                   |
| 10      | 54                   |
| 11      | 35                   |
| 12      | 173                  |
| 13      | 122                  |
| 14      | 126                  |
| 15      | 47                   |
| 16      | 186                  |
| 17      | 229                  |
| 18      | 104                  |
| 19      | 159                  |
| 20      | 36                   |
| 21      | 100                  |
| 22      | 38                   |
| 23      | 51                   |
| 24      | n.d.                 |
| 25      | 10000                |
| 26      | 85                   |
| 27      | 408                  |
| 28      | 1080                 |
| 29      | 199                  |
| 30      | 42                   |
| 31      | 188                  |
| 32      | 137                  |
| 33      | 17                   |
| 34      | 34                   |
| 35      | 102                  |
| 36      | 81                   |
| 37      | 445                  |
| 38      | 136                  |
| 39      | 98                   |
| 40      | 49                   |
| 41      | 2750                 |
| 42      | 125                  |
| 43      | 202                  |
| 44      | 52                   |
| 45      | 57                   |
| 46      | 184                  |
| 47      | 32                   | n.d.: not yet determined

MKNK 2 Kinase High ATP Assay

MKNK 2-inhibitory activity at high ATP of compounds of the present invention after their preincubation with MKNK 2 was quantified employing the TR-FRET-based MKNK 2 high ATP assay as described in the following paragraphs.

A recombinant fusion protein of Glutathione-S-Transferase (GST, N-terminally) and human full-lengt MKNK 2 (Genbank accession number NP_060042.2), expressed in insect cells using baculovirus expression system, purified via glutathione sepharose affinity chromatography, and activated in vitro with MAPK12, was purchased from Invitrogen (product no PV5608) and used as enzyme. As substrate for the kinase reaction the biotinylated peptide biotin-Ahx-IKKRKLTRRKSLKG (C-terminus in amide form) was used which can be purchased e.g. form the company Biosyntan (Berlin-Buch, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of MKNK 2 in aqueous assay buffer [50 mM HEPES pH 7.5, 5 mM MgCl$_2$, 1.0 mM dithiothreitol, 0.005% (v/v) Nonidet-P40 (G-Biosciences, St. Louis, USA)] was added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 3.3 mM=>final conc. in the 5 µl assay volume is 2 mM) and substrate (0.1 µM=>final conc. in the 5 µl assay volume is 0.06 µM) in assay buffer and the resulting mixture was incubated for a reaction time of 30 min at 22° C. The concentration of MKNK 2 was adjusted depending of the activity of the enzyme lot and was chosen appropriate to have the assay in the linear range, typical concentrations were in the range of 0.0045 µg/ml. The reaction was stopped by the addition of 5 µl of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL665. Therefore, the fluorescence emissions at 620 nm and 665 nm after excitation at 350 nm were measured in a TR-FRET reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (e.g. 20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial dilutions, the exact concentrations may vary depending on the pipettor used) in duplicate values for each concentration and IC$_{50}$ values were calculated.

EGFR Kinase Assay

EGFR inhibitory activity of compounds of the present invention was quantified employing the TR-FRET based EGFR assay as described in the following paragraphs.

Epidermal Growth Factor Receptor (EGFR) affinity purified from human carcinoma A431 cells (Sigma-Aldrich, # E3641) was used as kinase. As substrate for the kinase reaction the biotinylated peptide biotin-Ahx-AEEEEYFEL-VAKKK (C-terminus in amid form) was used which can be purchased e.g. form the company Biosynthan GmbH (Berlin-Buch, Germany).

For the assay 50 nL of a 100 fold concentrated solution of the test compound in DMSO was pipetted into a black low volume 384 well microtiter plate (Greiner Bio-One, Frickenhausen, Germany), 2 µL of a solution of EGFR in aqueous assay [50 mM Hepes/HCl pH 7.0, 1 mM MgCl$_2$, 5 mM MnCl$_2$, 0.5 mM activated sodium ortho-vanadate, 0.005% (v/v) Tween-20] were added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 16.7 µM=>final conc. in the 5 µL assay volume is 10 µM) and substrate (1.67 µM=>final conc. in the 5 µL assay volume is 1 µM) in assay buffer and the resulting mixture was incubated for a reaction time of 30 min at 22° C. The concentration of EGFR was adjusted depending of the activity of the enzyme lot and was chosen appropriate to have the assay in the linear range, typical concentration were in the range of 3 U/nnl. The reaction was stopped by the addition of 5 µl of a solution of HTRF detection reagents (0.1 µM streptavidine-XL665 [Cis Biointernational] and 1 nM PT66-Tb-Chelate, an terbium-chelate labelled anti-phospho-tyrosine antibody from Cis Biointernational [instead of the PT66-Tb-chelate PT66-Eu-Cryptate from Perkin Elmer can also be used]) in an aqueous EDTA-solution (80 mM EDTA, 0.2% (w/v) bovine serum albumin in 50 mM HEPES pH 7.5).

The resulting mixture was incubated 1 h at 22° C. to allow the binding of the biotinylated phosphorylated peptide to the streptavidine-XL665 and the PT66-Eu-Chelate. Subsequently the amount of phosphorylated substrate was evaluated by measurement of the resonance energy transfer from the PT66-Eu-Chelate to the streptavidine-XL665. Therefore, the fluorescence emissions at 620 nm and 665 nm after excitation at 337 nm were measured in a HTRF reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (e.g. 20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial dilutions, the exact concentrations may vary depending on the pipettor used) in duplicate values for each concentration and IC$_{50}$ values were calculated.

CDK2/CycE Kinase Assay

CDK2/CycE inhibitory activity of compounds of the present invention can be quantified employing the CDK2/CycE TR-FRET assay as described in the following paragraphs.

Recombinant fusion proteins of GST and human CDK2 and of GST and human CycE, expressed in insect cells (Sf9) and purified by Glutathion-Sepharose affinity chromatography, can be purchased from ProQinase GmbH (Freiburg, Germany). As substrate for the kinase reaction biotinylated peptide biotin-Ttds-YISPLKSPYKISEG (C-terminus in amid form) can be used which can be purchased e.g. from the company JERINI peptide technologies (Berlin, Germany).

For the assay 50 nL of a 100 fold concentrated solution of the test compound in DMSO is pipetted into a black low volume 384 well microtiter plate (Greiner Bio-One, Frickenhausen, Germany), 2 μL of a solution of CDK2/CycE in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] are added and the mixture is incubated for 15 min at 22° C. to allow pre-binding of the test compounds to the enzyme before the start of the kinase reaction. Then the kinase reaction is started by the addition of 3 μL of a solution of adenosine-tri-phosphate (ATP, 16.7 μM=>final conc. in the 5 μL assay volume is 10 μM) and substrate (1.25 μM=>final conc. in the 5 μL assay volume is 0.75 μM) in assay buffer and the resulting mixture is incubated for a reaction time of 25 min at 22° C. The concentration of CDK2/CycE is adjusted depending of the activity of the enzyme lot and is chosen appropriate to have the assay in the linear range, typical concentrations ae in the range of 130 ng/ml. The reaction is stopped by the addition of 5 μL of a solution of TR-FRET detection reagents (0.2 μM streptavidine-XL665 [Cisbio Bioassays, Codolet, France] and 1 nM anti-RB(pSer807/pSer811)-antibody from BD Pharmingen [#558389] and 1.2 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (100 mM EDTA, 0.2% (w/v) bovine serum albumin in 100 mM HEPES/NaOH pH 7.0).

The resulting mixture is incubated 1 h at 22° C. to allow the formation of complex between the phosphorylated biotinylated peptide and the detection reagents. Subsequently the amount of phosphorylated substrate is evaluated by measurement of the resonance energy transfer from the Eu-chelate to the streptavidine-XL. Therefore, the fluorescence emissions at 620 nm and 665 nm after excitation at 350 nm is measured in a TR-FRET reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Usually the test compounds are tested on the same microtiterplate in 11 different concentrations in the range of 20 μM to 0.1 nM (20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values are calculated.

PDGFRβ Kinase Assay

PDGFRβ inhibitory activity of compounds of the present invention can be quantified employing the PDGFRβ HTRF assay as described in the following paragraphs.

As kinase, a GST-His fusion protein containing a C-terminal fragment of human PDGFRβ (amino acids 561-1106, expressed in insect cells [SF9] and purified by affinity chromatography, purchased from Proqinase [Freiburg i.Brsg., Germany] is used. As substrate for the kinase reaction the biotinylated poly-Glu,Tyr (4:1) copolymer (#61GT0BLA) from Cis Biointernational (Marcoule, France) is used.

For the assay 50 nL of a 100 fold concentrated solution of the test compound in DMSO is pipetted into a black low volume 384 well microtiter plate (Greiner Bio-One, Frickenhausen, Germany), 2 μL of a solution of PDGFRβ in aqueous assay buffer [50 mM HEPES/NaOH pH 7.5, 10 mM $MgCl_2$, 2.5 mM dithiothreitol, 0.01% (v/v) Triton-X100 (Sigma)] are added and the mixture was incubated for 15 min at 22° C. to allow pre-binding of the test compounds to the enzyme before the start of the kinase reaction. Then the kinase reaction is started by the addition of 3 μL of a solution of adenosine-tri-phosphate (ATP, 16.7 μM=>final conc. in the 5 μL assay volume is 10 μM) and substrate (2.27 μg/ml=>final conc. in the 5 μL assay volume is 1.36 μg/ml [~30 nM]) in assay buffer and the resulting mixture is incubated for a reaction time of 25 min at 22° C. The concentration of PDGFRβ in the assay is adjusted depending of the activity of the enzyme lot and is chosen appropriate to have the assay in the linear range, typical enzyme concentrations are in the range of about 125 μg/μL (final conc. in the 5 μL assay volume). The reaction is stopped by the addition of 5 μL of a solution of HTRF detection reagents (200 nM streptavidine-XLent [Cis Biointernational] and 1.4 nM PT66-Eu-Chelate, an europium-chelate labelled anti-phospho-tyrosine antibody from Perkin Elmer [instead of the PT66-Eu-chelate PT66-Tb-Cryptate from Cis Biointernational can also be used]) in an aqueous EDTA-solution (100 mM EDTA, 0.2% (w/v) bovine serum albumin in 50 mM HEPES/NaOH pH 7.5).

The resulting mixture is incubated 1 h at 22° C. to allow the binding of the biotinylated phosphorylated peptide to the streptavidine-XLent and the PT66-Eu-Chelate. Subsequently the amount of phosphorylated substrate is evaluated by measurement of the resonance energy transfer from the PT66-Eu-Chelate to the streptavidine-XLent. Therefore, the fluorescence emissions at 620 nm and 665 nm after excitation at 350 nm is measured in a HTRF reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Normally test compound are tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values are calculated.

Fyn Kinase Assay

C-terminally His6-tagged human recombinant kinase domain of the human T-Fyn expressed in baculovirus infected insect cells (purchased from Invitrogen, P3042) is used as kinase. As substrate for the kinase reaction the biotinylated peptide biotin-KVEKIGEGTYGW (C-terminus in amid form) is used which can be purchased e.g. form the company Biosynthan GmbH (Berlin-Buch, Germany).

For the assay 50 nL of a 100 fold concentrated solution of the test compound in DMSO is pipetted into a black low volume 384 well microtiter plate (Greiner Bio-One, Frickenhausen, Germany), 2 μL of a solution of T-Fyn in aqueous assay buffer [25 mM Tris/HCl pH 7.2, 25 mM $MgCl_2$, 2 mM dithiothreitol, 0.1% (w/v) bovine serum albumin, 0.03% (v/v) Nonidet-P40 (Sigma)]. are added and the mixture is incubated for 15 min at 22° C. to allow pre-binding of the test compounds to the enzyme before the start of the kinase reaction. Then the kinase reaction is started by the addition of 3 μL of a solution of adenosine-tri-phosphate (ATP, 16.7 μM=>final conc. in the 5 μL assay volume is 10 μM) and substrate (2 µM=>final conc. in the 5 µL assay volume is 1.2 µM) in assay buffer and the resulting mixture is incubated for a reaction time of 60 min at 22° C. The concentration of Fyn is adjusted depending of the activity of the enzyme lot and is chosen appropriate to have the assay in the linear range, typical concentration was 0.13 nM. The reaction is stopped by the addition of 5 µL of a solution of HTRF detection reagents (0.2 µM streptavidine-XL [Cisbio Bioassays, Codolet, France) and 0.66 nM PT66-Eu-Chelate, an europium-chelate labelled anti-phospho-tyrosine antibody from Perkin Elmer [instead of the PT66-Eu-chelate PT66-Tb-Cryptate from Cisbio Bioassays can also be used]) in an aqueous EDTA-solution (125 mM EDTA, 0.2% (w/v) bovine serum albumin in 50 mM HEPES/NaOH pH 7.0).

The resulting mixture is incubated 1 h at 22° C. to allow the binding of the biotinylated phosphorylated peptide to the streptavidine-XL and the PT66-Eu-Chelate. Subsequently the amount of phosphorylated substrate is evaluated by measurement of the resonance energy transfer from the PT66-Eu-Chelate to the streptavidine-XL. Therefore, the fluorescence emissions at 620 nm and 665 nm after excitation at 350 nm is measured in a HTRF reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Normally test compounds are tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values are calculated.

Flt4 Kinase Assay

Flt4 inhibitory activity of compounds of the present invention can be quantified employing the Flt4 TR-FRET assay as described in the following paragraphs.

As kinase, a GST-His fusion protein containing a C-terminal fragment of human Flt4 (amino acids 799-1298, expressed in insect cells [SF9] and purified by affinity chromatography, purchased from Proqinase [Freiburg i.Brsg., Germany] is used. As substrate for the kinase reaction the biotinylated peptide Biotin-Ahx-GGEEEEY-FELVKKKK (C-terminus in amide form, purchased from Biosyntan, Berlin-Buch, Germany) is used.

For the assay 50 nL of a 100 fold concentrated solution of the test compound in DMSO was pipetted into a black low volume 384 well microtiter plate (Greiner Bio-One, Frickenhausen, Germany), 2 µL of a solution of Flt4 in aqueous assay buffer [25 mM HEPES pH 7.5, 10 mM $MgCl_2$, 2 mM dithiothreitol, 0.01% (v/v) Triton-X100 (Sigma), 0.5 mM EGTA, and 5 mM β-phospho-glycerol] are added and the mixture is incubated for 15 min at 22° C. to allow pre-binding of the test compounds to the enzyme before the start of the kinase reaction. Then the kinase reaction is started by the addition of 3 µL of a solution of adenosine-tri-phosphate (ATP, 16.7 µM=>final conc. in the 5 µL assay volume is 10 µM) and substrate (1.67 µM=>final conc. in the 5 µL assay volume is 1 µM) in assay buffer and the resulting mixture is incubated for a reaction time of 45 min at 22° C. The concentration of Flt4 in the assay is adjusted depending of the activity of the enzyme lot and was chosen appropriate to have the assay in the linear range, typical enzyme concentrations are in the range of about 120 pg/µL (final conc. in the 5 µL assay volume). The reaction is stopped by the addition of 5 µL of a solution of HTRF detection reagents (200 nM streptavidine-XL665 [Cis Biointernational] and 1 nM PT66-Tb-Cryptate, an terbium-cryptate labelled anti-phospho-tyrosine antibody from Cisbio Bioassays (Codolet, France) in an aqueous EDTA-solution (50 mM EDTA, 0.2% (w/v) bovine serum albumin in 50 mM HEPES pH 7.5).

The resulting mixture is incubated 1 h at 22° C. to allow the binding of the biotinylated phosphorylated peptide to the streptavidine-XL665 and the PT66-Tb-Cryptate. Subsequently the amount of phosphorylated substrate is evaluated by measurement of the resonance energy transfer from the PT66-Tb-Cryptate to the streptavidine-XL665. Therefore, the fluorescence emissions at 620 nm and 665 nm after excitation at 350 nm is measured in a HTRF reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Normally test compound are tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values are calculated.

TrkA Kinase Assay

TrkA inhibitory activity of compounds of the present invention can be quantified employing the TrkA HTRF assay as described in the following paragraphs.

As kinase, a GST-His fusion protein containing a C-terminal fragment of human TrkA (amino acids 443-796, expressed in insect cells [SF9] and purified by affinity chromatography, purchased from Proqinase [Freiburg i.Brsg., Germany] is used. As substrate for the kinase reaction the biotinylated poly-Glu,Tyr (4:1) copolymer (#61GT0BLA) from Cis Biointernational (Marcoule, France) is used.

For the assay 50 nL of a 100 fold concentrated solution of the test compound in DMSO is pipetted into a black low volume 384 well microtiter plate (Greiner Bio-One, Frickenhausen, Germany), 2 µL of a solution of TrkA in aqueous assay buffer [8 mM MOPS/HCl pH 7.0, 10 mM $MgCl_2$, 1 mM dithiothreitol, 0.01% (v/v) NP-40 (Sigma), 0.2 mM EDTA] are added and the mixture was incubated for 15 min at 22° C. to allow pre-binding of the test compounds to the enzyme before the start of the kinase reaction. Then the kinase reaction is started by the addition of 3 µL of a solution of adenosine-tri-phosphate (ATP, 16.7 µM=>final conc. in the 5 µL assay volume is 10 µM) and substrate (2.27 µg/ml=>final conc. in the 5 µL assay volume is 1.36 µg/ml [~30 nM]) in assay buffer and the resulting mixture is incubated for a reaction time of 60 min at 22° C. The concentration of TrkA in the assay is adjusted depending of the activity of the enzyme lot and is chosen appropriate to have the assay in the linear range, typical enzyme concentrations are in the range of about 20 pg/µL (final conc. in the 5 µL assay volume). The reaction is stopped by the addition of 5 µL of a solution of HTRF detection reagents (30 nM streptavidine-XL665 [Cis Biointernational] and 1.4 nM PT66-Eu-Chelate, an europium-chelate labelled anti-phospho-tyrosine antibody from Perkin Elmer [instead of the PT66-Eu-chelate PT66-Tb-Cryptate from Cis Biointernational can also be used]) in an aqueous EDTA-solution (100 mM EDTA, 0.2% (w/v) bovine serum albumin in 50 mM HEPES/NaOH pH 7.5).

The resulting mixture is incubated 1 h at 22° C. to allow the binding of the biotinylated phosphorylated peptide to the streptavidine-XL665 and the PT66-Eu-Chelate. Subsequently the amount of phosphorylated substrate is evaluated by measurement of the resonance energy transfer from the PT66-Eu-Chelate to the streptavidine-XL665. Therefore, the fluorescence emissions at 620 nm and 665 nm after excitation at 350 nm is measured in a HTRF reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Normally test compound are tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values are calculated.

AlphaScreen SureFire eIF4E Ser209 Phosphorylation Assay

The AlphaScreen SureFire eIF4E Ser209 phoshorylation assay can be used to measure the phosphorylation of endogenous eIF4E in cellular lysates. The AlphaScreen SureFire technology allows the detection of phosphorylated proteins in cellular lysates. In this assay, sandwich antibody complexes, which are only formed in the presence of the analyte (p-eIF4E Ser209), are captured by AlphaScreen donor and acceptor beads, bringing them into close proximity. The excitation of the donor bead provokes the release of singlet oxygen molecules that triggers a cascade of energy transfer in the Acceptor beads, resulting in the emission of light at 520-620 nm.

Surefire EIF4e Alphascreen in A549 Cells with 20% FCS Stimulation

For the assay the AlphaScreen SureFire p-eIF4E Ser209 10K Assay Kit and the AlphaScreen ProteinA Kit (for 10K assay points) both from Perkin Elmer are used.

On day one 50.000 A549 cells are plated in a 96-well plate in 100 μL per well in growth medium (DMEM/Hams' F12 with stable Glutamin, 10% FCS) and incubated at 37° C. After attachment of the cells, medium is changed to starving medium (DMEM, 0.1% FCS, without Glucose, with Glutamin, supplemented with 5 g/L Maltose). On day two, test compounds are serially diluted in 50 μL starving medium with a final DMSO concentration of 1% and are added to A549 cells in test plates at a final concentration range from as high 10 μM to as low 10 nM depending on the activities of the tested compounds. Treated cells are incubated at 37° C. for 2 h. 37 ul FCS is added to the wells (=final FCS concentration 20%) for 20 min. Then medium is removed and cells are lysed by adding 50 μL lysis buffer. Plates are then agitated on a plate shaker for 10 min. After 10 min lysis time, 4 μL of the lysate is transfered to a 384 well plate (Proxiplate from Perkin Elmer) and 5 μL Reaction Buffer plus Activation Buffer mix containing AlphaScreen Acceptor beads is added. Plates are sealed with TopSeal-A adhesive film, gently agitated on a plate shaker for 2 hours at room temperature. Afterwards 2 μL Dilution buffer with AlphaScreen Donor beads are added under subdued light and plates are sealed again with TopSeal-A adhesive film and covered with foil. Incubation takes place for further 2 h gently agitation at room temperature. Plates are then measured in an EnVision reader (Perkin Elmer) with the AlphaScreen program. Each data point (compound dilution) is measured as triplicate.

Proliferation Assays

The tumor cell proliferation assay which can be used to test the compounds of the present invention involves a readout called Cell Titer-Glow® Luminescent Cell Viability Assay developed by Promega® (B. A. Cunningham, "A Growing Issue: Cell Proliferation Assays, Modern kits ease quantification of cell growth", The Scientist 2001, 15(13), 26; S. P. Crouch et al., "The use of ATP bioluminescence as a measure of cell proliferation and cytotoxicity", Journal of Immunological Methods 1993, 160, 81-88), that measures inhibition of cell proliferation. Generation of a luminescent signal corresponds to the amount of ATP present, which is directly proportional to the number of metabolically active (proliferating) cells.

In Vitro Tumor Cell Proliferation Assay:

Cultivated tumour cells (MOLM-13 (human acute myeloid leukemia cells obtained from DSMZ # ACC 554), JJN-3 (human plasma cell leukemia cells obtained from DSMZ # ACC 541), Ramos (RA1) (human Burkitt's lymphoma cells obtained from ATCC # CRL-159)) are plated at a density of 2,500 cells/well (JJN-3), 3,000 cells/well (MOLM-13), 4,000 cells/well (Ramos (RA1)), in a 96-well multititer plate (Costar 3603 black/clear bottom) in 100 μL of their respective growth medium supplemented with 10% fetal calf serum. After 24 hours, the cells of one plate (zero-point plate) are measured for viability. Therefore, 70 μL/well CTG solution (Promega Cell Titer Glo solution (catalog # G755B and G756B)) is added to zero-point plate. The plates are mixed for two minutes on orbital shaker to ensure cell lysis and incubated for ten minutes at room temperature in the dark to stabilize luminescence signal. The samples are read on a VICTOR 3 plate reader. In parallel, serially test compounds are diluted in growth medium, and 50 μL of 3× dilutions/well are pipetted into the test plates (final concentrations: 0 μM, as well as in the range of 0.001-30 μM). The final concentration of the solvent dimethyl sulfoxide is 0.3-0.4%. The cells are incubated for 3 days in the presence of test substances. 105 μL/well CTG solution (Promega Cell Titer Glo solution (catalog # G755B and G756B)) is added to the test wells. The plates are mixed for 2 minutes on an orbital shaker to ensure cell lysis and incubated for 10 min at room temperature in the dark to stabilize luminescence signal. The samples are read on a VICTOR 3 plate reader. The change of cell number, in percent, is calculated by normalization of the measured values to the extinction values of the zero-point plate (=0%) and the extinction of the untreated (0 μm) cells (=100%).

Overview Cell Lines for Proliferation Assays

| Cell line | Origin | Cell number/well | Culture Medium |
|---|---|---|---|
| MOLM-13 (obtained from DSMZ # ACC 554) | human acute myeloid leukemia | 3000 | RPMI 1640 with stable Glutamin with 10% Fetal Bovine Serum |

| Cell line | Origin | Cell number/well | Culture Medium |
|---|---|---|---|
| JJN-3 (obtained from DSMZ # ACC 541) | human plasma cell leukemia | 2500 | 45% Dulbecco's Modified Eagle Medium with stable Glutamin, 45% Iscove's Modified Dulbecco's Media with stable Glutamin and 10% Fetal Bovine Serum |
| Ramos (RA1) (obtained from ATCC # CRL-159) | human Burkitt's lymphoma | 4000 | RPMI 1640 media with stable Glutamin with 10% Fetal Bovine Serum |

Thus the compounds of the present invention effectively inhibit one or more kinases and are therefore suitable for the treatment or prophylaxis of diseases of uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK, more particularly in which the diseases of uncontrolled cell growth, proliferation and/or survival, inappropriate cellular immune responses, or inappropriate cellular inflammatory responses are haemotological tumours, solid tumours and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The invention claimed is:

1. A compound of general formula I:

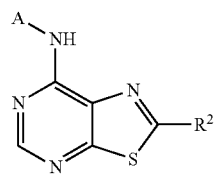

in which:

A represents a group selected from:

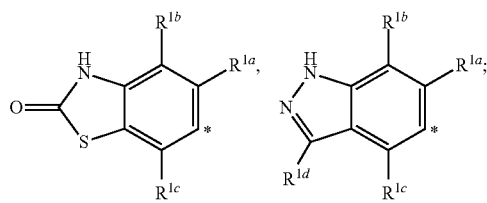

wherein * indicates the point of attachment of said groups with the rest of the molecule;

$R^{1a}$, $R^{1b}$, $R^{1c}$, $R^{1d}$ are the same or different and are independently selected from $R^1$;

$R^1$ represents a hydrogen atom or a halogen atom or a hydroxy-, cyano-, $C_1$-$C_6$-alkyl-, $C_2$-$C_6$-alkenyl-, $C_2$-$C_6$-alkynyl-, $C_1$-$C_6$-alkoxy-, halo-$C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O—, —$NR^{5a}R^{5b}$, —$SCF_3$ or —$SF_5$ group;

wherein said $C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O— group is optionally substituted, identically or differently, with 1, 2, 3, 4 or 5 $R^4$ groups;

$R^2$ represents a hydrogen atom, a halogen atom or a group selected from: $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl-, heteroaryl-, cyano-, —$(CH_2)_q$—X—$(CH_2)_p$—$R^3$;

wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl- or heteroaryl-group is optionally substituted, identically or differently, with 1, 2, 3, 4 or 5 $R^4$ groups;

X represents a bond or a bivalent group selected from:
—O—, —S—, —S(=O)—, —S(=O)$_2$—,
—S(=O)—$(NR^{3a})$—, —$(NR^{3a})$—S(=O)—,
—S(=O)$_2$—$(NR^{3a})$—, —$(NR^{3a})$—S(=O)$_2$—,
—C(=O)—, —$(NR^{3a})$—, —C(=O)—O—, —O—C(=O)—, —C(=S)—O—, —O—C(=S)—,
—C(=O)—$(NR^{3a})$—, —$(NR^{3a})$—C(=O)—,
—$(NR^{3a})$—C(=O)—$(NR^{3b})$—, —O—C(=O)—$(NR^{3a})$—, —$(NR^{3a})$—C(=O)—O—;

$R^{3a}$, $R^{3b}$ are the same or different and are independently selected from $R^3$;

$R^3$ represents a hydrogen atom or a group selected from $C_1$-$C_6$-alkyl-, $C_3$-$C_6$-cycloalkyl-, 3- to 10-membered heterocycloalkyl-, aryl-, heteroaryl-;

wherein said $C_1$-$C_6$-alkyl-, $C_3$-$C_6$-cycloalkyl-, 3- to 10-membered heterocycloalkyl-, aryl- or heteroaryl-group is optionally substituted, identically or differently, with 1, 2, 3, 4 or 5 $R^4$ groups;

or $R^3$ together with $R^{3a}$ or $R^{3b}$ represent a 3- to 10-membered heterocycloalkyl- or a 4- to 10-membered heterocycloalkenyl-group, which is optionally substituted, identically or differently, with 1, 2, 3, 4 or 5 $R^4$ groups;

$R^4$ represents halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—,
—C(=O)—$R^5$, —C(=O)—O—$R^5$, —O—C(=O)—$R^5$, —$N(R^{5a})$—C(=O)—$R^{5b}$, —$N(R^{5a})$—C(=O)—$NR^{5b}R^{5c}$, —$NR^{5a}R^{5b}$, —C(=O)—$NR^{5a}R^{5b}$,
$R^5$—S—, $R^5$—S(=O)—, $R^5$—S(=O)$_2$—, —N(R$^{5a}$)—S(=O)—R$^{5b}$,  —S(=O)—NR$^{5a}$R$^{5b}$,
—N(R$^{5a}$)—S(=O)$_2$—R$^{5b}$,  —S(=O)$_2$—NR$^{5a}$R$^{5b}$,
—S(=O)(=NR$^{5a}$)R$^{5b}$,  —S(=O)(=NR$^{5a}$)R$^{5b}$  or
—N=S(=O)(R$^{5a}$)R$^{5b}$;

R$^{5a}$, R$^{5b}$, R$^{5c}$ are the same or different and are independently selected from R$^5$;

R$^5$ represents a hydrogen atom, a C$_1$-C$_6$-alkyl- or a C$_3$-C$_6$-cycloalkyl-group;
or
R$^{5a}$ and R$^{5b}$,
or R$^{5a}$ and R$^{5c}$,
or R$^{5b}$ and R$^{5c}$ together may form a C$_2$-C$_6$-alkylene group, in which optionally one methylene can be replaced by —O—, —C(=O)—, —NH—, or —N(C$_1$-C$_4$-alkyl)-;
p represents an integer of 0, 1, 2 or 3;
q represents an integer of 0, 1, 2 or 3;
or a tautomer, an N-oxide, a hydrate, a solvate, or a salt thereof, or a mixture of same.

2. A compound according to claim 1, wherein:
A represents:

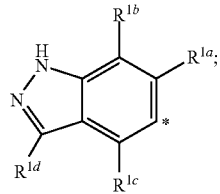

wherein * indicates the point of attachment of said groups with the rest of the molecule.

3. A compound according to claim 1, wherein:
A represents:

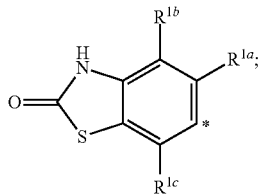

wherein * indicates the point of attachment of said groups with the rest of the molecule.

4. A compound according to claim 1, wherein:
R$^{1a}$ represents a hydrogen atom or a group selected from: C$_1$-C$_3$-alkyl-, C$_1$-C$_3$-alkoxy-, halo-;
R$^{1b}$, R$^{1c}$, R$^{1d}$ represents a hydrogen atom.

5. A compound according to claim 1, wherein:
R$^{1a}$ does not represent a hydrogen atom.

6. A compound according to claim 1, wherein:
R$^2$ represents a hydrogen atom, a halogen atom, or a group selected from: C$_1$-C$_6$-alkyl-, C$_3$-C$_6$-cycloalkyl-, aryl-, cyano-, (CH$_2$)$_q$—X—(CH$_2$)$_p$—R$^3$;
wherein said C$_1$-C$_6$-alkyl-, C$_3$-C$_6$-cycloalkyl- or aryl-group is optionally substituted, identically or differently, with 1, 2 or 3 R$^4$ groups;
X represents a bond or a bivalent group selected from:
—O—,  —C(=O)—,  —C(=O)—(NR$^{3a}$)—,
—(NR$^{3a}$)—C(=O)—;
R$^{3a}$ represents a hydrogen atom or a group selected from C$_1$-C$_6$-alkyl-, C$_3$-C$_6$-cycloalkyl-, 3- to 10-membered heterocycloalkyl-, aryl-;

wherein said C$_1$-C$_6$-alkyl-, C$_3$-C$_6$-cycloalkyl-, 3- to 10-membered heterocycloalkyl- or aryl-group is optionally substituted, identically or differently, with 1, 2 or 3 R$^4$ groups;
R$^4$ represents halo-, hydroxy-, oxo-(O=), cyano-, nitro-, C$_1$-C$_6$-alkyl-, halo-C$_1$-C$_6$-alkyl-, C$_1$-C$_6$-alkoxy-, halo-C$_1$-C$_6$-alkoxy-, hydroxy-C$_1$-C$_6$-alkyl-, C$_1$-C$_6$-alkoxy-C$_1$-C$_6$-alkyl-, R$^5$—O—, —C(=O)—R$^5$, —C(=O)—O—R$^5$, —O—C(=O)—R$^5$, —C(=O)—NR$^{5a}$R$^{5b}$.

7. A compound according to claim 1, which is selected from the group consisting of:
6-{[2-(Cyclopropylmethyl)[1,3]thiazolo[5,4-d]pyrimidin-7-yl]amino}-1,3-benzothiazol-2(3H)-one,
6-[(2-Cyclobutyl[1,3]thiazolo[5,4-d]pyrimidin-7-yl)amino]-1,3-benzothiazol-2(3H)-one,
6-[(2-Cyclohexyl[1,3]thiazolo[5,4-d]pyrimidin-7-yl)amino]-1,3-benzothiazol-2(3H)-one,
2-Benzyl-N-(6-methoxy-1H-indazol-5-yl)[1,3]thiazolo[5,4-d]pyrimidin-7-amine,
N-(6-Methoxy-1H-indazol-5-yl)-2-(methoxymethyl)[1,3]thiazolo[5,4-d]pyrimidin-7-amine,
6-[(2-Cyclobutyl [1,3]thiazolo[5,4-d]pyrimidin-7-yl)amino]-5-methoxy-1,3-benzothiazol-2(3H)-one,
6-[(2-Cyclohexyl [1,3]thiazolo[5,4-d]pyrimidin-7-yl)amino]-5-methoxy-1,3-benzothiazol-2(3H)-one,
2-Cyclohexyl-N-(1H-indazol-5-yl)[1,3]thiazolo[5,4-d]pyrimidin-7-amine,
2-(Cyclopropylmethyl)-N-(1H-indazol-5-yl)[1,3]thiazolo[5,4-d]pyrimidin-7-amine,
2-Cyclobutyl-N-(1H-indazol-5-yl)[1,3]thiazolo[5,4-d]pyrimidin-7-amine,
2-Benzyl-N-(1H-indazol-5-yl)[1,3]thiazolo[5,4-d]pyrimidin-7-amine,
1-(3-Hydroxy-3-methylazetidin-1-yl)-4-[7-(1H-indazol-5-ylamino)[1,3]thiazolo[5,4-d]pyrimidin-2-yl]butan-1-one,
4-[7-(1H-Indazol-5-ylamino)[1,3]thiazolo[5,4-d]pyrimidin-2-yl]-N,N-dimethylbutanamide,
1-(3-Hydroxy-3-methylazetidin-1-yl)-3-[7-(1H-indazol-5-ylamino)[1,3]thiazolo[5,4-d]pyrimidin-2-yl]propan-1-one,
N-(6-Methoxy-1H-indazol-5-yl)[1,3]thiazolo[5,4-d]pyrimidin-7-amine,
N-(1H-Indazol-5-yl)[1,3]thiazolo[5,4-d]pyrimidin-7-amine,
2-(2-Phenylethyl)-N-[6-(propan-2-yloxy)-1H-indazol-5-yl][1,3]thiazolo[5,4-d]pyrimidin-7-amine,
5-Methoxy-6-([1,3]thiazolo[5,4-d]pyrimidin-7-ylamino)-1,3-benzothiazol-2(3H)-one,
6-([1,3]Thiazolo[5,4-d]pyrimidin-7-ylamino)-1,3-benzothiazol-2(3H)-one,
2-[(Benzyloxy)methyl]-N-(6-methoxy-1H-indazol-5-yl)[1,3]thiazolo[5,4-d]pyrimidin-7-amine,
3-[7-(1H-Indazol-5-ylamino)[1,3]thiazolo[5,4-d]pyrimidin-2-yl]-N,N-dimethylpropanamide,
N-(6-Methoxy-1H-indazol-5-yl)-2-(2-phenylethyl)[1,3]thiazolo[5,4-d]pyrimidin-7-amine,
N-(1H-Indazol-5-yl)-2-(2-phenylethyl)[1,3]thiazolo[5,4-d]pyrimidin-7-amine,
6-{[2-(2-Phenylethyl)[1,3]thiazolo[5,4-d]pyrimidin-7-yl]amino}-1,3-benzothiazol-2(3H)-one,
5-Methoxy-6-{[2-(2-phenylethyl)[1,3]thiazolo[5,4-d]pyrimidin-7-yl]amino}-1,3-benzothiazol-2(3H)-one,
4-{7-[(6-Methoxy-1H-indazol-5-yl)amino][1,3]thiazolo[5,4-d]pyrimidin-2-yl}-N,N-dimethylbutanamide, N,N-Dimethyl-7-[(2-oxo-2,3-dihydro-1,3-benzothiazol-6-yl)amino][1,3]thiazolo[5,4-d]pyrimidine-2-carboxamide,
7-[(5-Methoxy-2-oxo-2,3-dihydro-1,3-benzothiazol-6-yl)amino]-N,N-dimethyl [1,3]thiazolo[5,4-d]pyrimidine-2-carboxamide,
7-[(6-Methoxy-1H-indazol-5-yl)amino]-N,N-dimethyl [1,3]thiazolo[5,4-d]pyrimidine-2-carboxamide,
7-[(6-Ethoxy-1H-indazol-5-yl)amino]-N,N-dimethyl [1,3]thiazolo[5,4-d]pyrimidine-2-carboxamide,
[7-(1H-Indazol-5-ylamino)[1,3]thiazolo[5,4-d]pyrimidin-2-yl]piperidin-1-yl)methanone,
6-{[2-(Piperidin-1-ylcarbonyl)[1,3]thiazolo[5,4-d]pyrimidin-7-yl]amino}-1,3-benzothiazol-2(3H)-one,
{7-[(6-Methoxy-1H-indazol-5-yl)amino][1,3]thiazolo[5,4-d]pyrimidin-2-yl}(piperidin-1-yl)methanone,
{7-[(6-Ethoxy-1H-indazol-5-yl)amino][1,3]thiazolo[5,4-d]pyrimidin-2-yl}(piperidin-1-yl)methanone, Piperidin-1-yl(7-{[6-(propan-2-yloxy)-1H-indazol-5-yl]amino}[1,3]thiazolo[5,4-d]pyrimidin-2-yl)methanone,
N-[2-(Dimethylamino)-2-oxoethyl]-7-(1H-indazol-5-ylamino)-N-methyl [1,3]thiazolo[5,4-d]pyrimidine-2-carboxamide,
N-[2-(Dimethylamino)-2-oxoethyl]-N-methyl-7-[(2-oxo-2,3-dihydro-1,3-benzothiazol-6-yl)amino][1,3]thiazolo[5,4-d]pyrimidine-2-carboxamide,
N-[2-(Dimethylamino)-2-oxoethyl]-7-[(6-methoxy-1H-indazol-5-yl)amino]-N-methyl [1,3]thiazolo[5,4-d]pyrimidine-2-carboxamide,
N-[2-(Dimethylamino)-2-oxoethyl]-N-methyl-7-{[6-(propan-2-yloxy)-1H-indazol-5-yl]amino}[1,3]thiazolo[5,4-d]pyrimidine-2-carboxamide,
N-[3-(Dimethylamino)-3-oxopropyl]-7-(1H-indazol-5-ylamino)-N-methyl[1,3]thiazolo[5,4-d]pyrimidine-2-carboxamide,
N-[3-(Dimethylamino)-3-oxopropyl]-N-methyl-7-[(2-oxo-2,3-dihydro-1,3-benzothiazol-6-yl)amino][1,3]thiazolo[5,4-d]pyrimidine-2-carboxamide,
N-[3-(Dimethylamino)-3-oxopropyl]-7-[(6-ethoxy-1H-indazol-5-yl)amino]-N-methyl[1,3]thiazolo[5,4-d]pyrimidine-2-carboxamide,
7-(1H-Indazol-5-ylamino)-N,N-dimethyl[1,3]thiazolo[5,4-d]pyrimidine-2-carboxamide,
N,N-Dimethyl-7-{[6-(propan-2-yloxy)-1H-indazol-5-yl]amino}[1,3]thiazolo[5,4-d]pyrimidine-2-carboxamide,
N-[2-(Dimethylamino)-2-oxoethyl]-7-[(6-ethoxy-1H-indazol-5-yl)amino]-N-methyl[1,3]thiazolo[5,4-d]pyrimidine-2-carboxamide,
N-[3-(Dimethylamino)-3-oxopropyl]-7-[(6-methoxy-1H-indazol-5-yl)amino]-N-methyl[1,3]thiazolo[5,4-d]pyrimidine-2-carboxamide,
N-[3-(Dimethylamino)-3-oxopropyl]-7-[(6-isopropoxy-1H-indazol-5-yl)amino]-N-methyl[1,3]thiazolo[5,4-d]pyrimidine-2-carboxamide, or a tautomer, an N-oxide, a hydrate, a solvate, or a salt thereof, or a mixture of same.

8. A method of preparing a compound of general formula I according to claim 1, comprising reacting an intermediate compound of general formula III:

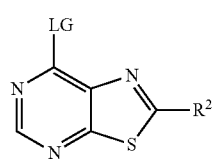

III in which $R^2$ is as defined in claim 1 and LG represents a leaving group;

with an intermediate compound of general formula II-A or II-B:

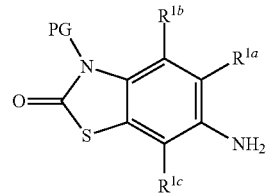

II-A

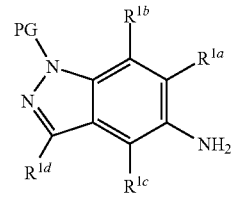

II-B in which $R^{1a}$, $R^{1b}$, $R^{1c}$ and $R^{1d}$ are as defined in claim 1 and PG represents a protective group or a hydrogen atom;

thus providing a compound of general formula I'-A, I'-B or I:

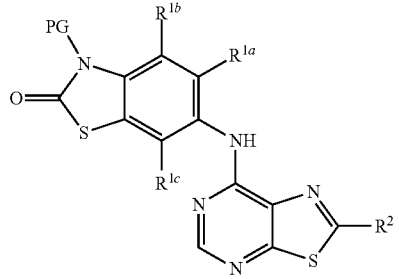

I'-A

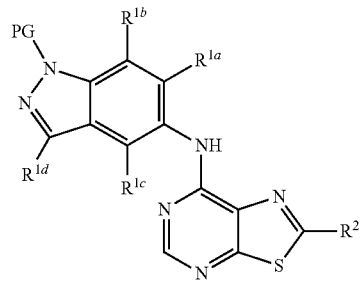

I'-B

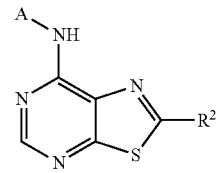

I in which $R^{1a}$, $R^{1b}$, $R^{1c}$, $R^{1d}$, $R^2$, and A are as defined in claim 1, PG represents a protective group or a hydrogen atom.

9. A compound selected from:

7-Chloro-2-(cyclopropylmethyl)[1,3]thiazolo[5,4-d]pyrimidine,

7-Chloro-2-cyclohexyl[1,3]thiazolo[5,4-d]pyrimidine,

7-Chloro-2-(methoxymethyl)[1,3]thiazolo[5,4-d]pyrimidine, 7-chloro-2-cyclobutyl[1,3]thiazolo[5,4-d]pyrimidine, ethyl 4-(7-chloro[1,3]thiazolo[5,4-d]pyrimidin-2-yl)butanoate, ethyl 3-(7-chloro[1,3]thiazolo[5,4-d]pyrimidin-2-yl)propanoate, 7-chloro-2-(2-phenylethyl)[1,3]thiazolo[5,4-d]pyrimidine, 2-[(benzyloxy)methyl]-7-chloro[1,3]thiazolo[5,4-d]pyrimidine, N,N-dimethyl-7-(methylsulfonyl)[1,3]thiazolo[5,4-d]pyrimidine-2-carboxamide,

[7-(methylsulfonyl)[1,3]thiazolo[5,4-d]pyrimidin-2-yl]piperidin-1-yl)methanone,

N-[2-(dimethylamino)-2-oxoethyl]-N-methyl-7-(methylsulfonyl)[1,3]thiazolo[5,4-d]pyrimidine-2-carboxamide, N-[3-(dimethylamino)-3-oxopropyl]-N-methyl-7-(methylsulfonyl)[1,3]thiazolo[5,4-d]pyrimidine-2-carboxamide.

10. A method of inhibiting the MKNK-1 pathway comprising administering a therapeutically effective compound according to claim 1 to a patient in need thereof.

11. A method of treating a haematological tumour, solid tumour or metastases thereof selected from leukaemias and myelodysplastic syndrome, malignant lymphomas, head and neck tumours, brain tumours and brain metastases, tumours of the thorax, non-small cell and small cell lung tumours, gastrointestinal tumours, endocrine tumours, mammary and other gynaecological tumours, urological tumours, renal, bladder and prostate tumours, skin tumours, and sarcomas, and metastases thereof comprising administering to a patient in need thereof a therapeutic amount of a compound of claim 1.

* * * * *

SEQUENCE LISTING

```
<160> NUMBER OF SEQ ID NOS: 5

<210> SEQ ID NO 1
<211> LENGTH: 14
<212> TYPE: PRT
<213> ORGANISM: Unknown
<220> FEATURE:
<223> OTHER INFORMATION: biotin-Ahx-IKKRKLTRRKSLKG

<400> SEQUENCE: 1

Ile Lys Lys Arg Lys Leu Thr Arg Arg Lys Ser Leu Lys Gly
1               5                   10

<210> SEQ ID NO 2
<211> LENGTH: 14
<212> TYPE: PRT
<213> ORGANISM: Unknown
<220> FEATURE:
<223> OTHER INFORMATION: biotin-Ahx-AEEEEYFELVAKKK

<400> SEQUENCE: 2

Ala Glu Glu Glu Glu Tyr Phe Glu Leu Val Ala Lys Lys Lys
1               5                   10

<210> SEQ ID NO 3
<211> LENGTH: 14
<212> TYPE: PRT
<213> ORGANISM: Unknown
<220> FEATURE:
<223> OTHER INFORMATION: biotin-Ttds-YISPLKSPYKISEG

<400> SEQUENCE: 3

Tyr Ile Ser Pro Leu Lys Ser Pro Tyr Lys Ile Ser Glu Gly
1               5                   10

<210> SEQ ID NO 4
<211> LENGTH: 13
<212> TYPE: PRT
<213> ORGANISM: Unknown
<220> FEATURE:
```

-continued

```
<223> OTHER INFORMATION: biotin-KVEKIGEGTYGVV

<400> SEQUENCE: 4

Lys Val Glu Lys Ile Gly Glu Gly Thr Tyr Gly Val Val
1               5                   10

<210> SEQ ID NO 5
<211> LENGTH: 15
<212> TYPE: PRT
<213> ORGANISM: Unknown
<220> FEATURE:
<223> OTHER INFORMATION: Biotin-Ahx-GGEEEEYFELVKKKK

<400> SEQUENCE: 5

Gly Gly Glu Glu Glu Glu Tyr Phe Glu Leu Val Lys Lys Lys Lys
1               5                   10                  15
```